United States Patent
Weimei et al.

(10) Patent No.: US 11,851,714 B2
(45) Date of Patent: Dec. 26, 2023

(54) COMBINATIONS, DETECTION METHODS AND KITS OF DNA METHYLATION BIOMARKER

(71) Applicant: AnchorDx Medical Co., Ltd., Guangzhou (CN)

(72) Inventors: Ruan Weimei, Guangzhou (CN); Jiang Zeyu, Guangzhou (CN); Li Xia, Guangzhou (CN); Chen Zhiwei, Guangzhou (CN); Fan Jianbing, Guangzhou (CN)

(73) Assignee: AnchorDx Medical Co., Ltd., Guangzhou (CN)

( * ) Notice: Subject to any disclaimer, the term of this patent is extended or adjusted under 35 U.S.C. 154(b) by 0 days.

(21) Appl. No.: 17/036,424

(22) Filed: Sep. 29, 2020

(65) Prior Publication Data
US 2021/0198746 A1    Jul. 1, 2021

Related U.S. Application Data

(63) Continuation-in-part of application No. PCT/CN2020/072770, filed on Jan. 17, 2020.

(30) Foreign Application Priority Data

Dec. 26, 2019 (CN) .......................... 201911367385.4
Jun. 5, 2020 (CN) .......................... 202010506210.3

(51) Int. Cl.
  *C12Q 1/6886* (2018.01)
  *C12Q 1/6806* (2018.01)
  *G16B 5/00* (2019.01)

(52) U.S. Cl.
CPC ......... *C12Q 1/6886* (2013.01); *C12Q 1/6806* (2013.01); *G16B 5/00* (2019.02); *C12Q 2600/106* (2013.01); *C12Q 2600/112* (2013.01); *C12Q 2600/118* (2013.01); *C12Q 2600/154* (2013.01)

(58) Field of Classification Search
None
See application file for complete search history.

(56) References Cited

FOREIGN PATENT DOCUMENTS

| | | |
|---|---|---|
| CN | 108441561 A | 8/2018 |
| EP | 2644705 A1 | 10/2013 |
| WO | 2006133866 A2 | 12/2006 |

OTHER PUBLICATIONS

Feng (PNAS 2010 vol. 107 No. 19 pp. 8689-8694) (Year: 2010).*
Cobb et al (Crit Care Med 2002 vol. 30 p. 2711) (Year: 2002).*
Cross, SH et al. Genbank, May, 2, 2000, AJ236577.1.
Unknown, Predicted: Pan paniscus vimentin (VIM), mRNA, May 1, 2018.
Pan, DQ et al. Acta Univ. Med Anhui, 52(7), 952-956, 2017.
International Search Report on PCT/CN2020/072770.

* cited by examiner

*Primary Examiner* — Katherine D Salmon
(74) *Attorney, Agent, or Firm* — Yong Chen; Lin Sun-Hoffman; Liu Chen & Hoffman LLP

(57) ABSTRACT

The present disclosure relates to a DNA methylation markers combination for bladder cancer risk stratification, which includes methylation regions as denoted by any one or more of SEQ ID NOS:1-22 or any one or more of complementary sequences thereof. The present disclosure further provides a clinical application of the three-class stratification mode before operation based on the selected appropriate molecular marker combinations, to promote the rational use of current diagnosis and treatment methods, consequently patients with negative BC can avoid excessive invasive cystoscopy, while HR-NMIBC or MIBC can expedite diagnosis and surgical operations, and the definite LMR-NMIBC patients can follow standard diagnostic modalities.

12 Claims, 6 Drawing Sheets
Specification includes a Sequence Listing.

| Cohort 2 (independent validation) | | Prediction | | | Sensitivity | Specificity | PPV | NPV | Balanced Accuracy | F-measure | Overall Accuracy | Overall AUC |
|---|---|---|---|---|---|---|---|---|---|---|---|---|
| | | Non-BC | LMR-NMIBC | HR-NMIBC +MIBC | | | | | | | | |
| Reference Pathology | Non-BC | 34 | 3 | 2 | 84.7% | 87.2% | 90.0% | 79.1% | 86.0% | 87.7% | 79.6% | 0.863 |
| | LMR-NMIBC | 3 | 5 | 3 | 45.5% | 93.1% | 45.5% | 93.1% | 69.3% | 45.5% | | |
| | HR-NMIBC+MIBC | 6 | 3 | 39 | 81.2% | 90.0% | 88.6% | 83.3% | 85.6% | 84.8% | | |

Fig. 8

| SEQ ID NO | Combination | | | | | | | | | | | | Single Plex | Single Quantity |
|---|---|---|---|---|---|---|---|---|---|---|---|---|---|---|
| | A | B | C | D | E | F | G | H | I | J | K | L | | |
| 1 | 20.29 | 21.38 | | | | | | | | | | | | 18.04 |
| 2 | 23.12 | | 22.16 | | | | | | | | | | | 25.19 |
| 3 | | | | | 16.88 | | | | | | 23.17 | 18.36 | 17.22 | 15.92 |
| 4 | | | | | | | 14.86 | | | | | 14.65 | | 13.85 |
| 5 | | | | | | | 14.97 | | | | | | 14.54 | 13.95 |
| 6 | | | | 16.64 | | | | | | | | | | 17.76 |
| 7 | | | | | | | | | 14.50 | 14.13 | 15.96 | | 15.21 | 15.83 |
| 8 | | | 15.25 | | | | | | | | | | | 16.28 |
| 9 | | | 19.89 | | | | | | | | | | | 19.51 |
| 10 | | | | | | | | 16.30 | | | | | | 17.71 |
| 11 | | | | | | 17.89 | | | 21.78 | | | | | 20.63 |
| 12 | | | | | | | | 16.92 | | | | | | 17.22 |
| 13 | | | | | 17.98 | | | | | | | | | 16.78 |
| 14 | | | | 24.63 | | | | | | | | | | 16.21 |
| 15 | | | | | | 13.64 | | | | | | | | 25.50 |
| 16 | | | | | 21.08 | | | | | | | | | 13.92 |
| 17 | | 18.05 | | | | | | | 21.52 | | | | | 17.54 |
| 18 | | | | | | | | | | | | | | 20.47 |
| 19 | | 17.02 | | | | | | | | | | | | 20.71 |
| 20 | | | | | | | | 17.50 | | | | | | 16.02 |
| 21 | | | | | | | 18.15 | | | | | | | 16.98 |
| 22 | | | | | | | | | | | | | | 17.74 |
| internal ref. | 18.83 | | | 17.95 | | | | | | 18.21 | 17.96 | 20.29 | | 20.60 |

FIG. 9

SEQUENCE LISTING

```
<160> NUMBER OF SEQ ID NOS: 223

<210> SEQ ID NO 1
<211> LENGTH: 94
<212> TYPE: DNA
<213> ORGANISM: Artificial Sequence
<220> FEATURE:
<223> OTHER INFORMATION: Synthesized SEQ ID NO. 1

<400> SEQUENCE: 1
taggaagact cgggcaccgt tcagcgcatt ggcttcgcgg acccagccgc ccaggcggat      60
cgccggaagc gcaagtagcg gtgtgtgcgc acag                                 94

<210> SEQ ID NO 2
<211> LENGTH: 87
<212> TYPE: DNA
<213> ORGANISM: Artificial Sequence
<220> FEATURE:
<223> OTHER INFORMATION: Synthesized SEQ ID NO 2

<400> SEQUENCE: 2
atgttcggcg gcccgggcac cgcgagccgg ccgagctcca gccggagcta cgtgactacg      60
tccacccgca cctacagcct gggcagc                                         87

<210> SEQ ID NO 3
<211> LENGTH: 108
<212> TYPE: DNA
<213> ORGANISM: Artificial Sequence
<220> FEATURE:
<223> OTHER INFORMATION: Synthesized SEQ ID NO 3

<400> SEQUENCE: 3
ttggcggtca aagtggcccc gactcgggat gacaattgac ggggatcaag ggattgccca      60
ttctgtgcct gtaagaaccg attcgtgcca gagaaactca tcaagtgg                 108
```

```
<210> SEQ ID NO 4
<211> LENGTH: 89
<212> TYPE: DNA
<213> ORGANISM: Artificial Sequence
<220> FEATURE:
<223> OTHER INFORMATION: Synthesized SEQ ID NO 4

<400> SEQUENCE: 4
cgccgggctc cagggctccc gcgctccagt ggcccagcct gggcggagag cagagcgcgg      60
cccccgcggc cccgcggcct cgagccccg                                       89

<210> SEQ ID NO 5
<211> LENGTH: 84
<212> TYPE: DNA
<213> ORGANISM: Artificial Sequence
<220> FEATURE:
<223> OTHER INFORMATION: Synthesized SEQ ID NO 5

<400> SEQUENCE: 5
cccggagtgg ggcaggtgtc ggagctgggt gggaagcaga cgcggtacgg tgggcagagg      60
tccccagcct gcggggagcg ctat                                            84

<210> SEQ ID NO 6
<211> LENGTH: 82
<212> TYPE: DNA
<213> ORGANISM: Artificial Sequence
<220> FEATURE:
<223> OTHER INFORMATION: Synthesized SEQ ID NO 6

<400> SEQUENCE: 6
ccggtggtgc accacgaggg ctacccgttt gccgccgccg ccgccgcagc tgccgccgcc      60
gccgccagcc gctgcagcca tg                                              82

<210> SEQ ID NO 7
<211> LENGTH: 106
<212> TYPE: DNA
<213> ORGANISM: Artificial Sequence
<220> FEATURE:
<223> OTHER INFORMATION: Synthesized SEQ ID NO 7

<400> SEQUENCE: 7
cgggaactga gtgctggccc gggagaccct ccggagagct cgcgggctcg gcctcggcct      60
cggcctcggc cttcggccgc ggttaccgaa acacagacgg tagact                    106

<210> SEQ ID NO 8
<211> LENGTH: 86
<212> TYPE: DNA
<213> ORGANISM: Artificial Sequence
<220> FEATURE:
<223> OTHER INFORMATION: Synthesized SEQ ID NO 8

<400> SEQUENCE: 8
ctcccgcgcc cccgccccg cgttccggcc tggcctgcgg gattcgggcc gaggcaactg       60
cagggacggg gcacccctcc tgctcc                                          86

<210> SEQ ID NO 9
<211> LENGTH: 89
<212> TYPE: DNA
<213> ORGANISM: Artificial Sequence
<220> FEATURE:
<223> OTHER INFORMATION: Synthesized SEQ ID NO 9

<400> SEQUENCE: 9
```

```
tggagagggg tcatccgccc cggaaccgac gtgagcgcgg ggccggcccg tggaggcggc    60
tgagggatcc cccacttcca gcccgcccg                                      89

<210> SEQ ID NO 10
<211> LENGTH: 87
<212> TYPE: DNA
<213> ORGANISM: Artificial Sequence
<220> FEATURE:
<223> OTHER INFORMATION: Synthesized SEQ ID NO 10

<400> SEQUENCE: 10
gcagcagctg caggaagcgg actcggcgga aaggagcccc ggaggggaac tgagtgcctt    60
cagccaggca cgttcgggga gacagcg                                        87

<210> SEQ ID NO 11
<211> LENGTH: 89
<212> TYPE: DNA
<213> ORGANISM: Artificial Sequence
<220> FEATURE:
<223> OTHER INFORMATION: Synthesized SEQ ID NO 11

<400> SEQUENCE: 11
tgccgcaaaa ttcgcagacg aagggcttgt agcccgcgtg gatgcggata tgcgtgttga    60
gcgtggagct gcggttgaac gctttgccg                                      89

<210> SEQ ID NO 12
<211> LENGTH: 109
<212> TYPE: DNA
<213> ORGANISM: Artificial Sequence
<220> FEATURE:
<223> OTHER INFORMATION: Synthesized SEQ ID NO 12

<400> SEQUENCE: 12
tgctacccca gccgtgtccc gctccggaga ccccagggcg ccgggaccca tctgccgctc    60
gccggccgga ggctaccagg agcaggagca gcagcgccgc ccgcagtag              109

<210> SEQ ID NO 13
<211> LENGTH: 111
<212> TYPE: DNA
<213> ORGANISM: Artificial Sequence
<220> FEATURE:
<223> OTHER INFORMATION: Synthesized SEQ ID NO 13

<400> SEQUENCE: 13
cggccttccg gtggggcacc aaaagggaag cctcctcggc ccctggcgac ccggtgactt    60
gcagcggcgt gtgattaatc ttccacagct gtcgtgcccc atccacttga g            111

<210> SEQ ID NO 14
<211> LENGTH: 93
<212> TYPE: DNA
<213> ORGANISM: Artificial Sequence
<220> FEATURE:
<223> OTHER INFORMATION: Synthesized SEQ ID NO 14

<400> SEQUENCE: 14
gcaaccggca gcgtccagct cccgcacctc gctgcacatc gcacctgagc ccgccgcga    60 ccgcatcgcg ctcgctgcga cccattcaga ccc                                 93

<210> SEQ ID NO 15
<211> LENGTH: 116
<212> TYPE: DNA
```

```
<213> ORGANISM: Artificial Sequence
<220> FEATURE:
<223> OTHER INFORMATION: Synthesized SEQ ID NO 15

<400> SEQUENCE: 15
cttcagctgc cctcgatttt gctccacgcc tgccggccag agcctcccgg cgtttcttcc    60
gccccagcgg agtgcgctgg ggcgcgccag ggctaggccc gccggaggag cgcgtc       116

<210> SEQ ID NO 16
<211> LENGTH: 101
<212> TYPE: DNA
<213> ORGANISM: Artificial Sequence
<220> FEATURE:
<223> OTHER INFORMATION: Synthesized SEQ ID NO 16

<400> SEQUENCE: 16
cgtgtctgag gctcgcgggc aactggaact gagagtctga gttggcctcg cgggagccgc    60
cagaagggtg cgggctgcgt gtggcagagt aggagcactg t                        101

<210> SEQ ID NO 17
<211> LENGTH: 85
<212> TYPE: DNA
<213> ORGANISM: Artificial Sequence
<220> FEATURE:
<223> OTHER INFORMATION: Synthesized SEQ ID NO 17

<400> SEQUENCE: 17
tcggcagtgg ccaccacatc tggttctcgt taactttct aaggcagcgg ccgctggagc     60
agcggggctg gcggggtaaa agctc                                           85

<210> SEQ ID NO 18
<211> LENGTH: 73
<212> TYPE: DNA
<213> ORGANISM: Artificial Sequence
<220> FEATURE:
<223> OTHER INFORMATION: Synthesized SEQ ID NO 18

<400> SEQUENCE: 18
cgcggccacc gcccgttcat cacccgcgcg catctgggct ggcaccgggc gaagaatcgt    60
gcgggtctgg gac                                                        73

<210> SEQ ID NO 19
<211> LENGTH: 112
<212> TYPE: DNA
<213> ORGANISM: Artificial Sequence
<220> FEATURE:
<223> OTHER INFORMATION: Synthesized SEQ ID NO 19

<400> SEQUENCE: 19
agattgcgcg gagcccacgc gatccctggg acgccggaga caacggggct cttgggaagg    60
cgcggagccc ggggaagccg gggatgtgcg cgtgagccgt gcccgcaggg tc            112

<210> SEQ ID NO 20
<211> LENGTH: 93
<212> TYPE: DNA
<213> ORGANISM: Artificial Sequence
<220> FEATURE:
<223> OTHER INFORMATION: Synthesized SEQ ID NO 20

<400> SEQUENCE: 20
ggagcgtgcg ggcagcgccc ccgaaccta gcgcagccca ggaagcggtc ggaggagact     60
gtcctggccg cggtggcagc cccatccgga gtg                                  93
```

<210> SEQ ID NO 21
<211> LENGTH: 99
<212> TYPE: DNA
<213> ORGANISM: Artificial Sequence
<220> FEATURE:
<223> OTHER INFORMATION: Synthesized SEQ ID NO 21

<400> SEQUENCE: 21
aaaactgatc cgtgtcctgc atgttggcag cagacaacct tccttgctgc tgagctgtcc    60
cgggtggctt caccgcggct ggggaatccg agccattcc    99

<210> SEQ ID NO 22
<211> LENGTH: 93
<212> TYPE: DNA
<213> ORGANISM: Artificial Sequence
<220> FEATURE:
<223> OTHER INFORMATION: Synthesized SEQ ID NO 22

<400> SEQUENCE: 22
ggagagaaag tcctatctgc agcagccgaa tggtccccat tccggtaatg ggacggcggg    60
agcatttggg aggacgcgat tctaaagaga gcg    93

<210> SEQ ID NO 23
<211> LENGTH: 26
<212> TYPE: DNA
<213> ORGANISM: Artificial Sequence
<220> FEATURE:
<223> OTHER INFORMATION: Synthesized SEQ ID NO 23

<400> SEQUENCE: 23
ggaagattcg ggtatcgttt agcgta    26

<210> SEQ ID NO 24
<211> LENGTH: 21
<212> TYPE: DNA
<213> ORGANISM: Artificial Sequence
<220> FEATURE:
<223> OTHER INFORMATION: Synthesized SEQ ID NO 24

<400> SEQUENCE: 24
tgttcggcgg ttcgggtatc g    21

<210> SEQ ID NO 25
<211> LENGTH: 21
<212> TYPE: DNA
<213> ORGANISM: Artificial Sequence
<220> FEATURE:
<223> OTHER INFORMATION: Synthesized SEQ ID NO 25

<400> SEQUENCE: 25
tggcggttaa agtggtttcg a    21

<210> SEQ ID NO 26
<211> LENGTH: 21
<212> TYPE: DNA
<213> ORGANISM: Artificial Sequence
<220> FEATURE:
<223> OTHER INFORMATION: Synthesized SEQ ID NO 26

<400> SEQUENCE: 26
cgggttttag ggttttcgcg t    21

<210> SEQ ID NO 27

<210> SEQ ID NO 27
<211> LENGTH: 20
<212> TYPE: DNA
<213> ORGANISM: Artificial Sequence
<220> FEATURE:
<223> OTHER INFORMATION: Synthesized SEQ ID NO 27

<400> SEQUENCE: 27
ttcggagtgg ggtaggtgtc                                            20

<210> SEQ ID NO 28
<211> LENGTH: 22
<212> TYPE: DNA
<213> ORGANISM: Artificial Sequence
<220> FEATURE:
<223> OTHER INFORMATION: Synthesized SEQ ID NO 28

<400> SEQUENCE: 28
tcggtggtgt attacgaggg tt                                         22

<210> SEQ ID NO 29
<211> LENGTH: 21
<212> TYPE: DNA
<213> ORGANISM: Artificial Sequence
<220> FEATURE:
<223> OTHER INFORMATION: Synthesized SEQ ID NO 29

<400> SEQUENCE: 29
gcgggaattg agtgttggtt c                                          21

<210> SEQ ID NO 30
<211> LENGTH: 20
<212> TYPE: DNA
<213> ORGANISM: Artificial Sequence
<220> FEATURE:
<223> OTHER INFORMATION: Synthesized SEQ ID NO 30

<400> SEQUENCE: 30
tcgcgttttc gttttcgcgt                                            20

<210> SEQ ID NO 31
<211> LENGTH: 24
<212> TYPE: DNA
<213> ORGANISM: Artificial Sequence
<220> FEATURE:
<223> OTHER INFORMATION: Synthesized SEQ ID NO 31

<400> SEQUENCE: 31
attcgtttcg gaatcgacgt gagc                                       24

<210> SEQ ID NO 32
<211> LENGTH: 24
<212> TYPE: DNA
<213> ORGANISM: Artificial Sequence
<220> FEATURE:
<223> OTHER INFORMATION: Synthesized SEQ ID NO 32

<400> SEQUENCE: 32
gtagtagttg taggaagcgg attc                                       24

<210> SEQ ID NO 33
<211> LENGTH: 21
<212> TYPE: DNA
<213> ORGANISM: Artificial Sequence
<220> FEATURE:
<223> OTHER INFORMATION: Synthesized SEQ ID NO 33

<400> SEQUENCE: 33
acgacaaaac gttcaaccgc a                                              21

<210> SEQ ID NO 34
<211> LENGTH: 26
<212> TYPE: DNA
<213> ORGANISM: Artificial Sequence
<220> FEATURE:
<223> OTHER INFORMATION: Synthesized SEQ ID NO 34

<400> SEQUENCE: 34
ttattttagt cgtgtttcgt ttcgga                                         26

<210> SEQ ID NO 35
<211> LENGTH: 22
<212> TYPE: DNA
<213> ORGANISM: Artificial Sequence
<220> FEATURE:
<223> OTHER INFORMATION: Synthesized SEQ ID NO 35

<400> SEQUENCE: 35
tcggtggggt attaaaaggg aa                                             22

<210> SEQ ID NO 36
<211> LENGTH: 25
<212> TYPE: DNA
<213> ORGANISM: Artificial Sequence
<220> FEATURE:
<223> OTHER INFORMATION: Synthesized SEQ ID NO 36

<400> SEQUENCE: 36
cggtagcgtt tagttttcgt atttc                                          25

<210> SEQ ID NO 37
<211> LENGTH: 25
<212> TYPE: DNA
<213> ORGANISM: Artificial Sequence
<220> FEATURE:
<223> OTHER INFORMATION: Synthesized SEQ ID NO 37

<400> SEQUENCE: 37
tttcgatttt gttttacgtt tgtcg                                          25

<210> SEQ ID NO 38
<211> LENGTH: 20
<212> TYPE: DNA
<213> ORGANISM: Artificial Sequence
<220> FEATURE:
<223> OTHER INFORMATION: Synthesized SEQ ID NO 38

<400> SEQUENCE: 38
cgtgtttgag gttcgcgggt                                                20

<210> SEQ ID NO 39
<211> LENGTH: 28
<212> TYPE: DNA
<213> ORGANISM: Artificial Sequence
<220> FEATURE:
<223> OTHER INFORMATION: Synthesized SEQ ID NO 39

<400> SEQUENCE: 39
tcggtagtgg ttattatatt tggttttc                                       28

<210> SEQ ID NO 40
<211> LENGTH: 25
<212> TYPE: DNA

```
<213> ORGANISM: Artificial Sequence
<220> FEATURE:
<223> OTHER INFORMATION: Synthesized SEQ ID NO 40

<400> SEQUENCE: 40
cgcggttatc gttcgtttat tattc                                   25

<210> SEQ ID NO 41
<211> LENGTH: 20
<212> TYPE: DNA
<213> ORGANISM: Artificial Sequence
<220> FEATURE:
<223> OTHER INFORMATION: Synthesized SEQ ID NO 41

<400> SEQUENCE: 41
tgcgcggagt ttacgcgatt                                         20

<210> SEQ ID NO 42
<211> LENGTH: 19
<212> TYPE: DNA
<213> ORGANISM: Artificial Sequence
<220> FEATURE:
<223> OTHER INFORMATION: Synthesized SEQ ID NO 42

<400> SEQUENCE: 42
ggagcgtgcg ggtagcgtt                                          19

<210> SEQ ID NO 43
<211> LENGTH: 27
<212> TYPE: DNA
<213> ORGANISM: Artificial Sequence
<220> FEATURE:
<223> OTHER INFORMATION: Synthesized SEQ ID NO 43

<400> SEQUENCE: 43
ttgattcgtg ttttgtatgt tggtagt                                 27

<210> SEQ ID NO 44
<211> LENGTH: 29
<212> TYPE: DNA
<213> ORGANISM: Artificial Sequence
<220> FEATURE:
<223> OTHER INFORMATION: Synthesized SEQ ID NO 44

<400> SEQUENCE: 44
gagagaaagt tttatttgta gtagtcgaa                               29

<210> SEQ ID NO 45
<211> LENGTH: 25
<212> TYPE: DNA
<213> ORGANISM: Artificial Sequence
<220> FEATURE:
<223> OTHER INFORMATION: Synthesized SEQ ID NO 45

<400> SEQUENCE: 45
gcacacaccg ctacttacgc ttccg                                   25

<210> SEQ ID NO 46
<211> LENGTH: 30
<212> TYPE: DNA
<213> ORGANISM: Artificial Sequence
<220> FEATURE:
<223> OTHER INFORMATION: Synthesized SEQ ID NO 46

<400> SEQUENCE: 46
gctacccaaa ctataaatac gaataaacgt                              30
```

<210> SEQ ID NO 47
<211> LENGTH: 31
<212> TYPE: DNA
<213> ORGANISM: Artificial Sequence
<220> FEATURE:
<223> OTHER INFORMATION: Synthesized SEQ ID NO 47

<400> SEQUENCE: 47
cacttaataa atttctctaa cacgaatcga t                              31

<210> SEQ ID NO 48
<211> LENGTH: 21
<212> TYPE: DNA
<213> ORGANISM: Artificial Sequence
<220> FEATURE:
<223> OTHER INFORMATION: Synthesized SEQ ID NO 48

<400> SEQUENCE: 48
cgaaactcga aaccgcgaaa c                                         21

<210> SEQ ID NO 49
<211> LENGTH: 21
<212> TYPE: DNA
<213> ORGANISM: Artificial Sequence
<220> FEATURE:
<223> OTHER INFORMATION: Synthesized SEQ ID NO 49

<400> SEQUENCE: 49
ataacgctcc ccgcaaacta a                                         21

<210> SEQ ID NO 50
<211> LENGTH: 21
<212> TYPE: DNA
<213> ORGANISM: Artificial Sequence
<220> FEATURE:
<223> OTHER INFORMATION: Synthesized SEQ ID NO 50

<400> SEQUENCE: 50
aacgactaac gacgacgacg a                                         21

<210> SEQ ID NO 51
<211> LENGTH: 26
<212> TYPE: DNA
<213> ORGANISM: Artificial Sequence
<220> FEATURE:
<223> OTHER INFORMATION: Synthesized SEQ ID NO 51

<400> SEQUENCE: 51
taccgtctat atttcgataa ccgcga                                    26

<210> SEQ ID NO 52
<211> LENGTH: 23
<212> TYPE: DNA
<213> ORGANISM: Artificial Sequence
<220> FEATURE:
<223> OTHER INFORMATION: Synthesized SEQ ID NO 52

<400> SEQUENCE: 52 atacccgtc cctacaatta cct                                        23

<210> SEQ ID NO 53
<211> LENGTH: 17
<212> TYPE: DNA
<213> ORGANISM: Artificial Sequence
<220> FEATURE:

<223> OTHER INFORMATION: Synthesized SEQ ID NO 53

<400> SEQUENCE: 53
cgaacgaact aaaaata                          17

<210> SEQ ID NO 54
<211> LENGTH: 21
<212> TYPE: DNA
<213> ORGANISM: Artificial Sequence
<220> FEATURE:
<223> OTHER INFORMATION: Synthesized SEQ ID NO 54

<400> SEQUENCE: 54
cgctatctcc ccgaacgtac c                     21

<210> SEQ ID NO 55
<211> LENGTH: 25
<212> TYPE: DNA
<213> ORGANISM: Artificial Sequence
<220> FEATURE:
<223> OTHER INFORMATION: Synthesized SEQ ID NO 55

<400> SEQUENCE: 55
tttgtcgtaa aattcgtaga cgaag                 25

<210> SEQ ID NO 56
<211> LENGTH: 25
<212> TYPE: DNA
<213> ORGANISM: Artificial Sequence
<220> FEATURE:
<223> OTHER INFORMATION: Synthesized SEQ ID NO 56

<400> SEQUENCE: 56
ctacgaacga cgctactact cctac                 25

<210> SEQ ID NO 57
<211> LENGTH: 23
<212> TYPE: DNA
<213> ORGANISM: Artificial Sequence
<220> FEATURE:
<223> OTHER INFORMATION: Synthesized SEQ ID NO 57

<400> SEQUENCE: 57
taaataaaac acgacaacta taa                   23

<210> SEQ ID NO 58
<211> LENGTH: 24
<212> TYPE: DNA
<213> ORGANISM: Artificial Sequence
<220> FEATURE:
<223> OTHER INFORMATION: Synthesized SEQ ID NO 58

<400> SEQUENCE: 58
ctaaataaat cgcaacgaac gcga                  24

<210> SEQ ID NO 59
<211> LENGTH: 17
<212> TYPE: DNA
<213> ORGANISM: Artificial Sequence
<220> FEATURE:
<223> OTHER INFORMATION: Synthesized SEQ ID NO 59

<400> SEQUENCE: 59
aacgcgctcc tccgacg                          17

```
<210> SEQ ID NO 60
<211> LENGTH: 25
<212> TYPE: DNA
<213> ORGANISM: Artificial Sequence
<220> FEATURE:
<223> OTHER INFORMATION: Synthesized SEQ ID NO 60

<400> SEQUENCE: 60
ctactctacc acacgcaacc cgcac                                              25

<210> SEQ ID NO 61
<211> LENGTH: 21
<212> TYPE: DNA
<213> ORGANISM: Artificial Sequence
<220> FEATURE:
<223> OTHER INFORMATION: Synthesized SEQ ID NO 61

<400> SEQUENCE: 61 actttttaccc cgccaaccccc g                                                21

<210> SEQ ID NO 62
<211> LENGTH: 19
<212> TYPE: DNA
<213> ORGANISM: Artificial Sequence
<220> FEATURE:
<223> OTHER INFORMATION: Synthesized SEQ ID NO 62

<400> SEQUENCE: 62
atcccaaacc cgcacgatt                                                     19

<210> SEQ ID NO 63
<211> LENGTH: 20
<212> TYPE: DNA
<213> ORGANISM: Artificial Sequence
<220> FEATURE:
<223> OTHER INFORMATION: Synthesized SEQ ID NO 63

<400> SEQUENCE: 63
acgaacacga ctcacgcgca                                                    20

<210> SEQ ID NO 64
<211> LENGTH: 21
<212> TYPE: DNA
<213> ORGANISM: Artificial Sequence
<220> FEATURE:
<223> OTHER INFORMATION: Synthesized SEQ ID NO 64

<400> SEQUENCE: 64
cgaataaaac taccaccgcg a                                                  21

<210> SEQ ID NO 65
<211> LENGTH: 23
<212> TYPE: DNA
<213> ORGANISM: Artificial Sequence
<220> FEATURE:
<223> OTHER INFORMATION: Synthesized SEQ ID NO 65

<400> SEQUENCE: 65
aaaataactc gaattcccca acc                                                23

<210> SEQ ID NO 66
<211> LENGTH: 23
<212> TYPE: DNA
<213> ORGANISM: Artificial Sequence
<220> FEATURE:
<223> OTHER INFORMATION: Synthesized SEQ ID NO 66
```

<400> SEQUENCE: 66
acgctctctt taaaatcgcg tcc                                              23

<210> SEQ ID NO 67
<211> LENGTH: 28
<212> TYPE: DNA
<213> ORGANISM: Artificial Sequence
<220> FEATURE:
<223> OTHER INFORMATION: Synthesized SEQ ID NO 67

<400> SEQUENCE: 67
cgatccgcct aaacgactaa atccgcga                                         28

<210> SEQ ID NO 68
<211> LENGTH: 30
<212> TYPE: DNA
<213> ORGANISM: Artificial Sequence
<220> FEATURE:
<223> OTHER INFORMATION: Synthesized SEQ ID NO 68

<400> SEQUENCE: 68
gagtcggtcg agttttagtc ggagttacgt                                       30

<210> SEQ ID NO 69
<211> LENGTH: 29
<212> TYPE: DNA
<213> ORGANISM: Artificial Sequence
<220> FEATURE:
<223> OTHER INFORMATION: Synthesized SEQ ID NO 69

<400> SEQUENCE: 69
cccttaatcc ccgtcaatta tcatcccga                                        29

<210> SEQ ID NO 70
<211> LENGTH: 24
<212> TYPE: DNA
<213> ORGANISM: Artificial Sequence
<220> FEATURE:
<223> OTHER INFORMATION: Synthesized SEQ ID NO 70

<400> SEQUENCE: 70
gcgaaaaccg cgctctactc tccg                                             24

<210> SEQ ID NO 71
<211> LENGTH: 29
<212> TYPE: DNA
<213> ORGANISM: Artificial Sequence
<220> FEATURE:
<223> OTHER INFORMATION: Synthesized SEQ ID NO 71

<400> SEQUENCE: 71
cctctaccca ccgtaccgcg tctacttcc                                        29

<210> SEQ ID NO 72
<211> LENGTH: 23
<212> TYPE: DNA
<213> ORGANISM: Artificial Sequence
<220> FEATURE:
<223> OTHER INFORMATION: Synthesized SEQ ID NO 72

<400> SEQUENCE: 72
tacgacgacg acgacgacaa acg                                              23

<210> SEQ ID NO 73
<211> LENGTH: 26

```
<212> TYPE: DNA
<213> ORGANISM: Artificial Sequence
<220> FEATURE:
<223> OTHER INFORMATION: Synthesized SEQ ID NO 73

<400> SEQUENCE: 73
cgaaaccgaa cccgcgaact ctccga                                          26

<210> SEQ ID NO 74
<211> LENGTH: 25
<212> TYPE: DNA
<213> ORGANISM: Artificial Sequence
<220> FEATURE:
<223> OTHER INFORMATION: Synthesized SEQ ID NO 74

<400> SEQUENCE: 74
gacccgaatc ccgcaaacca aaccg                                           25

<210> SEQ ID NO 75
<211> LENGTH: 21
<212> TYPE: DNA
<213> ORGANISM: Artificial Sequence
<220> FEATURE:
<223> OTHER INFORMATION: Synthesized SEQ ID NO 75

<400> SEQUENCE: 75
cgcctccacg aaccgacccc g                                               21

<210> SEQ ID NO 76
<211> LENGTH: 28
<212> TYPE: DNA
<213> ORGANISM: Artificial Sequence
<220> FEATURE:
<223> OTHER INFORMATION: Synthesized SEQ ID NO 76

<400> SEQUENCE: 76
tcaattcccc tccgaaactc ctttccgc                                        28

<210> SEQ ID NO 77
<211> LENGTH: 28
<212> TYPE: DNA
<213> ORGANISM: Artificial Sequence
<220> FEATURE:
<223> OTHER INFORMATION: Synthesized SEQ ID NO 77

<400> SEQUENCE: 77
cgctcaacac gcatatccgc atccacgc                                        28

<210> SEQ ID NO 78
<211> LENGTH: 30
<212> TYPE: DNA
<213> ORGANISM: Artificial Sequence
<220> FEATURE:
<223> OTHER INFORMATION: Synthesized SEQ ID NO 78

<400> SEQUENCE: 78
cgaccgacga acgacaaata aatcccgacg                                      30

<210> SEQ ID NO 79
<211> LENGTH: 32
<212> TYPE: DNA
<213> ORGANISM: Artificial Sequence
<220> FEATURE:
<223> OTHER INFORMATION: Synthesized SEQ ID NO 79

<400> SEQUENCE: 79
```

```
cggttttttgg cgattcggtg atttgtagcg gc                          32
```

<210> SEQ ID NO 80
<211> LENGTH: 30
<212> TYPE: DNA
<213> ORGANISM: Artificial Sequence
<220> FEATURE:
<223> OTHER INFORMATION: Synthesized SEQ ID NO 80

<400> SEQUENCE: 80

```
cgatcgcgac gaaactcaaa tacgatatac                              30
```

<210> SEQ ID NO 81
<211> LENGTH: 27
<212> TYPE: DNA
<213> ORGANISM: Artificial Sequence
<220> FEATURE:
<223> OTHER INFORMATION: Synthesized SEQ ID NO 81

<400> SEQUENCE: 81

```
cgccccaacg cactccgcta aaacgaa                                 27
```

<210> SEQ ID NO 82
<211> LENGTH: 26
<212> TYPE: DNA
<213> ORGANISM: Artificial Sequence
<220> FEATURE:
<223> OTHER INFORMATION: Synthesized SEQ ID NO 82

<400> SEQUENCE: 82

```
cttctaacga ctcccgcgaa accaac                                  26
```

<210> SEQ ID NO 83
<211> LENGTH: 20
<212> TYPE: DNA
<213> ORGANISM: Artificial Sequence
<220> FEATURE:
<223> OTHER INFORMATION: Synthesized SEQ ID NO 83

<400> SEQUENCE: 83

```
aaggtagcgg tcgttggagt                                         20
```

<210> SEQ ID NO 84
<211> LENGTH: 26
<212> TYPE: DNA
<213> ORGANISM: Artificial Sequence
<220> FEATURE:
<223> OTHER INFORMATION: Synthesized SEQ ID NO 84

<400> SEQUENCE: 84

```
tcgcccgata ccaacccaaa tacgcg                                  26
```

<210> SEQ ID NO 85
<211> LENGTH: 28
<212> TYPE: DNA
<213> ORGANISM: Artificial Sequence
<220> FEATURE:
<223> OTHER INFORMATION: Synthesized SEQ ID NO 85

<400> SEQUENCE: 85

```
cgaactccgc gccttcccaa aaaccccg                                28
```

<210> SEQ ID NO 86
<211> LENGTH: 30
<212> TYPE: DNA
<213> ORGANISM: Artificial Sequence

```
<220> FEATURE:
<223> OTHER INFORMATION: Synthesized SEQ ID NO 86

<400> SEQUENCE: 86
cgaccgcttc ctaaactacg ctaaaattcg                                          30

<210> SEQ ID NO 87
<211> LENGTH: 28
<212> TYPE: DNA
<213> ORGANISM: Artificial Sequence
<220> FEATURE:
<223> OTHER INFORMATION: Synthesized SEQ ID NO 87

<400> SEQUENCE: 87
cgataaaacc acccgaaaca actcaaca                                            28

<210> SEQ ID NO 88
<211> LENGTH: 26
<212> TYPE: DNA
<213> ORGANISM: Artificial Sequence
<220> FEATURE:
<223> OTHER INFORMATION: Synthesized SEQ ID NO 88

<400> SEQUENCE: 88
actcccgccg tcccattacc gaaata                                              26

<210> SEQ ID NO 89
<211> LENGTH: 24
<212> TYPE: DNA
<213> ORGANISM: Artificial Sequence
<220> FEATURE:
<223> OTHER INFORMATION: Synthesized SEQ ID NO 89

<400> SEQUENCE: 89
tatacgcaca caccgctact tacg                                                24

<210> SEQ ID NO 90
<211> LENGTH: 21
<212> TYPE: DNA
<213> ORGANISM: Artificial Sequence
<220> FEATURE:
<223> OTHER INFORMATION: Synthesized SEQ ID NO 90

<400> SEQUENCE: 90
atgttcggcg gttcgggtat c                                                   21

<210> SEQ ID NO 91
<211> LENGTH: 21
<212> TYPE: DNA
<213> ORGANISM: Artificial Sequence
<220> FEATURE:
<223> OTHER INFORMATION: Synthesized SEQ ID NO 91

<400> SEQUENCE: 91
ttggcggtta aagtggtttc g                                                   21

<210> SEQ ID NO 92
<211> LENGTH: 21
<212> TYPE: DNA
<213> ORGANISM: Artificial Sequence
<220> FEATURE:
<223> OTHER INFORMATION: Synthesized SEQ ID NO 92

<400> SEQUENCE: 92
gaaactcgaa accgcgaaac c                                                   21
```

<210> SEQ ID NO 93
<211> LENGTH: 21
<212> TYPE: DNA
<213> ORGANISM: Artificial Sequence
<220> FEATURE:
<223> OTHER INFORMATION: Synthesized SEQ ID NO 93

<400> SEQUENCE: 93
taacgctccc cgcaaactaa a                                               21

<210> SEQ ID NO 94
<211> LENGTH: 24
<212> TYPE: DNA
<213> ORGANISM: Artificial Sequence
<220> FEATURE:
<223> OTHER INFORMATION: Synthesized SEQ ID NO 94

<400> SEQUENCE: 94
cataactaca acgactaacg acga                                            24

<210> SEQ ID NO 95
<211> LENGTH: 21
<212> TYPE: DNA
<213> ORGANISM: Artificial Sequence
<220> FEATURE:
<223> OTHER INFORMATION: Synthesized SEQ ID NO 95

<400> SEQUENCE: 95
cgggaattga gtgttggttc g                                               21

<210> SEQ ID NO 96
<211> LENGTH: 23
<212> TYPE: DNA
<213> ORGANISM: Artificial Sequence
<220> FEATURE:
<223> OTHER INFORMATION: Synthesized SEQ ID NO 96

<400> SEQUENCE: 96 aatacccgt ccctacaatt acc                                              23

<210> SEQ ID NO 97
<211> LENGTH: 21
<212> TYPE: DNA
<213> ORGANISM: Artificial Sequence
<220> FEATURE:
<223> OTHER INFORMATION: Synthesized SEQ ID NO 97

<400> SEQUENCE: 97
cgactccgaa cgaacgaact a                                               21

<210> SEQ ID NO 98
<211> LENGTH: 22
<212> TYPE: DNA
<213> ORGANISM: Artificial Sequence
<220> FEATURE:
<223> OTHER INFORMATION: Synthesized SEQ ID NO 98

<400> SEQUENCE: 98
gctatctccc cgaacgtacc ta                                              22

<210> SEQ ID NO 99
<211> LENGTH: 24
<212> TYPE: DNA
<213> ORGANISM: Artificial Sequence
<220> FEATURE:
<223> OTHER INFORMATION: Synthesized SEQ ID NO 99

```
<400> SEQUENCE: 99
tgtcgtaaaa ttcgtagacg aagg                                            24

<210> SEQ ID NO 100
<211> LENGTH: 26
<212> TYPE: DNA
<213> ORGANISM: Artificial Sequence
<220> FEATURE:
<223> OTHER INFORMATION: Synthesized SEQ ID NO 100

<400> SEQUENCE: 100
tgttatttta gtcgtgtttc gtttcg                                          26

<210> SEQ ID NO 101
<211> LENGTH: 28
<212> TYPE: DNA
<213> ORGANISM: Artificial Sequence
<220> FEATURE:
<223> OTHER INFORMATION: Synthesized SEQ ID NO 101

<400> SEQUENCE: 101
ctcaactcaa ataaataaaa cacgacaa                                        28

<210> SEQ ID NO 102
<211> LENGTH: 24
<212> TYPE: DNA
<213> ORGANISM: Artificial Sequence
<220> FEATURE:
<223> OTHER INFORMATION: Synthesized SEQ ID NO 102

<400> SEQUENCE: 102
gtaatcggta gcgtttagtt ttcg                                            24

<210> SEQ ID NO 103
<211> LENGTH: 28
<212> TYPE: DNA
<213> ORGANISM: Artificial Sequence
<220> FEATURE:
<223> OTHER INFORMATION: Synthesized SEQ ID NO 103

<400> SEQUENCE: 103
tttttagttg ttttcgattt tgttttac                                        28

<210> SEQ ID NO 104
<211> LENGTH: 26
<212> TYPE: DNA
<213> ORGANISM: Artificial Sequence
<220> FEATURE:
<223> OTHER INFORMATION: Synthesized SEQ ID NO 104

<400> SEQUENCE: 104
acaatactcc tactctacca cacgca                                          26

<210> SEQ ID NO 105
<211> LENGTH: 28
<212> TYPE: DNA
<213> ORGANISM: Artificial Sequence
<220> FEATURE:
<223> OTHER INFORMATION: Synthesized SEQ ID NO 105

<400> SEQUENCE: 105
cggtagtggt tattatattt ggttttcg                                        28

<210> SEQ ID NO 106
```

```
<211> LENGTH: 25
<212> TYPE: DNA
<213> ORGANISM: Artificial Sequence
<220> FEATURE:
<223> OTHER INFORMATION: Synthesized SEQ ID NO 106

<400> SEQUENCE: 106
gcggttatcg ttcgtttatt attcg                                   25

<210> SEQ ID NO 107
<211> LENGTH: 22
<212> TYPE: DNA
<213> ORGANISM: Artificial Sequence
<220> FEATURE:
<223> OTHER INFORMATION: Synthesized SEQ ID NO 107

<400> SEQUENCE: 107
aaccctacga acacgactca cg                                      22

<210> SEQ ID NO 108
<211> LENGTH: 18
<212> TYPE: DNA
<213> ORGANISM: Artificial Sequence
<220> FEATURE:
<223> OTHER INFORMATION: Synthesized SEQ ID NO 108

<400> SEQUENCE: 108
cgtgcgggta gcgttttc                                           18

<210> SEQ ID NO 109
<211> LENGTH: 27
<212> TYPE: DNA
<213> ORGANISM: Artificial Sequence
<220> FEATURE:
<223> OTHER INFORMATION: Synthesized SEQ ID NO 109

<400> SEQUENCE: 109
aaaattgatt cgtgttttgt atgttgg                                 27

<210> SEQ ID NO 110
<211> LENGTH: 23
<212> TYPE: DNA
<213> ORGANISM: Artificial Sequence
<220> FEATURE:
<223> OTHER INFORMATION: Synthesized SEQ ID NO 110

<400> SEQUENCE: 110
gctctcttta aaatcgcgtc ctc                                     23

<210> SEQ ID NO 111
<211> LENGTH: 25
<212> TYPE: DNA
<213> ORGANISM: Artificial Sequence
<220> FEATURE:
<223> OTHER INFORMATION: Synthesized SEQ ID NO 111

<400> SEQUENCE: 111
taggaagatt cgggtatcgt ttagc                                   25

<210> SEQ ID NO 112
<211> LENGTH: 29
<212> TYPE: DNA
<213> ORGANISM: Artificial Sequence
<220> FEATURE:
<223> OTHER INFORMATION: Synthesized SEQ ID NO 112

<400> SEQUENCE: 112
```
gctacccaaa ctataaatac gaataaacg                                    29

<210> SEQ ID NO 113
<211> LENGTH: 30
<212> TYPE: DNA
<213> ORGANISM: Artificial Sequence
<220> FEATURE:
<223> OTHER INFORMATION: Synthesized SEQ ID NO 113

<400> SEQUENCE: 113
ccacttaata aatttctcta acacgaatcg                                   30

<210> SEQ ID NO 114
<211> LENGTH: 21
<212> TYPE: DNA
<213> ORGANISM: Artificial Sequence
<220> FEATURE:
<223> OTHER INFORMATION: Synthesized SEQ ID NO 114

<400> SEQUENCE: 114
cgtcgggttt tagggttttc g                                            21

<210> SEQ ID NO 115
<211> LENGTH: 20
<212> TYPE: DNA
<213> ORGANISM: Artificial Sequence
<220> FEATURE:
<223> OTHER INFORMATION: Synthesized SEQ ID NO 115

<400> SEQUENCE: 115
tcggagtggg gtaggtgtcg                                              20

<210> SEQ ID NO 116
<211> LENGTH: 22
<212> TYPE: DNA
<213> ORGANISM: Artificial Sequence
<220> FEATURE:
<223> OTHER INFORMATION: Synthesized SEQ ID NO 116

<400> SEQUENCE: 116
cggtggtgta ttacgagggt ta                                           22

<210> SEQ ID NO 117
<211> LENGTH: 27
<212> TYPE: DNA
<213> ORGANISM: Artificial Sequence
<220> FEATURE:
<223> OTHER INFORMATION: Synthesized SEQ ID NO 117

<400> SEQUENCE: 117
aatctaccgt ctatatttcg ataaccg                                      27

<210> SEQ ID NO 118
<211> LENGTH: 21
<212> TYPE: DNA
<213> ORGANISM: Artificial Sequence
<220> FEATURE:
<223> OTHER INFORMATION: Synthesized SEQ ID NO 118

<400> SEQUENCE: 118
ttttcgcgtt ttcgttttcg c                                            21

<210> SEQ ID NO 119
<211> LENGTH: 22
<212> TYPE: DNA

```
<213> ORGANISM: Artificial Sequence
<220> FEATURE:
<223> OTHER INFORMATION: Synthesized SEQ ID NO 119

<400> SEQUENCE: 119
tggagagggg ttattcgttt cg                                      22

<210> SEQ ID NO 120
<211> LENGTH: 24
<212> TYPE: DNA
<213> ORGANISM: Artificial Sequence
<220> FEATURE:
<223> OTHER INFORMATION: Synthesized SEQ ID NO 120

<400> SEQUENCE: 120
tagtagttgt aggaagcgga ttcg                                    24

<210> SEQ ID NO 121
<211> LENGTH: 21
<212> TYPE: DNA
<213> ORGANISM: Artificial Sequence
<220> FEATURE:
<223> OTHER INFORMATION: Synthesized SEQ ID NO 121

<400> SEQUENCE: 121
cgacaaaacg ttcaaccgca a                                       21

<210> SEQ ID NO 122
<211> LENGTH: 25
<212> TYPE: DNA
<213> ORGANISM: Artificial Sequence
<220> FEATURE:
<223> OTHER INFORMATION: Synthesized SEQ ID NO 122

<400> SEQUENCE: 122
ctactacgaa cgacgctact actcc                                   25

<210> SEQ ID NO 123
<211> LENGTH: 22
<212> TYPE: DNA
<213> ORGANISM: Artificial Sequence
<220> FEATURE:
<223> OTHER INFORMATION: Synthesized SEQ ID NO 123

<400> SEQUENCE: 123
cggtggggta ttaaaaggga ag                                      22

<210> SEQ ID NO 124
<211> LENGTH: 25
<212> TYPE: DNA
<213> ORGANISM: Artificial Sequence
<220> FEATURE:
<223> OTHER INFORMATION: Synthesized SEQ ID NO 124

<400> SEQUENCE: 124
aaatctaaat aaatcgcaac gaacg                                   25

<210> SEQ ID NO 125
<211> LENGTH: 15
<212> TYPE: DNA
<213> ORGANISM: Artificial Sequence
<220> FEATURE:
<223> OTHER INFORMATION: Synthesized SEQ ID NO 125

<400> SEQUENCE: 125
gcgctcctcc gacga                                              15
```

<210> SEQ ID NO 126
<211> LENGTH: 20
<212> TYPE: DNA
<213> ORGANISM: Artificial Sequence
<220> FEATURE:
<223> OTHER INFORMATION: Synthesized SEQ ID NO 126

<400> SEQUENCE: 126
ttgaggttcg cgggtaattg                                          20

<210> SEQ ID NO 127
<211> LENGTH: 20
<212> TYPE: DNA
<213> ORGANISM: Artificial Sequence
<220> FEATURE:
<223> OTHER INFORMATION: Synthesized SEQ ID NO 127

<400> SEQUENCE: 127
aaacttttac cccgccaacc                                          20

<210> SEQ ID NO 128
<211> LENGTH: 18
<212> TYPE: DNA
<213> ORGANISM: Artificial Sequence
<220> FEATURE:
<223> OTHER INFORMATION: Synthesized SEQ ID NO 128

<400> SEQUENCE: 128
atcccaaacc cgcacgat                                            18

<210> SEQ ID NO 129
<211> LENGTH: 19
<212> TYPE: DNA
<213> ORGANISM: Artificial Sequence
<220> FEATURE:
<223> OTHER INFORMATION: Synthesized SEQ ID NO 129

<400> SEQUENCE: 129
agattgcgcg gagtttacg                                           19

<210> SEQ ID NO 130
<211> LENGTH: 23
<212> TYPE: DNA
<213> ORGANISM: Artificial Sequence
<220> FEATURE:
<223> OTHER INFORMATION: Synthesized SEQ ID NO 130

<400> SEQUENCE: 130
cactccgaat aaaactacca ccg                                      23

<210> SEQ ID NO 131
<211> LENGTH: 23
<212> TYPE: DNA
<213> ORGANISM: Artificial Sequence
<220> FEATURE:
<223> OTHER INFORMATION: Synthesized SEQ ID NO 131

<400> SEQUENCE: 131
aaataactcg aattccccaa ccg                                      23

<210> SEQ ID NO 132
<211> LENGTH: 29
<212> TYPE: DNA
<213> ORGANISM: Artificial Sequence
<220> FEATURE:

<223> OTHER INFORMATION: Synthesized SEQ ID NO 132

<400> SEQUENCE: 132
ggagagaaag ttttatttgt agtagtcga                                                29

<210> SEQ ID NO 133
<211> LENGTH: 28
<212> TYPE: DNA
<213> ORGANISM: Artificial Sequence
<220> FEATURE:
<223> OTHER INFORMATION: Synthesized SEQ ID NO 133

<400> SEQUENCE: 133
cgacgatccg cctaaacgac taaatccg                                                 28

<210> SEQ ID NO 134
<211> LENGTH: 30
<212> TYPE: DNA
<213> ORGANISM: Artificial Sequence
<220> FEATURE:
<223> OTHER INFORMATION: Synthesized SEQ ID NO 134

<400> SEQUENCE: 134
cgtaactccg actaaaactc gaccgactcg                                               30

<210> SEQ ID NO 135
<211> LENGTH: 29
<212> TYPE: DNA
<213> ORGANISM: Artificial Sequence
<220> FEATURE:
<223> OTHER INFORMATION: Synthesized SEQ ID NO 135

<400> SEQUENCE: 135
tcccttaatc cccgtcaatt atcatcccg                                                29

<210> SEQ ID NO 136
<211> LENGTH: 28
<212> TYPE: DNA
<213> ORGANISM: Artificial Sequence
<220> FEATURE:
<223> OTHER INFORMATION: Synthesized SEQ ID NO 136

<400> SEQUENCE: 136
cgctctactc tccgcccaaa ctaaacca                                                 28

<210> SEQ ID NO 137
<211> LENGTH: 29
<212> TYPE: DNA
<213> ORGANISM: Artificial Sequence
<220> FEATURE:
<223> OTHER INFORMATION: Synthesized SEQ ID NO 137

<400> SEQUENCE: 137
acctctaccc accgtaccgc gtctacttc                                                29

<210> SEQ ID NO 138
<211> LENGTH: 27
<212> TYPE: DNA
<213> ORGANISM: Artificial Sequence
<220> FEATURE:
<223> OTHER INFORMATION: Synthesized SEQ ID NO 138

<400> SEQUENCE: 138
cgacaactac gacgacgacg acgacaa                                                  27

```
<210> SEQ ID NO 139
<211> LENGTH: 25
<212> TYPE: DNA
<213> ORGANISM: Artificial Sequence
<220> FEATURE:
<223> OTHER INFORMATION: Synthesized SEQ ID NO 139

<400> SEQUENCE: 139
ccgaaaccga aaccgaaacc gaacc                                    25

<210> SEQ ID NO 140
<211> LENGTH: 25
<212> TYPE: DNA
<213> ORGANISM: Artificial Sequence
<220> FEATURE:
<223> OTHER INFORMATION: Synthesized SEQ ID NO 140

<400> SEQUENCE: 140
cgacccgaat cccgcaaacc aaacc                                    25

<210> SEQ ID NO 141
<211> LENGTH: 25
<212> TYPE: DNA
<213> ORGANISM: Artificial Sequence
<220> FEATURE:
<223> OTHER INFORMATION: Synthesized SEQ ID NO 141

<400> SEQUENCE: 141
aatccctcaa ccgcctccac gaacc                                    25

<210> SEQ ID NO 142
<211> LENGTH: 28
<212> TYPE: DNA
<213> ORGANISM: Artificial Sequence
<220> FEATURE:
<223> OTHER INFORMATION: Synthesized SEQ ID NO 142

<400> SEQUENCE: 142
ctcaattccc ctccgaaact cctttccg                                 28

<210> SEQ ID NO 143
<211> LENGTH: 24
<212> TYPE: DNA
<213> ORGANISM: Artificial Sequence
<220> FEATURE:
<223> OTHER INFORMATION: Synthesized SEQ ID NO 143

<400> SEQUENCE: 143
cacgcatatc cgcatccacg cgaa                                     24

<210> SEQ ID NO 144
<211> LENGTH: 29
<212> TYPE: DNA
<213> ORGANISM: Artificial Sequence
<220> FEATURE:
<223> OTHER INFORMATION: Synthesized SEQ ID NO 144

<400> SEQUENCE: 144
tcctaataac ctccgaccga cgaacgaca                                29

<210> SEQ ID NO 145
<211> LENGTH: 29
<212> TYPE: DNA
<213> ORGANISM: Artificial Sequence
<220> FEATURE:
<223> OTHER INFORMATION: Synthesized SEQ ID NO 145
```

<400> SEQUENCE: 145
ttaatcacac gccgctacaa atcaccgaa                             29

<210> SEQ ID NO 146
<211> LENGTH: 30
<212> TYPE: DNA
<213> ORGANISM: Artificial Sequence
<220> FEATURE:
<223> OTHER INFORMATION: Synthesized SEQ ID NO 146

<400> SEQUENCE: 146
cgcgacgaaa ctcaaatacg atatacaacg                            30

<210> SEQ ID NO 147
<211> LENGTH: 19
<212> TYPE: DNA
<213> ORGANISM: Artificial Sequence
<220> FEATURE:
<223> OTHER INFORMATION: Synthesized SEQ ID NO 147

<400> SEQUENCE: 147
acgcgcccca acgcactcc                                        19

<210> SEQ ID NO 148
<211> LENGTH: 23
<212> TYPE: DNA
<213> ORGANISM: Artificial Sequence
<220> FEATURE:
<223> OTHER INFORMATION: Synthesized SEQ ID NO 148

<400> SEQUENCE: 148
cgcacccttc taacgactcc cgc                                   23

<210> SEQ ID NO 149
<211> LENGTH: 27
<212> TYPE: DNA
<213> ORGANISM: Artificial Sequence
<220> FEATURE:
<223> OTHER INFORMATION: Synthesized SEQ ID NO 149

<400> SEQUENCE: 149
cgctactcca acgaccgcta ccttaaa                               27

<210> SEQ ID NO 150
<211> LENGTH: 27
<212> TYPE: DNA
<213> ORGANISM: Artificial Sequence
<220> FEATURE:
<223> OTHER INFORMATION: Synthesized SEQ ID NO 150

<400> SEQUENCE: 150
cttcgcccga taccaaccca aatacgc                               27

<210> SEQ ID NO 151
<211> LENGTH: 23
<212> TYPE: DNA
<213> ORGANISM: Artificial Sequence
<220> FEATURE:
<223> OTHER INFORMATION: Synthesized SEQ ID NO 151

<400> SEQUENCE: 151
gcacatcccc gacttccccg aac                                   23

<210> SEQ ID NO 152
<211> LENGTH: 30

<212> TYPE: DNA
<213> ORGANISM: Artificial Sequence
<220> FEATURE:
<223> OTHER INFORMATION: Synthesized SEQ ID NO 152

<400> SEQUENCE: 152
tctcctccga ccgcttccta aactacgcta                              30

<210> SEQ ID NO 153
<211> LENGTH: 30
<212> TYPE: DNA
<213> ORGANISM: Artificial Sequence
<220> FEATURE:
<223> OTHER INFORMATION: Synthesized SEQ ID NO 153

<400> SEQUENCE: 153
aaaaccaccc gaaacaactc aacaacaaaa                              30

<210> SEQ ID NO 154
<211> LENGTH: 25
<212> TYPE: DNA
<213> ORGANISM: Artificial Sequence
<220> FEATURE:
<223> OTHER INFORMATION: Synthesized SEQ ID NO 154

<400> SEQUENCE: 154
aatactcccg ccgtcccatt accga                                   25

<210> SEQ ID NO 155
<211> LENGTH: 25
<212> TYPE: DNA
<213> ORGANISM: Artificial Sequence
<220> FEATURE:
<223> OTHER INFORMATION: Synthesized SEQ ID NO 155

<400> SEQUENCE: 155
ttgtgcgtat atatcgttat ttgcg                                   25

<210> SEQ ID NO 156
<211> LENGTH: 25
<212> TYPE: DNA
<213> ORGANISM: Artificial Sequence
<220> FEATURE:
<223> OTHER INFORMATION: Synthesized SEQ ID NO 156

<400> SEQUENCE: 156
gtttaggttg taggtgcggg tggac                                   25

<210> SEQ ID NO 157
<211> LENGTH: 22
<212> TYPE: DNA
<213> ORGANISM: Artificial Sequence
<220> FEATURE:
<223> OTHER INFORMATION: Synthesized SEQ ID NO 157

<400> SEQUENCE: 157
tcgaacggtt tttatttttc gt                                      22

<210> SEQ ID NO 158
<211> LENGTH: 21
<212> TYPE: DNA
<213> ORGANISM: Artificial Sequence
<220> FEATURE:
<223> OTHER INFORMATION: Synthesized SEQ ID NO 158

<400> SEQUENCE: 158

```
ttcgtcgagg aggaggagta c                                        21

<210> SEQ ID NO 159
<211> LENGTH: 24
<212> TYPE: DNA
<213> ORGANISM: Artificial Sequence
<220> FEATURE:
<223> OTHER INFORMATION: Synthesized SEQ ID NO 159

<400> SEQUENCE: 159
atagcgtttt tcgtaggttg ggga                                     24

<210> SEQ ID NO 160
<211> LENGTH: 19
<212> TYPE: DNA
<213> ORGANISM: Artificial Sequence
<220> FEATURE:
<223> OTHER INFORMATION: Synthesized SEQ ID NO 160

<400> SEQUENCE: 160
tatggttgta gcggttggc                                           19

<210> SEQ ID NO 161
<211> LENGTH: 25
<212> TYPE: DNA
<213> ORGANISM: Artificial Sequence
<220> FEATURE:
<223> OTHER INFORMATION: Synthesized SEQ ID NO 161

<400> SEQUENCE: 161
tttatcgttt gtgtttcggt aatcg                                    25

<210> SEQ ID NO 162
<211> LENGTH: 20
<212> TYPE: DNA
<213> ORGANISM: Artificial Sequence
<220> FEATURE:
<223> OTHER INFORMATION: Synthesized SEQ ID NO 162

<400> SEQUENCE: 162
ggagtaggag gggtgtttcg                                          20

<210> SEQ ID NO 163
<211> LENGTH: 19
<212> TYPE: DNA
<213> ORGANISM: Artificial Sequence
<220> FEATURE:
<223> OTHER INFORMATION: Synthesized SEQ ID NO 163

<400> SEQUENCE: 163
cgggcgggtt ggaagtggg                                           19

<210> SEQ ID NO 164
<211> LENGTH: 24
<212> TYPE: DNA
<213> ORGANISM: Artificial Sequence
<220> FEATURE:
<223> OTHER INFORMATION: Synthesized SEQ ID NO 164

<400> SEQUENCE: 164
cgttgttttt tcgaacgtgt ttgg                                     24

<210> SEQ ID NO 165
<211> LENGTH: 24
<212> TYPE: DNA
<213> ORGANISM: Artificial Sequence
```

```
<220> FEATURE:
<223> OTHER INFORMATION: Synthesized SEQ ID NO 165

<400> SEQUENCE: 165
cgataaaacg tttaatcgta attt                                            24

<210> SEQ ID NO 166
<211> LENGTH: 21
<212> TYPE: DNA
<213> ORGANISM: Artificial Sequence
<220> FEATURE:
<223> OTHER INFORMATION: Synthesized SEQ ID NO 166

<400> SEQUENCE: 166
ttattgcggg cggcgttgtt g                                               21

<210> SEQ ID NO 167
<211> LENGTH: 25
<212> TYPE: DNA
<213> ORGANISM: Artificial Sequence
<220> FEATURE:
<223> OTHER INFORMATION: Synthesized SEQ ID NO 167

<400> SEQUENCE: 167
tacgatagtt gtggaagatt aatta                                           25

<210> SEQ ID NO 168
<211> LENGTH: 23
<212> TYPE: DNA
<213> ORGANISM: Artificial Sequence
<220> FEATURE:
<223> OTHER INFORMATION: Synthesized SEQ ID NO 168

<400> SEQUENCE: 168
ggtttgaatg ggtcgtagcg agc                                             23

<210> SEQ ID NO 169
<211> LENGTH: 19
<212> TYPE: DNA
<213> ORGANISM: Artificial Sequence
<220> FEATURE:
<223> OTHER INFORMATION: Synthesized SEQ ID NO 169

<400> SEQUENCE: 169 cgcgttttt cggcgggtt                                                   19

<210> SEQ ID NO 170
<211> LENGTH: 27
<212> TYPE: DNA
<213> ORGANISM: Artificial Sequence
<220> FEATURE:
<223> OTHER INFORMATION: Synthesized SEQ ID NO 170

<400> SEQUENCE: 170
tttattttgt tatacgtagt tcgtatt                                         27

<210> SEQ ID NO 171
<211> LENGTH: 21
<212> TYPE: DNA
<213> ORGANISM: Artificial Sequence
<220> FEATURE:
<223> OTHER INFORMATION: Synthesized SEQ ID NO 171

<400> SEQUENCE: 171
gtttttattt cgttagtttc g                                               21
```

<210> SEQ ID NO 172
<211> LENGTH: 22
<212> TYPE: DNA
<213> ORGANISM: Artificial Sequence
<220> FEATURE:
<223> OTHER INFORMATION: Synthesized SEQ ID NO 172

<400> SEQUENCE: 172
tttagattcg tacgattttt cg                                              22

<210> SEQ ID NO 173
<211> LENGTH: 22
<212> TYPE: DNA
<213> ORGANISM: Artificial Sequence
<220> FEATURE:
<223> OTHER INFORMATION: Synthesized SEQ ID NO 173

<400> SEQUENCE: 173
tacggtttac gcgtatattt tc                                              22

<210> SEQ ID NO 174
<211> LENGTH: 20
<212> TYPE: DNA
<213> ORGANISM: Artificial Sequence
<220> FEATURE:
<223> OTHER INFORMATION: Synthesized SEQ ID NO 174

<400> SEQUENCE: 174
tcggatgggg ttgttatcgc                                                 20

<210> SEQ ID NO 175
<211> LENGTH: 22
<212> TYPE: DNA
<213> ORGANISM: Artificial Sequence
<220> FEATURE:
<223> OTHER INFORMATION: Synthesized SEQ ID NO 175

<400> SEQUENCE: 175
gaatggttcg gatttttag tc                                               22

<210> SEQ ID NO 176
<211> LENGTH: 25
<212> TYPE: DNA
<213> ORGANISM: Artificial Sequence
<220> FEATURE:
<223> OTHER INFORMATION: Synthesized SEQ ID NO 176

<400> SEQUENCE: 176
ttttagaatc gcgttttttt aaatg                                           25

<210> SEQ ID NO 177
<211> LENGTH: 26
<212> TYPE: DNA
<213> ORGANISM: Artificial Sequence
<220> FEATURE:
<223> OTHER INFORMATION: Synthesized SEQ ID NO 177

<400> SEQUENCE: 177
gaacaccgtt caacgcatta acttcg                                          26

<210> SEQ ID NO 178
<211> LENGTH: 21
<212> TYPE: DNA
<213> ORGANISM: Artificial Sequence
<220> FEATURE:
<223> OTHER INFORMATION: Synthesized SEQ ID NO 178

```
<400> SEQUENCE: 178
tattcgacga cccgaacacc g                                        21

<210> SEQ ID NO 179
<211> LENGTH: 28
<212> TYPE: DNA
<213> ORGANISM: Artificial Sequence
<220> FEATURE:
<223> OTHER INFORMATION: Synthesized SEQ ID NO 179

<400> SEQUENCE: 179
aacgaaaatc aaaaaattac ccattcta                                 28

<210> SEQ ID NO 180
<211> LENGTH: 24
<212> TYPE: DNA
<213> ORGANISM: Artificial Sequence
<220> FEATURE:
<223> OTHER INFORMATION: Synthesized SEQ ID NO 180

<400> SEQUENCE: 180
ccaacctaaa cgaaaaacaa aacg                                     24

<210> SEQ ID NO 181
<211> LENGTH: 25
<212> TYPE: DNA
<213> ORGANISM: Artificial Sequence
<220> FEATURE:
<223> OTHER INFORMATION: Synthesized SEQ ID NO 181

<400> SEQUENCE: 181
cgaaataaaa caaatatcga aacta                                    25

<210> SEQ ID NO 182
<211> LENGTH: 26
<212> TYPE: DNA
<213> ORGANISM: Artificial Sequence
<220> FEATURE:
<223> OTHER INFORMATION: Synthesized SEQ ID NO 182

<400> SEQUENCE: 182
cgataataca ccacgaaaac tacccg                                   26

<210> SEQ ID NO 183
<211> LENGTH: 23
<212> TYPE: DNA
<213> ORGANISM: Artificial Sequence
<220> FEATURE:
<223> OTHER INFORMATION: Synthesized SEQ ID NO 183

<400> SEQUENCE: 183
cgaaaactaa atactaaccc gaa                                      23

<210> SEQ ID NO 184
<211> LENGTH: 18
<212> TYPE: DNA
<213> ORGANISM: Artificial Sequence
<220> FEATURE:
<223> OTHER INFORMATION: Synthesized SEQ ID NO 184

<400> SEQUENCE: 184
ccgcgttccg acctaacc                                            18

<210> SEQ ID NO 185
```

```
<210> SEQ ID NO 185
<211> LENGTH: 18
<212> TYPE: DNA
<213> ORGANISM: Artificial Sequence
<220> FEATURE:
<223> OTHER INFORMATION: Synthesized SEQ ID NO 185

<400> SEQUENCE: 185
tcatccgccc cgaaaccg                                                 18

<210> SEQ ID NO 186
<211> LENGTH: 22
<212> TYPE: DNA
<213> ORGANISM: Artificial Sequence
<220> FEATURE:
<223> OTHER INFORMATION: Synthesized SEQ ID NO 186

<400> SEQUENCE: 186
acaacaacta caaaaaacga ac                                            22

<210> SEQ ID NO 187
<211> LENGTH: 23
<212> TYPE: DNA
<213> ORGANISM: Artificial Sequence
<220> FEATURE:
<223> OTHER INFORMATION: Synthesized SEQ ID NO 187

<400> SEQUENCE: 187
tatcgtaaaa ttcgtaaacg aaa                                           23

<210> SEQ ID NO 188
<211> LENGTH: 22
<212> TYPE: DNA
<213> ORGANISM: Artificial Sequence
<220> FEATURE:
<223> OTHER INFORMATION: Synthesized SEQ ID NO 188

<400> SEQUENCE: 188
aaccgtatcc cgctccgaaa ac                                            22

<210> SEQ ID NO 189
<211> LENGTH: 24
<212> TYPE: DNA
<213> ORGANISM: Artificial Sequence
<220> FEATURE:
<223> OTHER INFORMATION: Synthesized SEQ ID NO 189

<400> SEQUENCE: 189
cgaccttccc gataaaacac caaa                                          24

<210> SEQ ID NO 190
<211> LENGTH: 26
<212> TYPE: DNA
<213> ORGANISM: Artificial Sequence
<220> FEATURE:
<223> OTHER INFORMATION: Synthesized SEQ ID NO 190

<400> SEQUENCE: 190
cgacaacgtc caactcccgc acctcg                                        26

<210> SEQ ID NO 191
<211> LENGTH: 25
<212> TYPE: DNA
<213> ORGANISM: Artificial Sequence
<220> FEATURE:
<223> OTHER INFORMATION: Synthesized SEQ ID NO 191

<400> SEQUENCE: 191
``` ctcgattta ctccacgcct accga                                          25

<210> SEQ ID NO 192
<211> LENGTH: 25
<212> TYPE: DNA
<213> ORGANISM: Artificial Sequence
<220> FEATURE:
<223> OTHER INFORMATION: Synthesized SEQ ID NO 192

<400> SEQUENCE: 192
cgtatctaaa actcgcgaac aacta                                         25

<210> SEQ ID NO 193
<211> LENGTH: 28
<212> TYPE: DNA
<213> ORGANISM: Artificial Sequence
<220> FEATURE:
<223> OTHER INFORMATION: Synthesized SEQ ID NO 193

<400> SEQUENCE: 193
tcgacaataa ccaccacatc taattctc                                      28

<210> SEQ ID NO 194
<211> LENGTH: 17
<212> TYPE: DNA
<213> ORGANISM: Artificial Sequence
<220> FEATURE:
<223> OTHER INFORMATION: Synthesized SEQ ID NO 194

<400> SEQUENCE: 194
gcgaccaccg cccgttc                                                  17

<210> SEQ ID NO 195
<211> LENGTH: 22
<212> TYPE: DNA
<213> ORGANISM: Artificial Sequence
<220> FEATURE:
<223> OTHER INFORMATION: Synthesized SEQ ID NO 195

<400> SEQUENCE: 195
aaattacgcg aaacccacgc ga                                            22

<210> SEQ ID NO 196
<211> LENGTH: 19
<212> TYPE: DNA
<213> ORGANISM: Artificial Sequence
<220> FEATURE:
<223> OTHER INFORMATION: Synthesized SEQ ID NO 196

<400> SEQUENCE: 196
gtacgaacaa cgcccccga                                                19

<210> SEQ ID NO 197
<211> LENGTH: 23
<212> TYPE: DNA
<213> ORGANISM: Artificial Sequence
<220> FEATURE:
<223> OTHER INFORMATION: Synthesized SEQ ID NO 197

<400> SEQUENCE: 197
actaatccgt atcctacata tta                                           23

<210> SEQ ID NO 198
<211> LENGTH: 25
<212> TYPE: DNA

```
<213> ORGANISM: Artificial Sequence
<220> FEATURE:
<223> OTHER INFORMATION: Synthesized SEQ ID NO 198

<400> SEQUENCE: 198
aaatcctatc tacaacaacc gaata                                        25

<210> SEQ ID NO 199
<211> LENGTH: 27
<212> TYPE: DNA
<213> ORGANISM: Artificial Sequence
<220> FEATURE:
<223> OTHER INFORMATION: Synthesized SEQ ID NO 199

<400> SEQUENCE: 199
gaacccaacc gcccaaacga atcgccg                                      27

<210> SEQ ID NO 200
<211> LENGTH: 29
<212> TYPE: DNA
<213> ORGANISM: Artificial Sequence
<220> FEATURE:
<223> OTHER INFORMATION: Synthesized SEQ ID NO 200

<400> SEQUENCE: 200
gaaccgaccg aactccaacc gaaactacg                                    29

<210> SEQ ID NO 201
<211> LENGTH: 24
<212> TYPE: DNA
<213> ORGANISM: Artificial Sequence
<220> FEATURE:
<223> OTHER INFORMATION: Synthesized SEQ ID NO 201

<400> SEQUENCE: 201
ctataaaaac cgattcgtac caaa                                         24

<210> SEQ ID NO 202
<211> LENGTH: 14
<212> TYPE: DNA
<213> ORGANISM: Artificial Sequence
<220> FEATURE:
<223> OTHER INFORMATION: Synthesized SEQ ID NO 202

<400> SEQUENCE: 202
cgcgacctcg aacc                                                    14

<210> SEQ ID NO 203
<211> LENGTH: 24
<212> TYPE: DNA
<213> ORGANISM: Artificial Sequence
<220> FEATURE:
<223> OTHER INFORMATION: Synthesized SEQ ID NO 203

<400> SEQUENCE: 203
aaacaaacgc gatacgataa acaa                                         24

<210> SEQ ID NO 204
<211> LENGTH: 22
<212> TYPE: DNA
<213> ORGANISM: Artificial Sequence
<220> FEATURE:
<223> OTHER INFORMATION: Synthesized SEQ ID NO 204

<400> SEQUENCE: 204
gccgccgccg caactaccgc cg                                           22
```

<210> SEQ ID NO 205
<211> LENGTH: 27
<212> TYPE: DNA
<213> ORGANISM: Artificial Sequence
<220> FEATURE:
<223> OTHER INFORMATION: Synthesized SEQ ID NO 205

<400> SEQUENCE: 205
gacctcgacc tcgacctcga ccttcga                                        27

<210> SEQ ID NO 206
<211> LENGTH: 25
<212> TYPE: DNA
<213> ORGANISM: Artificial Sequence
<220> FEATURE:
<223> OTHER INFORMATION: Synthesized SEQ ID NO 206

<400> SEQUENCE: 206
acgaaattcg aaccgaaaca actac                                          25

<210> SEQ ID NO 207
<211> LENGTH: 30
<212> TYPE: DNA
<213> ORGANISM: Artificial Sequence
<220> FEATURE:
<223> OTHER INFORMATION: Synthesized SEQ ID NO 207

<400> SEQUENCE: 207
cgtaaacgcg aaaccgaccc gtaaaaacga                                     30

<210> SEQ ID NO 208
<211> LENGTH: 21
<212> TYPE: DNA
<213> ORGANISM: Artificial Sequence
<220> FEATURE:
<223> OTHER INFORMATION: Synthesized SEQ ID NO 208

<400> SEQUENCE: 208
cgacgaaaaa aaaccccgaa a                                              21

<210> SEQ ID NO 209
<211> LENGTH: 29
<212> TYPE: DNA
<213> ORGANISM: Artificial Sequence
<220> FEATURE:
<223> OTHER INFORMATION: Synthesized SEQ ID NO 209

<400> SEQUENCE: 209
cgtttaatac gtatattcgt atttacgcg                                      29

<210> SEQ ID NO 210
<211> LENGTH: 30
<212> TYPE: DNA
<213> ORGANISM: Artificial Sequence
<220> FEATURE:
<223> OTHER INFORMATION: Synthesized SEQ ID NO 210

<400> SEQUENCE: 210
cgccgaaacc catctaccgc tcgccgaccg                                     30

<210> SEQ ID NO 211
<211> LENGTH: 32
<212> TYPE: DNA
<213> ORGANISM: Artificial Sequence
<220> FEATURE:

```
<223> OTHER INFORMATION: Synthesized SEQ ID NO 211

<400> SEQUENCE: 211
cgtcgttgta agttatcggg tcgttagggg tc                                    32

<210> SEQ ID NO 212
<211> LENGTH: 29
<212> TYPE: DNA
<213> ORGANISM: Artificial Sequence
<220> FEATURE:
<223> OTHER INFORMATION: Synthesized SEQ ID NO 212

<400> SEQUENCE: 212
cgcacctaaa ccccgccgcg accgcatcg                                        29

<210> SEQ ID NO 213
<211> LENGTH: 25
<212> TYPE: DNA
<213> ORGANISM: Artificial Sequence
<220> FEATURE:
<223> OTHER INFORMATION: Synthesized SEQ ID NO 213

<400> SEQUENCE: 213
caacgaaata cgctaaaacg cgcca                                            25

<210> SEQ ID NO 214
<211> LENGTH: 28
<212> TYPE: DNA
<213> ORGANISM: Artificial Sequence
<220> FEATURE:
<223> OTHER INFORMATION: Synthesized SEQ ID NO 214

<400> SEQUENCE: 214
tctaaattaa cctcgcgaaa accgccaa                                         28

<210> SEQ ID NO 215
<211> LENGTH: 32
<212> TYPE: DNA
<213> ORGANISM: Artificial Sequence
<220> FEATURE:
<223> OTHER INFORMATION: Synthesized SEQ ID NO 215

<400> SEQUENCE: 215
gttttagcgg tcgttgtttt agaaaagtta ac                                    32

<210> SEQ ID NO 216
<211> LENGTH: 25
<212> TYPE: DNA
<213> ORGANISM: Artificial Sequence
<220> FEATURE:
<223> OTHER INFORMATION: Synthesized SEQ ID NO 216

<400> SEQUENCE: 216
ccgcgcgcat ctaaactaac accga                                            25

<210> SEQ ID NO 217
<211> LENGTH: 27
<212> TYPE: DNA
<213> ORGANISM: Artificial Sequence
<220> FEATURE:
<223> OTHER INFORMATION: Synthesized SEQ ID NO 217

<400> SEQUENCE: 217
aaacgccgaa aacaacgaaa ctcttaa                                          27
```

```
<210> SEQ ID NO 218
<211> LENGTH: 27
<212> TYPE: DNA
<213> ORGANISM: Artificial Sequence
<220> FEATURE:
<223> OTHER INFORMATION: Synthesized SEQ ID NO 218

<400> SEQUENCE: 218
cctaacgcaa cccaaaaaac gatcgaa                                           27

<210> SEQ ID NO 219
<211> LENGTH: 27
<212> TYPE: DNA
<213> ORGANISM: Artificial Sequence
<220> FEATURE:
<223> OTHER INFORMATION: Synthesized SEQ ID NO 219

<400> SEQUENCE: 219
actaaactat cccgaataac ttcaccg                                           27

<210> SEQ ID NO 220
<211> LENGTH: 27
<212> TYPE: DNA
<213> ORGANISM: Artificial Sequence
<220> FEATURE:
<223> OTHER INFORMATION: Synthesized SEQ ID NO 220

<400> SEQUENCE: 220
tccccattcc gataataaaa cgacgaa                                           27

<210> SEQ ID NO 221
<211> LENGTH: 24
<212> TYPE: DNA
<213> ORGANISM: Artificial Sequence
<220> FEATURE:
<223> OTHER INFORMATION: Synthesized SEQ ID NO 221

<400> SEQUENCE: 221
gtgatggagg aggtttagta agtt                                              24

<210> SEQ ID NO 222
<211> LENGTH: 25
<212> TYPE: DNA
<213> ORGANISM: Artificial Sequence
<220> FEATURE:
<223> OTHER INFORMATION: Synthesized SEQ ID NO 222

<400> SEQUENCE: 222
ccaataaaac ctactcctcc cttaa                                             25

<210> SEQ ID NO 223
<211> LENGTH: 30
<212> TYPE: DNA
<213> ORGANISM: Artificial Sequence
<220> FEATURE:
<223> OTHER INFORMATION: Synthesized SEQ ID NO 223

<400> SEQUENCE: 223
accaccaccc aacacacaat aacaaacaca                                        30
```

COMBINATIONS, DETECTION METHODS AND KITS OF DNA METHYLATION BIOMARKER

CROSS-REFERENCE TO RELATED APPLICATIONS

This application is a continuation-in-part of PCT Patent Application No. PCT/CN2020/072770, filed Jan. 17, 2020, which claims the benefit of Chinese Patent Application No: 2019113673854, filed Dec. 26, 2019, all of which are incorporated by reference herein in their entirety. This application also claims the priority benefit of Chinese Patent Application No. 2020105062103, filed Jun. 5, 2020, which is also incorporated herein by reference in its entirety.

FIELD OF THE INVENTION

The present invention is directed to a combination of the DNA methylation biomarkers, and methods for using the same.

BACKGROUND OF THE INVENTION

Bladder cancer (BC) is the tenth most common cancer worldwide and the ninth leading cause of cancer death in men. It is also the most common malignant tumors in the urinary system. Bladder cancer is characterized with the high morbidity and high rate of recurrence. A common clinical symptom of bladder cancer is hematuria, which occurs in about 17% of bladder cancer patients. At present, clinical tests for bladder cancer mainly include cystoscopy, urine exfoliative cytology, urinary Fish test, and tumor marker detection. While cystoscopy followed by biopsy histopathology is the gold standard for the diagnosis of bladder cancer, this detection method is invasive, prone to complications, resulting in low patient compliance. The imaging examination has a limited ability for the diagnosis of a small lesion, the urine exfoliative cytology has a low sensitivity, and the urinary FISH test is complex in operation and is subjective in the interpretation of result. The tumor marker detection test is mainly based on the presence of specific proteins in urine. Unfortunately, due to a low amount of the proteins present in urine, the tumor marker detection test has a limited sensitivity and specificity.

The bladder cancer is generally categorized in three different classifications based on histological grading, TNM classification, tumor size and foci. These three bladder cancer classifications consist of (i) low-intermediate-risk non-muscle invasive bladder cancer (LMR-NMIBC), (ii) high-risk NMIBC (HR-NMIBC), and (iii) muscle invasive bladder cancer (MIBC). MIBC is more aggressive with high morbidity and high risk of distant metastases development. Although 70-80% of patients are diagnosed with NMIBC and 50% are LMR-NMIBC that shows favorable prognosis, patients diagnosed with HR-NMIBC have 5-year recurrence of up to 80%, progression of up to 50%, and the survival rate of only 35% once NMIBC progresses to MIBC. Therefore, both NMIBC patients at high-risk and MIBC patients require more intensive treatment and surveillance.

Current standard for diagnosis and surveillance of bladder cancer is cystoscopy or transurethral resection of the bladder tumor (TURBT) followed by biopsy of suspicious lesions. Due to the costly and invasive procedure, the usage of cystoscopy or TURBT for initial diagnosis is sub-optimal. It has been estimated that 20,000 bladder cancer cases are missed annually among moderate-high-risk hematuria patients and nearly 230,000 cases per year underwent highly invasive cystoscopy in patients with near-zero cancer risk in the Unite States (US). On the other hand, determination of BC tumor staging, infiltration, lymph node and metastasis status requires further tests using radiologic imaging including magnetic resonance imaging (MRI), computed tomography (CT), ultrasound, and intravenous urography, in conjunction with post-surgery pathology confirmation. Reports have estimated that up to 41% of NMIBC were understaged at initial TURBT and required second TURBT, possibly due to the tumor heterogeneity and failure of detrusor muscle inclusion. Because of the non-cost-effective usage of diagnostic modalities, in addition to the high demanding follow-ups with HR-NMIBC and MIBC patients of high recurrent rates, diagnosing bladder cancer resulted in significant cumulative costs, the care of which accounts for >3% all cancer-related medical payments.

Therefore, there is a need for a relatively simple non-invasive diagnostic tools with high sensitivity that can facilitate early detection, and/or accurate risk stratifying capacity of bladder cancer. Such a diagnostic tool can facilitate rational diagnostic protocol, reduce intensive treatments from delayed diagnosis, and reduce the risk and the economic burden to the patient.

SUMMARY OF THE INVENTION

Some aspects of the invention are based on the discovery by the present inventors that urine tumor DNA methylation can be used as a non-invasive diagnostic tool to improve bladder cancer detection and preoperative risk stratification. One particular aspect of the invention, provides a biomarker combination for preoperative risk stratification of bladder cancer and a detection method based on urine DNA methylation, which can be used to exclude hematuria patients of near zero cancer risk, avoiding excessive cystoscope, and to identify HR-NMIBC and MIBC patients from those suspected of bladder cancer for expediting diagnosis and surgical modalities. Biomarker combinations and methods of the invention also allow patients with LMR-NMIBC to avoid missed diagnosis can to follow the standard of care.

One particular embodiment of the invention provides a DNA methylation biomarker combination that can be used in risk stratification of bladder cancer. In some embodiments, a combination of DNA methylation markers for bladder cancer detection is selected from any combination of two or more, typically three or more, often four or more, still more often five or more, and most often six or more sequences from SEQ ID NOs:1-22 or a complementary sequences thereof. Throughout this disclosure, co-methylated regions of SEQ ID NOS:1-22 are indicated by brackets, i.e., [CG]. In addition or alternatively, the combination of biomarkers can include two or more of complementary sequences of SEQ ID NOS:1-22. Further, a combination of SEQ ID NOS:2-3, 2-4, 2-5, 2-6, 2-8, 2-9, 2-10, 2-11, 2-12, 2-13, 2-14, 2-15, 2-16, 2-17, 2-19, 2-20, 2-21 or 2-22 DNA methylation markers can also be selected.

In some embodiments, the combination of DNA methylation markers for bladder cancer detection includes a combination of at least two sequences selected from SEQ ID NOS:2, 3, 6, 13-15, 17, or a combination of at least two complementary sequences thereof.

Still in embodiments, the combination of DNA methylation markers for bladder cancer detection comprises SEQ ID NOS:1 and 2 or a combination of complementary sequences thereof.

Yet in other embodiments, the combination of DNA methylation markers for bladder cancer detection comprises SEQ ID NOS:1-3, or a combination of complementary sequences thereof.

In further embodiments, the combination of DNA methylation markers for bladder cancer detection comprises SEQ ID NOS:1-8 or a combination of complementary sequences thereof.

Still in further embodiments, the combination of DNA methylation markers for bladder cancer detection comprises SEQ ID NOS:1-22 or a combination of complementary sequences thereof.

In some of these embodiments, the combination of DNA methylation markers for bladder cancer detection comprises following groups, or a combination of complementary sequences thereof:

| | | | |
|---|---|---|---|
| Combination A | SEQ ID NO: 2 | | SEQ ID NO: 1 |
| Combination B | SEQ ID NO: 17 | SEQ ID NO: 20 | SEQ ID NO: 1 |
| Combination C | SEQ ID NO: 2 | SEQ ID NO: 9 | SEQ ID NO: 8 |
| Combination D | SEQ ID NO: 15 | | SEQ ID NO: 6 |
| Combination E | SEQ ID NO: 3 | SEQ ID NO: 18 | SEQ ID NO: 14 |
| Combination F | SEQ ID NO: 16 | | SEQ ID NO: 12 |
| Combination G | SEQ ID NO: 22 | SEQ ID NO: 5 | SEQ ID NO: 4 |
| Combination H | SEQ ID NO: 13 | SEQ ID NO: 10 | SEQ ID NO: 21 |
| Combination I | SEQ ID NO: 19 | SEQ ID NO: 11 | SEQ ID NO: 7 |
| Combination K | SEQ ID NO: 2 | | SEQ ID NO: 6 |
| Combination L | SEQ ID NO: 3 | | SEQ ID NO: 4 |

Another aspect of the invention provides use of any of the combination of DNA biomarkers disclosed herein for detection, diagnosis, classification, prediction, treatment monitoring, prognosis or otherwise evaluating for bladder cancer.

Still another aspect of the invention provides a kit for bladder cancer detection, wherein the kit comprises any of the combination of DNA biomarkers disclosed herein. The kit can be used for diagnosis, monitoring, concomitant diagnosis, analysis, rating, treatment and the like for a patient with bladder cancer.

In one particular embodiment, the kit for identifying bladder cancer at different grades or stages comprises a reagent for detecting a co-methylation level in a co-methylated region indicated by [CG] in a combination of DNA methylation markers of at least two of SEQ ID NO:2, SEQ ID NO:3, SEQ ID NO:5, SEQ ID NO:6, SEQ ID NO:13, SEQ ID NO:14, SEQ ID NO:15, SEQ ID NO:16, SEQ ID NO:17, SEQ ID NO:18, SEQ ID NO:21, and SEQ ID NO:22, or a co-methylation level of a combination of complementary sequences thereof.

In some embodiments, the combination of DNA methylation markers for bladder cancer detection comprises SEQ ID NO:6, SEQ ID NO:13, SEQ ID NO:16, and SEQ ID NO:18 or a combination of complementary sequences thereof.

Still in other embodiments, the combination of DNA methylation markers for bladder cancer detection comprises SEQ ID NO:6, SEQ ID NO:10, SEQ ID NO:13, SEQ ID NO:16, and SEQ ID NO:18 or a combination of complementary sequences thereof.

Yet in other embodiments, the combinations of DNA methylation markers for bladder cancer detection comprises SEQ ID NO:17 and SEQ ID NO:13 or complementary sequences thereof.

In further embodiments, the combination of DNA methylation markers comprises SEQ ID NO:17, SEQ ID NO:13, and SEQ ID NO:5, or a combination of complementary sequences thereof, or a combination of SEQ ID NO:17, SEQ ID NO:13 and SEQ ID NO:22 or a combination of the complementary sequences thereof.

Further aspects of the invention provide a kit for diagnosing bladder cancer. In one embodiment, the kit comprises a reagent to detect methylation level of the combination of any of the DNA methylation markers disclosed herein. In some embodiments, the amplification primers and fluorescent probes are used to detect each methylated region of any of the DNA methylation markers disclosed herein.

When fluorescence quantitative PCR is used, the kit can also include amplification primers and fluorescent probes for each methylated region. In one particular embodiment, the amplification primers and fluorescent probes are selected from the group consisting of:

SEQ ID NO:23, SEQ ID NO:45 and SEQ ID NO:67 for SEQ ID NO:1;
SEQ ID NO:24, SEQ ID NO:46 and SEQ ID NO:68 for SEQ ID NO:2;
SEQ ID NO:25, SEQ ID NO:47 and SEQ ID NO:69 for SEQ ID NO:3;
SEQ ID NO:26, SEQ ID NO:48 and SEQ ID NO:70 for SEQ ID NO:4;
SEQ ID NO:27, SEQ ID NO:49 and SEQ ID NO:71 for SEQ ID NO:5;
SEQ ID NO:28, SEQ ID NO:50 and SEQ ID NO:72 for SEQ ID NO:6;
SEQ ID NO:29, SEQ ID NO:51 and SEQ ID NO:73 for SEQ ID NO:7;
SEQ ID NO:30, SEQ ID NO:52 and SEQ ID NO:74 for SEQ ID NO:8;
SEQ ID NO:31, SEQ ID NO:53 and SEQ ID NO:75 for SEQ ID NO:9;
SEQ ID NO:32, SEQ ID NO:54 and SEQ ID NO:76 for SEQ ID NO:10;
SEQ ID NO:33, SEQ ID NO:55 and SEQ ID NO:77 for SEQ ID NO:11;
SEQ ID NO:34, SEQ ID NO:56 and SEQ ID NO:78 for SEQ ID NO:12;
SEQ ID NO:35, SEQ ID NO:57 and SEQ ID NO:79 for SEQ ID NO:13;
SEQ ID NO:36, SEQ ID NO:58 and SEQ ID NO:80 for SEQ ID NO:14;
SEQ ID NO:37, SEQ ID NO:59 and SEQ ID NO:81 for SEQ ID NO:15;
SEQ ID NO:38, SEQ ID NO:60 and SEQ ID NO:82 for SEQ ID NO:16;
SEQ ID NO:39, SEQ ID NO:61 and SEQ ID NO:83 for SEQ ID NO:17;
SEQ ID NO:40, SEQ ID NO:62 and SEQ ID NO:84 for SEQ ID NO:18;
SEQ ID NO:41, SEQ ID NO:63 and SEQ ID NO:85 for SEQ ID NO:19;
SEQ ID NO:42, SEQ ID NO:64 and SEQ ID NO:86 for SEQ ID NO:20;
SEQ ID NO:43, SEQ ID NO:65 and SEQ ID NO:87 for SEQ ID NO:21;
SEQ ID NO:44, SEQ ID NO:66 and SEQ ID NO:88 for SEQ ID NO:22; and
primers and probes having a plurality of consecutive nucleotides which are at least 70%, 80%, 90%, 95%, or 99% identical to the above sequences.

In some embodiments, when fluorescence quantitative PCR is used, the kit for bladder cancer detection comprises amplification primers and fluorescent probes selected from the group consisting of:
SEQ ID NO:89, SEQ ID NO:111 and SEQ ID NO:133 for SEQ ID NO:1;

SEQ ID NO:90, SEQ ID NO:112 and SEQ ID NO:134 for SEQ ID NO:2;
SEQ ID NO:91, SEQ ID NO:113 and SEQ ID NO:135 for SEQ ID NO:3;
SEQ ID NO:92, SEQ ID NO:114 and SEQ ID NO:136 for SEQ ID NO:4;
SEQ ID NO:93, SEQ ID NO:115 and SEQ ID NO:137 for SEQ ID NO:5;
SEQ ID NO:94, SEQ ID NO:116 and SEQ ID NO:138 for SEQ ID NO:6;
SEQ ID NO:95, SEQ ID NO:117 and SEQ ID NO:139 for SEQ ID NO:7;
SEQ ID NO:96, SEQ ID NO:118 and SEQ ID NO:140 for SEQ ID NO:8;
SEQ ID NO:97, SEQ ID NO:119 and SEQ ID NO:141 for SEQ ID NO:9;
SEQ ID NO:98, SEQ ID NO:120 and SEQ ID NO:142 for SEQ ID NO:10;
SEQ ID NO:99, SEQ ID NO:121 and SEQ ID NO:143 for SEQ ID NO:11;
SEQ ID NO:100, SEQ ID NO:122 and SEQ ID NO:144 for SEQ ID NO:12;
SEQ ID NO:101, SEQ ID NO:123 and SEQ ID NO:145 for SEQ ID NO:13;
SEQ ID NO:101, SEQ ID NO:124 and SEQ ID NO:146 for SEQ ID NO:14;
SEQ ID NO:103, SEQ ID NO:125 and SEQ ID NO:147 for SEQ ID NO:15;
SEQ ID NO:104, SEQ ID NO:126 and SEQ ID NO:148 for SEQ ID NO:16;
SEQ ID NO:105, SEQ ID NO:127 and SEQ ID NO:149 for SEQ ID NO:17;
SEQ ID NO:106, SEQ ID NO:128 and SEQ ID NO:150 for SEQ ID NO:18;
SEQ ID NO:107, SEQ ID NO:129 and SEQ ID NO:151 for SEQ ID NO:19;
SEQ ID NO:108, SEQ ID NO:130 and SEQ ID NO:152 for SEQ ID NO:20;
SEQ ID NO:109, SEQ ID NO:131 and SEQ ID NO:153 for SEQ ID NO:21;
SEQ ID NO:110, SEQ ID NO:132 and SEQ ID NO:154 for SEQ ID NO:22; and
primers and probes having a plurality of consecutive nucleotides which are at least 70%, 80%, 90%, 95%, or 99% identical to the above sequences.

In some embodiments, when fluorescence quantitative PCR is used, the kit for bladder cancer detection comprises amplification primers and fluorescent probes selected from the group consisting of:
SEQ ID NO:155, SEQ ID NO:177 and SEQ ID NO:199 for SEQ ID NO:1;
SEQ ID NO:156, SEQ ID NO:178 and SEQ ID NO:200 for SEQ ID NO:2;
SEQ ID NO:157, SEQ ID NO:179 and SEQ ID NO:201 for SEQ ID NO:3;
SEQ ID NO:158, SEQ ID NO:180 and SEQ ID NO:202 for SEQ ID NO:4;
SEQ ID NO:159, SEQ ID NO:181 and SEQ ID NO:203 for SEQ ID NO:5;
SEQ ID NO:160, SEQ ID NO:182 and SEQ ID NO:204 for SEQ ID NO:6;
SEQ ID NO:161, SEQ ID NO:183 and SEQ ID NO:205 for SEQ ID NO:7;
SEQ ID NO:162, SEQ ID NO:184 and SEQ ID NO:206 for SEQ ID NO:8;
SEQ ID NO:163, SEQ ID NO:185 and SEQ ID NO:207 for SEQ ID NO:9;
SEQ ID NO:164, SEQ ID NO:186 and SEQ ID NO:208 for SEQ ID NO:10;
SEQ ID NO:165, SEQ ID NO:187 and SEQ ID NO:209 for SEQ ID NO:11;
SEQ ID NO:166, SEQ ID NO:188 and SEQ ID NO:210 for SEQ ID NO:12;
SEQ ID NO:167, SEQ ID NO:189 and SEQ ID NO:211 for SEQ ID NO:13;
SEQ ID NO:168, SEQ ID NO:190 and SEQ ID NO:212 for SEQ ID NO:14;
SEQ ID NO:169, SEQ ID NO:191 and SEQ ID NO:213 for SEQ ID NO:15;
SEQ ID NO:170, SEQ ID NO:192 and SEQ ID NO:214 for SEQ ID NO:16;
SEQ ID NO:171, SEQ ID NO:193 and SEQ ID NO:215 for SEQ ID NO:17;
SEQ ID NO:172, SEQ ID NO:194 and SEQ ID NO:216 for SEQ ID NO:18;
SEQ ID NO:173, SEQ ID NO:195 and SEQ ID NO:217 for SEQ ID NO:19;
SEQ ID NO:174, SEQ ID NO:196 and SEQ ID NO:218 for SEQ ID NO:20;
SEQ ID NO:175, SEQ ID NO:197 and SEQ ID NO:219 for SEQ ID NO:21;
SEQ ID NO:176, SEQ ID NO:198 and SEQ ID NO:220 for SEQ ID NO:22; and
primers and probes having a plurality of consecutive nucleotides which are at least 70%, 80%, 90%, 95%, or 99% identical to the above sequences.

Typically, primers and probes are selected according to the combination of specific methylated regions to be detected. In some embodiments, the kit for bladder cancer detection further comprises primers and probes for internal reference gene: SEQ ID NOs:221-223; or primers or probes having a plurality of consecutive nucleotides which are at least 70%, 80%, 90%, 95%, or 99% identical thereto.

Another aspect of the invention provides a method for detecting bladder cancer. The method generally includes:
extracting genomic DNA and/or free DNA from a biological sample to be detected;
performing bisulfite conversion for the DNA;
detecting co-methylation of the above combination of DNA methylation markers of the bisulfite-converted DNA and a control, to obtain a methylation profile, and
comparing the methylation profile of the combination of DNA methylation markers with the identifying threshold of a profile obtained from mathematical modelling based on datasets to identify the presence of bladder cancer in the biological sample.

In some embodiments, co-methylation is determined using, for example, methylation specific PCR, DNA methylation-based chip, targeted DNA methylation sequencing, digital PCR quantitative, fluorescence quantitative PCR, or a combination thereof.

In another aspect, the present invention further provides a method for diagnosing, staging and/or classifying bladder cancer. The method comprises:
extracting genomic DNA and/or free DNA from biological sample to be detected;
performing bisulfite conversion for the DNA;
detecting co-methylation of the above combination of DNA methylation markers for the bisulfite-converted DNA;
comparing a relative number of cycles d-$C_T$ of target DNA methylation marker regions and with a pre-defined threshold, and identifying grade or stage of bladder cancer of the biological sample from different sources.

Yet in another aspect, the present invention provides a method for predicting, treatment monitoring, determining prognosis of and/or evaluating bladder cancer. The method comprises:
obtaining DNA from a biological sample of a subject;
performing bisulfite conversion of the DNA;
determining co-methylation levels in the biological sample using a plurality of reagents to detect co-methylation levels in any of the DNA methylation markers disclosed herein;
comparing with an identified threshold for co-methylation level obtained from mathematical modelling based on datasets to predict, monitor treatment of, determine prognosis of, and/or evaluate bladder cancer.

In some embodiments of the invention, a combination of co-methylation status of multiple specific methylated regions (e.g., markers) is used to identify the occurrence of bladder cancer. It has been discovered by the present inventors that DNA methylation biomarker combinations disclosed herein are highly sensitive in identifying the occurrence of bladder cancer. The detection method is fast and simple. The present inventor found that the selected combination of the multiple methylated regions has superior performance in identifying the occurrence of bladder cancer compared to methods that use co-methylation state of a single methylated region.

The combination of the pairs of primers and probes disclosed herein allows for simultaneous detection and determination of co-methylation levels of multiple methylated regions. In terms of primer sequence designs, the combination of pairs of primers of the kit overcomes mismatch problems that may occur in a single site detection method and thus significantly reduces false positive amplification. Furthermore, primer pairs disclosed herein take into account of the interactions between combinations of primers and probes for the multiple methylation biomarkers. The multiple fluorescence quantitative PCR system of the kit disclosed herein results in a high amplification efficiency and a significantly improved sensitivity in detecting bladder cancer.

In some embodiments of the invention, the DNA methylation biomarker combination comprises SEQ ID NO:3 or its complementary sequence, SEQ ID NO:5 or its complementary sequence, and SEQ ID NO:7 or its complementary sequence, where [CG] indicates co-methylated regions. Unless otherwise stated or the context requires otherwise, the term "complementary sequence" refers to a complete, i.e., 100%, complementary sequence.

In some embodiments, the combination further includes the co-methylated regions indicated by [CG] of SEQ ID NO:1 or its complementary sequence.

In some embodiments, the combination further includes the co-methylated regions indicated by [CG] of SEQ ID NO:2 or its complementary sequence.

In some optimized embodiments, the combination further includes the co-methylated regions indicated by [CG] of SEQ ID NO:1 or its complementary sequence, and SEQ ID NO:2 or its complementary sequence.

In some optimized embodiments, said DNA methylation biomarkers combination for bladder cancer risk stratification includes SEQ ID NO:3, SEQ ID NO:5, SEQ ID NO:7, SEQ ID NO:1 and SEQ ID NO:2.

The present invention further provides the detection application of said DNA methylation biomarkers combination in risk stratification of bladder cancer.

The present invention further provides a kit for risk stratifying of bladder cancer.

Another aspect of the invention provides a kit for bladder cancer risk stratification comprising any of the above-mentioned DNA methylation markers combinations and a reagent to detect methylation levels.

In one of the embodiments, when fluorescence quantitative PCR is used, the detection kit includes amplification primers and fluorescent probes for each methylated region, said amplification primers and fluorescent probes being selected from:
SEQ ID NO:25, SEQ ID NO:47 and SEQ ID NO:69 for target region of SEQ ID NO:3,
SEQ ID NO:27, SEQ ID NO:49 and SEQ ID NO:71 for target region of SEQ ID NO:5, and
SEQ ID NO:29, SEQ ID NO:51 and SEQ ID NO:73 for target region of SEQ ID NO:7; or
primers and probes having a plurality of consecutive nucleotides which are at least 70%, 80%, 90%, 95%, or 99% identical to the above sequences.

Still in other embodiments, when fluorescence quantitative PCR is used, the detection kit includes amplification primers and fluorescent probes for a single methylated region, said amplification primers and fluorescent probes being selected from:
SEQ ID NO:91, SEQ ID NO:113 and SEQ ID NO:135 for target region of SEQ ID NO:3,
SEQ ID NO:93, SEQ ID NO:115 and SEQ ID NO:137 for target region of SEQ ID NO:5, and
SEQ ID NO:95, SEQ ID NO:117 and SEQ ID NO:139 for target region of SEQ ID NO:7; or
primers and probes having a plurality of consecutive nucleotides which are at least 70%, 80%, 90%, 95%, or 99% identical to the above sequences.

Yet in other embodiments, when fluorescence quantitative PCR is used, the detection kit includes amplification primers and fluorescent probes for a single methylated region, said amplification primers and fluorescent probes being selected from:
SEQ ID NO:157, SEQ ID NO:179 and SEQ ID NO:201 for target region of SEQ ID NO:3;
SEQ ID NO:159, SEQ ID NO:181 and SEQ ID NO:203 for target region of SEQ ID NO:5; and
SEQ ID NO:161, SEQ ID NO:183 and SEQ ID NO:205 for target region of SEQ ID NO:7; or
primers and probes having a plurality of consecutive nucleotides which are at least 70%, 80%, 90%, 95%, or 99% identical to the above sequences.

Still in further embodiments, the amplification primers and fluorescent probes for target region of SEQ ID NO:1 further includes:
SEQ ID NO:23, SEQ ID NO:45 and SEQ ID NO:67;
SEQ ID NO:89, SEQ ID NO:111 and SEQ ID NO:133;
SEQ ID NO:155, SEQ ID NO:177 and SEQ ID NO:199; or
primers and probes having a plurality of consecutive nucleotides which are at least 70%, 80%, 90%, 95%, or 99% identical to the above sequences.

In other embodiments, the amplification primers and fluorescent probes for target region of SEQ ID NO:2 further includes:

SEQ ID NO:24, SEQ ID NO:46 and SEQ ID NO:68;
SEQ ID NO:90, SEQ ID NO:112 and SEQ ID NO:134;
SEQ ID NO:156, SEQ ID NO:178 and SEQ ID NO:200; or primers and probes having a plurality of consecutive nucleotides which are at least 70%, 80%, 90%, 95%, or 99% identical to the above sequences.

In further embodiments, the kit also includes primers and probes for internal reference genes: SEQ ID NOS:221-223 or primers and probes having a plurality of consecutive nucleotides which are at least 70%, 80%, 90%, 95%, or 99% identical to the above sequences.

Another aspect of the invention provides a method for detecting methylated regions for bladder cancer risk stratification. In general, the method includes:

extracting genomic DNA and/or cell-free DNA from a biological sample to be detected;
performing bisulfite treatment for the DNA;
detecting co-methylation of the above-mentioned DNA methylation markers combination on the bisulfite-treated DNA and a control to obtain a methylation profile,
comparing the methylation profile of the combination of DNA methylation markers with cut-offs of a profile obtained from mathematical modelling based on datasets to identify the presence of and the risk stratification of bladder cancer in the biological sample.

In some of the embodiments, the method herein for co-methylation detection includes: methylation specific PCR, DNA methylation-based chip, targeted DNA methylation sequencing, digital PCR, and fluorescence quantitative PCR.

In another aspect, the present invention further provides a method for diagnosing, staging and classifying bladder cancer.

A method for diagnosing, staging and classifying bladder cancer, wherein the method includes the following steps:

extracting genomic DNA and/or cell-free DNA from a biological sample to be detected;
performing bisulfite treatment for the DNA;
detecting co-methylation of the above DNA methylation markers combination on the bisulfite-treated DNA to obtain the relative cycle thresholds (d-$C_T$) of the target DNA methylation marker region;
comparing the relative cycle thresholds (d-$C_T$) of target DNA methylation marker regions with pre-defined cut-offs;
stratifying grade or stage of bladder cancer of the biological sample from different sources.

In another aspect, the present invention further provides a method for predicting, treatment monitoring, prognosis or otherwise evaluation of bladder cancer, wherein the method includes the following steps:

obtaining a biological sample from an individual;
extracting genomic DNA and/or cell-free DNA from the biological sample;
performing bisulfite treatment for the DNA;
contacting the bisulfite-treated DNA with a plurality of reagents that specifically detect co-methylation levels of the above DNA methylation markers to measure the co-methylation levels of the DNA methylation markers of the biological sample;
comparing with cut-offs for co-methylation level obtained from mathematical modelling based on datasets to predict bladder cancer, monitor treatment, or provide prognosis of bladder cancer.

The present invention characterized a number of specific methylation region candidates (biomarker candidates) for bladder cancer risk stratification and finds that DNA methylation marker combination (SEQ ID NO:3, SEQ ID NO:5, SEQ ID NO:7) is superior for bladder cancer risk stratification. In particular, the three-class stratification model of the five-DNA methylation marker-combination (SEQ ID NO:3, SEQ ID NO:5, SEQ ID NO:7, SEQ ID NO:1 and SEQ ID NO:2) identified HR-NMIBC and MIBC with 82.1% sensitivity, 90.0% specificity and 88.6% positive predictive value (PPV).

The high PPV enables accurate prediction of HR-NMIBC and MIBC for expediting diagnosis and treatment agenda. In addition, the three-class stratification model of the marker combination identified non-BC patients with 84.7 sensitivity, 87.2% specificity and 79.1% negative predictive value (NPV). The high NPV could effectively exclude non-BC patients from excessive cystoscopy. Furthermore, the high NPV of 93.1% for LMR-NMIBC group, and 83.3% for HR-NMIBC or MIBC group also ensured that these patients can be avoided from being missed diagnosis.

BRIEF DESCRIPTION OF THE DRAWINGS

FIG. 8 shows predictive performance features of five-marker combinations on risk stratification in Cohort 2.

FIG. 9 is a table showing comparison of $C_T$ values of positive controls measured by multiplex fluorescent quantitative PCR with single plex fluorescent quantitative PCR.

DETAILED DESCRIPTION OF THE INVENTION

Figure 1:
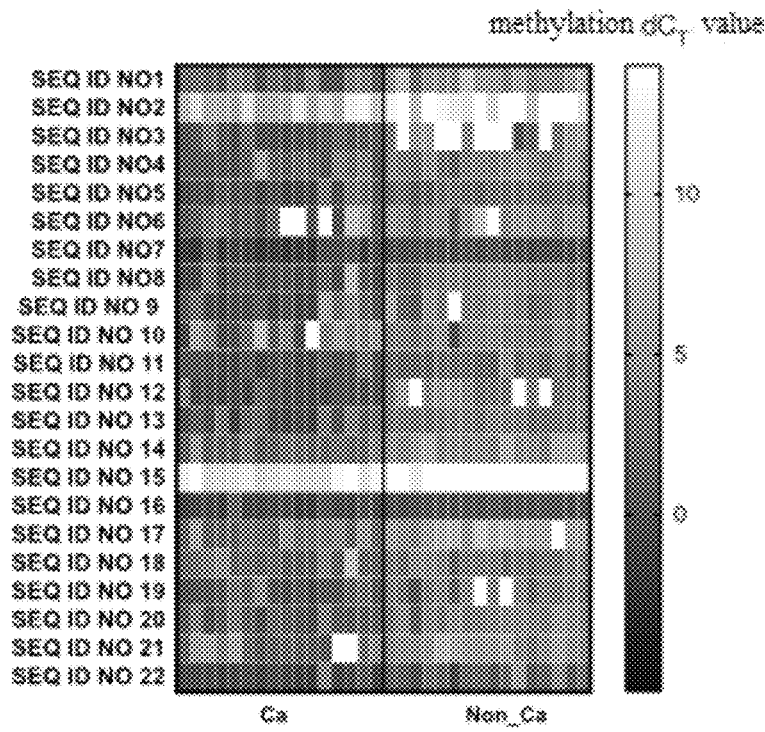
FIG. 1: Heat map of differences in co-methylation of multiple DNA methylated regions between bladder cancer and normal tissues.

In order to facilitate the understanding of the present disclosure, a more comprehensive description about the present disclosure is given below. The present disclosure can be implemented in many different forms, and is not limited to the embodiments described herein. On the contrary, some of the purposes of providing these embodiments are to merely illustrate the scope of the invention and to make the understanding of the disclosure more thorough and comprehensive.

The following embodiments, which may not include specific conditions, can be readily performed in accordance with conventional conditions, such as those described in Sambrook et al., Molecular Cloning: Laboratory Manual (New York: Cold Spring Harbor Laboratory Press, 1989), or those as recommended by the manufacturer. The various common chemical reagents used in the embodiments are commercially available.

Unless otherwise defined, all technical and scientific terms used in the present disclosure are the same as understood by those skilled in the technical field of the present disclosure. The terms used in the specification of the present disclosure are for the purpose of describing specific embodiments only and it is not intended to limit the present disclosure. The term "and/or" used in the present disclosure includes any and all combinations of one or more related items listed.

It should be appreciated that various embodiments of the present invention disclosed herein may be readily combined without departing from the scope or the spirit of the present invention.

Definitions: To facilitate understanding of the present invention, a number of terms and phrases are defined below.

The term "or" is an inclusive "or" operator and is equivalent to the term "and/or", unless the context clearly dictates otherwise. The term "based on" is not exclusive and allowed for being based on additional factors not described, unless the context clearly dictates otherwise. In addition, the singular forms "a," "an" and "the" include plural references unless the content clearly dictates otherwise. The meaning of "in . . . " includes "within . . . " and "on . . . ".

The terms "complementary" and "complementarity" refer to nucleotides (e.g., a nucleotide) or a polynucleotide (e.g., a sequence of nucleotide) associated with base pairing rule. For Example, sequence 5'-A-G-T-3' is complementary to sequence 3'-T-C-A-5'. Complementary can be "partial," in which only some nucleic acid bases are matched according to the base pairing rule. Alternatively, there may be "completely" or "total" complementarity between nucleic acids. The complementary degree between nucleic acid chains affects the efficiency and strength of hybridization between nucleic acid chains. This is especially important in the amplification reactions and detection methods that depend upon binding between nucleic acids.

The term "polymerase chain reaction" or "PCR" is used to refer to a technique for amplifying a target sequence and is well recognized by one skilled in the art. The PCR generally consists of: introducing a large excess of two oligonucleotide primers into the DNA mixture containing the desired target sequence, followed by a precise sequence of thermal cycling in the presence of a DNA polymerase. The two primers are complementary to their respective strands of the double stranded target sequence. For amplification, the mixture is denatured and then the primers annealed with its complementary sequence within the target molecule. After annealing, the primers were extended with a polymerase so as to form a new pair of complementary chains. The steps of denaturation, primer annealing, and polymerase extension can be repeated many times (that is, denaturation, annealing, and extension constitute one "cycle" and there can be numerous "cycles") to obtain a high concentration of amplified fragments of the desired target sequence. The length of the amplified fragment of the target sequence is determined by the relative position of the primers with respect to each other, so the length is a controllable parameter. Since the desired amplified fragment of the target sequence becomes the predominant sequence (in terms of concentration) in the mixture, it is called "PCR amplified", "PCR products" or "amplicons".

The term "nucleic acid detection assay" refers to any method of determining the nucleotide composition of the target nucleic acid. Nucleic acid detection assay includes but is not limited to DNA sequencing methods and probe hybridization methods.

The term "amplifiable nucleic acid" refers to a nucleic acid that can be amplified by any amplification method. It is expected that "amplifiable nucleic acid" will normally comprise "sample template".

The term "sample template" refers to the nucleic acid originating from a sample that is for analysis of presence of the "target" (as defined below). In contrast, "background template" is used to refer to nucleic acids other than the sample template, which may be or may not be present in the sample. Background template is most often inadvertent, which may be the result of carryover, or due to the presence of nucleic acid contaminants sought to be purified from the sample. For Example, nucleic acids from an organism other than those to be tested may exist as a background for the test sample.

The term "primer" refers to an oligonucleotide, whether occurring naturally as in a purified restriction digestion or is produced synthetically, that is capable of acting as a point of initiation of synthesis when placed in the conditions for induction of synthesis of product extended from primers complementary to nucleic acid chain (e.g., in the presence of nucleotides and an inducing agent such as a DNA polymerase and under proper temperature and pH). The primer is typically single-stranded for maximum efficiency in amplification, but may alternatively be double-stranded. In the case of double chains, the primer is first treated to separate its strands before being used to prepare the extension product. In general, the primer is oligodeoxyribonucleotides. At minimum, the length of primer should be sufficient to initiate the synthesis of the extension product in the presence of the inducer. The exact length of the primer will depend on many factors, including temperature, source of the primer, and the use of the method.

The term "probe" refers to an oligonucleotide (e.g., a sequence of nucleotides) whether occurring naturally as in a purified restriction digest or produced synthetically, recombinantly, or by PCR amplification, that is capable of selectively hybridize to another sensitive target oligonucleotide. A probe can be single-stranded or double-stranded. Probes are useful in the detection, identification, and isolation of specific gene sequences (e.g., "capture probes"). It is anticipated that in some embodiments, any probe used in the present invention may be labelled with any "report molecule" to make it detectable in any detection system.

The term "methylation" refers to cytosine methylation at position C5 or N4 of cytosines, the N6 position of adenine, or other types of nucleic acid methylation. In vitro DNA amplified oligonucleotides are usually unmethylated because typical in vitro DNA amplification methods do not retain the methylation pattern of the amplified template. However, "unmethylated DNA" or "methylated DNA" can also refer to amplified DNA whose original template was unmethylated or methylated, respectively.

The term "methylated nucleotides" or "methylated nucleotide bases" refers to the presence of a methyl moiety on a nucleotide base, where the methyl moiety is not present in a recognized typical nucleotide bases. For Example, cytosine does not contain a methyl moiety in its pyrimidine ring, but 5-methyl cytosine contains a methyl moiety at 5-position of its pyrimidine ring. Therefore, cytosine is not a methylated nucleotide and 5-methylcytosine is a methylated nucleotide. In another example, the thymine contains a methyl moiety at 5-position of its pyrimidine ring; however, for the purposes herein, thymine is not considered a methylated nucleotide when present in DNA since thymine is a typical nucleotide base of DNA.

The methylation status can be optionally represented or indicated by a "methylation value" (e.g., representing methylation frequency, fraction, ration, percent, etc.). A methylation values can be generated, for example, by quantifying the amount of intact nucleic acid present following restriction digestion with a methylation dependent restriction enzyme, by comparing amplification profiles after the bisulfite reaction, or by comparing the sequences of bisulfite-treated and untreated nucleic acids. Thus, a value such as methylation value, represents methylation status and can be used as quantitative indicator of methylation status across multiple copies of a locus. The level of co-methylation is indicated or shown by the methylation status of more than one methylation site, and it is defined as co-methylation when more than one methylation site is methylated within a methylated region.

As used herein, the term "bisulfite reagent" refers to a reagent comprising bisulphite, disulphite, hydrogen sulfite or a combination thereof. Cytosine nucleotides without methylation in the DNA treated with a bisulfite reagent will convert or translate into uracil, methylated cytosine while other bases remain unchanged. This allows differentiation between the methylated and unmethylated cytidine such as those in two nucleotide sequence of CpG.

The term "methylation assay" refers to any assay used to determine the methylation status of one or more CpG dinucleotide sequences within a nucleic acid sequence.

Risk stratification is based on the progressiveness, prognosis and recurrence of bladder cancer. The subject is risk-stratified into three groups: non-BC group, LMR-NMIBC group, and high-risk bladder cancer group. For LMR-NMIBC, diagnosis of NMIBC was confirmed by pathology diagnosis. The high-risk bladder cancer groups (HR-MIBC and MIBC) includes high-risk NMIBC and MIBC, in which muscle invasiveness was confirmed by pathology. In general, the criteria for risk stratification of NMIBC is based on the guideline of the National Comprehensive Cancer Network ("NCCN").

One aspect of the invention provides a combination of oligonucleotides that can be used to stratify, determine, diagnose, or otherwise evaluate the presence of bladder cancer. These oligonucleotides can also be used to monitor treatment of bladder cancer. In some embodiment, a combination of oligonucleotides disclosed herein are used to determine the level of methylation in a combination of methylation regions in a genome of an individual with bladder cancer. These combinations of genome regions have a significantly higher methylation level in a subject with bladder cancer relative to the methylation level in a subject without bladder cancer. As shown in FIG. 1, the co-methylation levels of these methylated regions are sensitive and specific to reflect the occurrence of bladder cancer.

Another aspect of the invention provides using a combination of oligonucleotides disclosed herein to determine the level of methylation in two or more methylated regions for diagnosis of the occurrence of bladder cancer. Such a diagnosis can be performed using a fluid sample or a cell sample (e.g., a biopsy sample) from the subjected to be tested. In one particular embodiment, the sample is a urine sample obtained from the subject. Consistent with the results of tissue samples, the co-methylation levels in a combination of methylation regions are higher in the DNA obtained from a urine sample of a patient with bladder cancer, compared to the DNA obtained from urine sample of normal people (i.e., subjects without bladder cancer). There is a significant difference in these two groups (FIG. 2), which shows that the combination of selected methylated regions in the DNA obtained from urine has a relatively high signal that indicates the presence of bladder cancer, and is highly sensitive in detecting bladder cancer. Since obtaining a urine sample from a subject is non-invasive procedure, testing for bladder cancer using a urine sample will greatly reduce the burden and risk to patients, thereby likely increasing the test compliance.

Another aspect of the invention provides using a combination of oligonucleotides disclosed herein to determine the level of methylation in three or more methylated regions for risk stratification bladder cancer. Such a risk stratification can be performed using a fluid sample or a cell sample (e.g., a biopsy sample) from the subjected to be tested. In one particular embodiment, the sample is a urine sample obtained from the subject. The co-methylation levels of these methylation regions are different among the DNA obtained from urine samples of patients in different risk groups (i.e., Non-BC vs LMR-NMIBC vs HR-NMIBC+MIBC) (FIG. 5), which shows distinct methylation levels between Non-BC and all the BC groups, and furthermore distinct differences between LMR-NMIBC and HR-NMIBC, with the level in HR-NMIBC similar to MIBC. These observations are in concordance with current understanding of HR-NMIBC showing high recurrent and progression rate and poorer survivals, and thus the combination of selected methylated regions in the DNA obtained from urine has an accurate indication on different risk level of bladder cancer.

Detection means for determining co-methylation level can include the use of methylation-specific polymerase chain reaction, nucleic acid sequencing, mass spectrometry, methylation-specific nuclease, mass-based separation or targeted capture.

In one embodiment, the detection of the methylated regions according to the present invention comprises:
  performing bisulfite conversion of the DNA obtained from a biological sample from a subject; and
  detecting or determining co-methylation of multiple methylated regions of the bisulfite-converted DNA.

The DNA used can be extracted genomic DNA and/or free DNA from a biological sample obtained from the subject. In some embodiments, DNA extraction kit is used to obtain the DNA for analysis. Other suitable methods for obtaining genomic DNA and/or free DNA from a subject for testing for the presence of bladder cancer is well known to one skilled in the art.

The method for detecting co-methylation include methylation specific PCR (MSP), DNA methylation-based chip, targeted DNA methylation sequencing, digital PCR and quantitative fluorescence PCR.

In some embodiments, DNA (e.g. genomic DNA, such as extracted genomic DNA or processed genomic DNA) is isolated by any standard means in the field, including the use of commercially available kits.

In other embodiments, the biological sample for obtaining the DNA is a biopsy material. In some cases, the biological sample is a tissue sample. In other cases, the biological sample is a biopsy sample. Still in other cases, the biological sample is a fluid sample obtained from the subject. Exemplary fluid samples that can be used in methods of the invention include, but are not limited to, blood, urine, plasma, saliva, and serum. In some cases, the biological sample is a urine sample, including exfoliated cells in urine, urine sediment, and urine supernatant.

In one particular embodiment, the procedures of MSP detection method include:
1) amplifying the co-methylated fragments in the selected target regions from the bisulfite-converted DNA using a pair of specific primers SEQ ID NOS:23-44;
2) amplifying the non-methylated fragments in the selected target regions from the bisulfite-converted DNA using a pair of specific primers;
3) analyzing the amplified products resulting from the above 1) and 2) by an agar gel electrophoresis; and
4) determining the co-methylation levels of the selected target regions according to the presence or absence of the bands or density of the bands from the electrophoresis result.

In one particular embodiment, the process of DNA methylation-based chip detection includes:
1) amplifying the whole genome from the bisulfite-converted DNA;
2) contacting said bisulfite-converted DNA with a chip comprising co-methylated and non-methylated capture probes to form a target-captured complex when a target region is present in said bisulfite-converted DNA, wherein said co-methylated and non-methylated capture probes comprises SEQ ID NOS:1-22 or nucleic acid sequences that are complementary to SEQ ID NOS:1-22 in a target capture region;
3) performing a labelled single-base elongation reaction of said target-captured complex;
4) amplifying and reading sequence signals captured according to the fluorescent staining reaction, and calculating the methylation levels in the target regions.

Still in another embodiment, the process of target DNA methylation sequencing process includes:
1) amplifying the whole genome from the bisulfite-converted DNA;
2) linking the amplified product in 1) with a linker;
3) targeted-capturing the library building product in 2), wherein the capture probe used is a converted DNA sequence containing SEQ ID NOS:1-22 or reversely and complementarily pairing sequences to SEQ ID NOS:1-22;
4) sequencing of the capture products of 3);
5) calculating the methylation levels in the selected target regions according to the sequencing result.

Yet in another embodiment, the PCR procedure includes:
1) quantifying the co-methylation level in the selected target regions for the bisulfite-converted DNA using a pair of primers and a probe for said selected target regions, wherein said pair of primers and a probe is selected from the group consisting of SEQ ID NOS: 23-220;
2) quantifying the non-methylation level in the selected target regions for the bisulfite-converted DNA using a specific primers and probes; and
3) calculating the methylation rate of each selected target region according to the non-methylation level and the quantification of the co-methylation level in each region.

In further embodiments, a process of fluorescence quantitative PCR is described below.

Another aspect of the invention provides a kit for detecting co-methylation level in the target methylated regions. The design and combination of the pairs of primers and probes play a key role for simultaneous detection of co-methylation levels of multiple methylated regions. In terms of primer sequence design, the combination of pairs of primers of the kit overcomes the shortcoming of false positive due to mismatch in the detection of a single methylation site, and takes into account of the interactions between combinations of pairs of primers for the multiple methylation biomarkers. The multiple fluorescence quantitative PCR system of this kit developed for the reaction components. In some embodiments, up to 23 target fragments can be amplified simultaneously on the premise of ensuring the efficiency of amplifying the target fragments. The multi-fluorescence quantitative PCR reaction solution of this kit can detect the co-methylation level of up to three target regions.

In some embodiments, the kit comprises (i) one of the pairs of primer and probe sets from 3 options of 22 methylated target regions, which sequence is shown in tables 2-1, 2-2, and 2-3; (2) a set of primers and probes for each of the methylated regions of the internal reference gene; and (3) multiple fluorescence quantitative PCR reaction solution of the multiple PCR reaction system.

Other aspects of the invention provides a method for detecting and identifying the co-methylation level of the target methylated regions using a detection kit disclosed herein. This detection method can detect the co-methylation levels of up to 22 methylated regions in parallel and simultaneously, and can also process multiple samples, which has the advantages of high throughput and simple in operation.

In one particular embodiment, the method for detecting and identifying the co-methylation level of the target methylated regions includes:
1) performing a direct fluorescence quantitative PCR reaction with the bisulfite-converted genomic DNA using the primers, probes and reaction reagents; and
2) determining the co-methylation levels of the target regions according to a $C_T$ value after corrected with an internal reference, and calculating the risk score of bladder cancer based on logistic regression.

Figure 3:
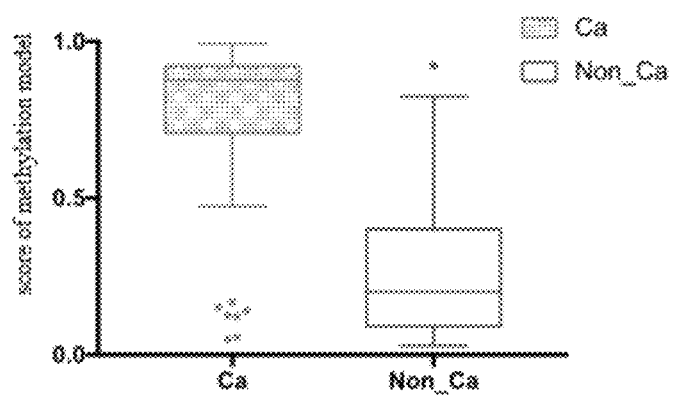
FIG. 3: Bladder cancer risk scores based on DNA co-methylation combinations were significantly different between populations with and without bladder cancer.

Yet another aspect of the invention provides a method for determining the occurrence of bladder cancer (including detection, diagnosis, classification or prediction, treatment monitoring, prognosis or otherwise evaluating bladder cancer) based on the co-methylation level of the methylated regions. The logistic regression equation is fitted according to the co-methylation level of multiple methylated regions of the bladder cancer group and the normal group, then the risk score of bladder cancer is calculated according to the logistic regression equation. There is a significant difference between the score of bladder cancer group and that of the normal group as can be seen in FIG. 3. Thus, the bladder cancer group can be readily distinguished from the normal group. A statistics mathematical formula is used throughout the method of identifying the occurrence of bladder cancer according to the present disclosure, avoiding any subjectivity involving artificial judgment of a result in traditional urine FISH detection. This non-subjective analysis results in a more accurate, stable and reliable interpretation.

Another aspect of the invention provides a method for bladder cancer risk stratification. The method can include the use of methylation-specific polymerase chain reaction, nucleic acid sequencing, mass spectrometry, methylation-specific nuclease, mass-based separation or targeted capture.

A method for bladder cancer risk stratification, wherein the method includes the following steps:
performing bisulfite treatment on a DNA obtained from a biological sample of a subject; and
detecting or determining the level of co-methylation of multiple methylated regions on the bisulfite-treated DNA using a plurality of oligonucleotides disclosed herein.

The method of detecting co-methylation includes methylation specific PCR (MSP), DNA methylation-based chip, targeted DNA methylation sequencing, digital PCR and fluorescence quantitative PCR.

In some embodiments, DNA (e.g. genomic DNA, such as extracted genomic DNA or processed genomic DNA) is isolated by any standard means in the field, including the use of commercially available kits.

In some embodiments, the biological sample to be detected is a biopsy material. In some cases, the biological sample is a tissue sample. In some cases, the biological sample is a biopsy sample. In some cases, the biological sample is a blood sample, including plasma, saliva, and serum. In some cases, the biological sample is a urine sample, including exfoliated cells in urine, urine sediment, and urine supernatant.

Another embodiment of the MSP procedure includes:
1) using specific primers to amplify the target co-methylated regions on the bisulfite-treated DNA;
2) using specific primers to amplify the target non-methylated regions on the bisulfite-treated DNA;
3) performing agar gel electrophoresis analysis on the amplicons resulted from the above 1) and 2); and
4) determining the co-methylation levels of the selected target regions according to the presence or absence of the bands or density of the bands in the electrophoresis results.

One particular process of DNA methylation-based chip detection method includes:
1) Performing whole genome amplification on the bisulfite-treated DNA;
2) Generating probes for hybridization of the co-methylated and non-methylated regions of SEQ ID NOS:1, 2, 3, 5 and 7 or their complementary nucleic acid sequences on the chip;
3) Capturing the targeted regions from the amplicons produced in 1) using immobilized probes on the chip as described in 2), and performing the labelled single nucleotide extension;
4) Amplifying and reading the fluorescent signals from the extension reaction of captured target regions, and
5) Analyzing the methylation levels in the target regions.

Another method of targeted DNA methylation sequencing includes:
1) Performing whole genome amplification on the bisulfite-treated DNA;
2) Performing adaptor and indexing ligation on the said amplicons in 1);
3) Performing targeted-capturing on said library products in 2), wherein the capture probes used are bisulfite treated DNA sequences containing SEQ ID NOS:1, 2, 3, 5 and 7 or their reverse complementary sequences;
4) Performing sequencing on the captured products of 3);
5) Calculating the methylation levels of the target regions based on the sequencing results.

Still another method of digital PCR includes:
1) Performing absolute quantification of the target co-methylated regions with said primer and probes on the bisulfite-treated DNAs;
2) Performing absolute quantification of the target non-methylated regions with specific primer and probes on the bisulfite-treated DNAs; and
3) Calculating the methylation levels of each region based on the absolute qualification of the non-methylated and co-methylated values of the target region.

Additional objects, advantages, and novel features of this invention will become apparent to those skilled in the art upon examination of the following examples thereof, which are not intended to be limiting. In the Examples, procedures that are constructively reduced to practice are described in the present tense, and procedures that have been carried out in the laboratory are set forth in the past tense.

EXAMPLES

The primers herein were purchased from Thermo Fisher (Invitrogen) company, the multiple PCR reaction reagent was purchased from Thermo Fisher company, and the multiple fluorescence quantitative PCR reagent was purchased from Qiagen company or Bio-rad company or Vazyme company.

Example 1

Co-methylation in multiple methylated regions for detection, diagnosis, classification or prediction, treatment monitoring, prognosis or otherwise evaluation of bladder cancer included co-methylation of multiple methylated sites indicated by (CG) in nucleic acid sequence in table 1, as well as co-methylation of multiple methylated sites in a nucleic acid that is complementary in sequence to the nucleic acid indicated by (CG) in table 1.

Example 2

The sequence combination of the five markers for bladder cancer risk stratification is as follows: SEQ ID NO: 1, SEQ ID NO:2, SEQ ID NO:3, SEQ ID NO: 5, and SEQ ID NO:7. In addition to the combination of the above five markers, Table 1 shows a total of 22 nucleotide sequences including other listed biomarkers.

TABLE 1

Co-methylation composition of DNA methylated regions.

| SEQ ID NO | nucleic acid sequence and Co-methylation in multiplex methylation sites indicated by (CG) |
|---|---|
| 1 | TAGGAAGACT[CG]GGCAC[CG]TTCAG[CG]CATTGGCTT[CG][CG]GACCCAGC[CG]CCCAGG[CG]GAT[CG]C[CG]GAAG[CG]CAAGTAG[CG]GTGTGTG[CG]CACAG |

TABLE 1-continued

Co-methylation composition of DNA methylated regions.

| SEQ ID NO | nucleic acid sequence and Co-methylation in multiplex methylation sites indicated by (CG) |
|---|---|
| 2 | ATGTT[CG]G[CG]GCC[CG]GGCAC[CG][CG]AGC[CG]GC[CG]AGCTCCAGC[CG]GAGCTA[CG]TGACTA[CG]TCCACC[CG]CACCTACAGCCTGGGCAGC |
| 3 | TTGG[CG]GTCAAAGTGGCCC[CG]ACT[CG]GGATGACAATTGA[CG]GGGATCAAGGGATTGCCCATTCTGTGCCTGTAAGAAC[CG]ATT[CG]TGCCAGAGAAACTCATCAAGTGG |
| 4 | [CG]C[CG]GGCTCCAGGGCTCC[CG][CG]CTCCAGTGGCCCAGCCTGGG[CG]GAGAGCAGAG[CG][CG]GCCCC[CG][CG]GCCC[CG][CG]GCCT[CG]AGCCC[CG] |
| 5 | CC[CG]GAGTGGGGCAGGTGT[CG]GAGCTGGGTGGGAAGCAGA[CG][CG]GTA[CG]GTGGGCAGAGGTCCCCAGCCTG[CG]GGGAG[CG]CTAT |
| 6 | C[CG]GTGGTGCACCA[CG]AGGGCTACC[CG]TTTGC[CG]C[CG]C[CG]C[CG]C[CG]CAGCTGC[CG]C[CG]C[CG]C[CG]CCAGC[CG]CTGCAGCCATG |
| 7 | [CG]GGAACTGAGTGCTGGCC[CG]GGAGACCCTC[CG]GAGAGCT[CG][CG]GGCT[CG]GCCT[CG]GCCT[CG]GCCT[CG]GCCTT[CG]GC[CG][CG]GTTAC[CG]AAACACAGA[CG]GTAGACT |
| 8 | CTCC[CG][CG]CCCC[CG]CCCC[CG][CG]TTC[CG]GCCTGGCCTG[CG]GGATT[CG]GGC[CG]AGGCAACTGCAGGGA[CG]GGGCACCCCTCCTGCTCC |
| 9 | TGGAGAGGGGTCATC[CG]CCC[CG]GAAC[CG]A[CG]TGAG[CG][CG]GGGC[CG]GCC[CG]TGGAGG[CG]GCTGAGGGATCCCCCACTTCCAGCC[CG]CC[CG] |
| 10 | GCAGCAGCTGCAGGAAG[CG]GACT[CG]G[CG]GAAAGGAGCCC[CG]GAGGGGAACTGAGTGCCTTCAGCCAGGCA[CG]TT[CG]GGGAGACAG[CG] |
| 11 | TGC[CG]CAAAATT[CG]CAGA[CG]AAGGGCTTGTAGCC[CG][CG]TGGATG[CG]GATATG[CG]TGTTGAG[CG]TGGAGCTG[CG]GTTGAA[CG]CTTTGC[CG] |
| 12 | TGCTACCCCAGC[CG]TGTCC[CG]CTC[CG]GAGACCCCAGGG[CG]C[CG]GGACCCATCTGC[CG]CT[CG]C[CG]GC[CG]GAGGCTACCAGGAGCAGGAGCAGCAG[CG]C[CG]CC[CG]CAGTAG |
| 13 | [CG]GCCTTC[CG]GTGGGGCACCAAAAGGGAAGCCTCCT[CG]GCCCCTGG[CG]ACC[CG]GTGACTTGCAG[CG]G[CG]TGTGATTAATCTTCCACAGCTGT[CG]TGCCCCATCCACTTGAG |
| 14 | GCAAC[CG]GCAG[CG]TCCAGCTCC[CG]CACCT[CG]CTGCACAT[CG]CACCTGAGCCC[CG]C[CG][CG]AC[CG]CAT[CG][CG]CT[CG]CTG[CG]ACCCATTCAGACCC |
| 15 | CTTCAGCTGCCCT[CG]ATTTTGCTCCA[CG]CCTGC[CG]GCCAGAGCCTCC[CG]G[CG]TTTCTTC[CG]CCCCAG[CG]GAGTG[CG]CTGGGG[CG][CG]CCAGGGCTAGGCC[CG]C[CG]GAGGAG[CG][CG]TC |
| 16 | [CG]TGTCTGAGGCT[CG][CG]GGCAACTGGAACTGAGAGTCTGAGTTGGCCT[CG][CG]GGAGC[CG]CCAGAAGGGTG[CG]GGCTG[CG]TGTGGCAGAGTAGGAGCACTGT |
| 17 | T[CG]GCAGTGGCCACCACATCTGGTTCT[CG]TTAACTTTTCTAAGGCAG[CG]GC[CG]CTGGAGCAG[CG]GGGCTGG[CG]GGGTAAAAGCTC |
| 18 | [CG][CG]GCCAC[CG]CC[CG]TTCATCACC[CG][CG][CG]CATCTGGGCTGGCAC[CG]GG[CG]AAGAAT[CG]TG[CG]GGTCTGGGAC |
| 19 | AGATTG[CG][CG]GAGCCCA[CG][CG]ATCCCTGGGA[CG]C[CG]GAGACAA[CG]GGGCTCTTGGGAAGG[CG][CG]GAGCC[CG]GGGAAGC[CG]GGGATGTG[CG][CG]TGAGC[CG]TGCC[CG]CAGGGTC |
| 20 | GGAG[CG]TG[CG]GGCAG[CG]CCCC[CG]AACCCTAG[CG]CAGCCCAGGAAG[CG]GT[CG]GAGGAGACTGTCCTGGC[CG][CG]GTGGCAGCCCCATC[CG]GAGTG |
| 21 | AAAACTGATC[CG]TGTCCTGCATGTTGGCAGCAGACAACCTTCCTTGCTGCTGAGCTGTCC[CG]GGTGGCTTCAC[CG][CG]GCTGGGGAATC[CG]AGCCATTCC |
| 22 | GGAGAGAAAGTCCTATCTGCAGCAGC[CG]AATGGTCCCCATTC[CG]GTAATGGGA[CG]G[CG]GGAGCATTTGGGAGGA[CG][CG]ATTCTAAAGAGAG[CG] |

Example 3

A co-methylation test kit for detection, diagnosis, classification, stratification or prediction, treatment monitoring, prognosis or otherwise evaluation of bladder cancer, includes a pair of primers and a probe for multiplex methylated regions as shown in tables 2-1, 2-2, and 2-3:

TABLE 2-1

Combination of Primer and Probe Sequences for Detecting Co-Methylation of 22 Regions

| SEQ ID NO: | Forward primer sequence | SEQ ID NO: | Reverse primer sequence | Corresponding region NO: |
|---|---|---|---|---|
| 23 | GGAAGATTCGGGTATCGTTTAGCGTA | 45 | GCACACACCGCTACTTACGCTTCCG | 1 |
| 24 | TGTTCGGCGGTTCGGGTATCG | 46 | GCTACCCAAACTATAAATACGAATAAACGT | 2 |
| 25 | TGGCGGTTAAAGTGGTTTCGA | 47 | CACTTAATAAATTTCTCTAACACGAATCGAT | 3 |
| 26 | CGGGTTTTAGGGTTTTCGCGT | 48 | CGAAACTCGAAACCGCGAAAC | 4 |
| 27 | TTCGGAGTGGGGTAGGTGTC | 49 | ATAACGCTCCCCGCAAACTAA | 5 |
| 28 | TCGGTGGTGTATTACGAGGGTT | 50 | AACGACTAACGACGACGACGA | 6 |
| 29 | GCGGGAATTGAGTGTTGGTTC | 51 | TACCGTCTATATTTCGATAACCGCGA | 7 |
| 30 | TCGCGTTTTCGTTTTCGCGT | 52 | ATACCCCGTCCCTACAATTACCT | 8 |
| 31 | ATTCGTTTCGGAATCGACGTGAGC | 53 | CGAACGAACTAAAAATA | 9 |
| 32 | GTAGTAGTTGTAGGAAGCGGATTC | 54 | CGCTATCTCCCCGAACGTACC | 10 |
| 33 | ACGACAAAACGTTCAACCGCA | 55 | TTTGTCGTAAAATTCGTAGACGAAG | 11 |
| 34 | TTATTTTAGTCGTGTTTCGTTTCGGA | 56 | CTACGAACGACGCTACTACTCCTAC | 12 |
| 35 | TCGGTGGGGTATTAAAAGGGAA | 57 | TAAATAAAACACGACAACTATAA | 13 |
| 36 | CGGTAGCGTTTAGTTTTCGTATTTC | 58 | CTAAATAAATCGCAACGAACGCGA | 14 |
| 37 | TTTCGATTTTGTTTTACGTTTGTCG | 59 | AACGCGCTCCTCCGACG | 15 |
| 38 | CGTGTTTGAGGTTCGCGGGT | 60 | CTACTCTACCACACGCAACCCGCAC | 16 |
| 39 | TCGGTAGTGGTTATTATATTTGGTTTTC | 61 | ACTTTTACCCCGCCAACCCCG | 17 |
| 40 | CGCGGTTATCGTTCGTTTATTATTC | 62 | ATCCCAAACCCGCACGATT | 18 |
| 41 | TGCGCGGAGTTTACGCGATT | 63 | ACGAACACGACTCACGCGCA | 19 |
| 42 | GGAGCGTGCGGGTAGCGTT | 64 | CGAATAAAACTACCACCGCGA | 20 |

TABLE 2-1-continued

Combination of Primer and Probe Sequences for Detecting Co-Methylation of 22 Regions

| | | | | |
|---|---|---|---|---|
| 43 | TTGATTCGTGTTTTGTATGTTGGTAGT | 65 | AAAATAACTCGAATTCCCCAACC | 21 |
| 44 | GAGAGAAAGTTTTATTTGTAGTAGTCGAA | 66 | ACGCTCTCTTTAAAATCGCGTCC | 22 |

| SEQ ID NO: | Probe sequence | Corresponding region sequence SEQ ID NO: |
|---|---|---|
| 67 | CGATCCGCCTAAACGACTAAATCCGCGA | 1 |
| 68 | GAGTCGGTCGAGTTTTAGTCGGAGTTACGT | 2 |
| 69 | CCCTTAATCCCCGTCAATTATCATCCCGA | 3 |
| 70 | GCGAAAACCGCGCTCTACTCTCCG | 4 |
| 71 | CCTCTACCCACCGTACCGCGTCTACTTCC | 5 |
| 72 | TACGACGACGACGACGACAAACG | 6 |
| 73 | CGAAACCGAACCCGCGAACTCTCCGA | 7 |
| 74 | GACCCGAATCCCGCAAACCAAACCG | 8 |
| 75 | CGCCTCCACGAACCGACCCCG | 9 |
| 76 | TCAATTCCCCTCCGAAACTCCTTTCCGC | 10 |
| 77 | CGCTCAACACGCATATCCGCATCCACGC | 11 |
| 78 | CGACCGACGAACGACAAATAAATCCCGACG | 12 |
| 79 | CGGTTTTTGGCGATTCGGTGATTTGTAGCGGC | 13 |
| 80 | CGATCGCGACGAAACTCAAATACGATATAC | 14 |
| 81 | CGCCCCAACGCACTCCGCTAAAACGAA | 15 |
| 82 | CTTCTAACGACTCCCGCGAAACCAAC | 16 |
| 83 | AAGGTAGCGGTCGTTGGAGT | 17 |
| 84 | TCGCCCGATACCAACCCAAATACGCG | 18 |
| 85 | CGAACTCCGCGCCTTCCCAAAAACCCCG | 19 |
| 86 | CGACCGCTTCCTAAACTACGCTAAAATTCG | 20 |
| 87 | CGATAAAACCACCCGAAACAACTCAACA | 21 |
| 88 | ACTCCCGCCGTCCCATTACCGAAATA | 22 |

TABLE 2-2

Combination 2 Of Primer and Probe Sequences for Detecting Co-Methylation of 22 Methylated Regions

| SEQ ID NO: | Forward primer sequence | SEQ ID NO: | Reverse primer sequence | Corresponding SEQ ID NO |
|---|---|---|---|---|
| 89 | TATACGCACACACCGCTACTTACG | 111 | TAGGAAGATTCGGGTATCGTTTAGC | 1 |
| 90 | ATGTTCGGCGGTTCGGGTATC | 112 | GCTACCCAAACTATAAATACGAATAAACG | 2 |
| 91 | TTGGCGGTTAAAGTGGTTTCG | 113 | CCACTTAATAAATTTCTCTAACACGAATCG | 3 |
| 92 | GAAACTCGAAACCGCGAAACC | 114 | CGTCGGGTTTTAGGGTTTTCG | 4 |

TABLE 2-2-continued

Combination 2 Of Primer and Probe Sequences for
Detecting Co-Methylation of 22 Methylated Regions

| | | | | |
|---|---|---|---|---|
| 93 | TAACGCTCCCCGCAAACTAAA | 115 | TCGGAGTGGGGTAGGTGTCG | 5 |
| 94 | CATAACTACAACGACTAACGACGA | 116 | CGGTGGTGTATTACGAGGGTTA | 6 |
| 95 | CGGGAATTGAGTGTTGGTTCG | 117 | AATCTACCGTCTATATTTCGATAACCG | 7 |
| 96 | AATACCCCGTCCCTACAATTACC | 118 | TTTTCGCGTTTTCGTTTTCGC | 8 |
| 97 | CGACTCCGAACGAACGAACTA | 119 | TGGAGAGGGGTTATTCGTTTCG | 9 |
| 98 | GCTATCTCCCCGAACGTACCTA | 120 | TAGTAGTTGTAGGAAGCGGATTCG | 10 |
| 99 | TGTCGTAAAATTCGTAGACGAAGG | 121 | CGACAAAACGTTCAACCGCAA | 11 |
| 100 | TGTTATTTTAGTCGTGTTTCGTTTCG | 122 | CTACTACGAACGACGCTACTACTCC | 12 |
| 101 | CTCAACTCAAATAAATAAAACACGACAA | 123 | CGGTGGGGTATTAAAAGGGAAG | 13 |
| 102 | GTAATCGGTAGCGTTTAGTTTTCG | 124 | AAATCTAAATAAATCGCAACGAACG | 14 |
| 103 | TTTTTAGTTGTTTTCGATTTTGTTTTAC | 125 | GCGCTCCTCCGACGA | 15 |
| 104 | ACAATACTCCTACTCTACCACACGCA | 126 | TTGAGGTTCGCGGGTAATTG | 16 |
| 105 | CGGTAGTGGTTATTATATTTGGTTTTCG | 127 | AAACTTTTACCCCGCCAACC | 17 |
| 106 | GCGGTTATCGTTCGTTTATTATTCG | 128 | ATCCCAAACCCGCACGAT | 18 |
| 107 | AACCCTACGAACACGACTCACG | 129 | AGATTGCGCGGAGTTTACG | 19 |
| 108 | CGTGCGGGTAGCGTTTTC | 130 | CACTCCGAATAAAACTACCACCG | 20 |
| 109 | AAAATTGATTCGTGTTTTGTATGTTGG | 131 | AAATAACTCGAATTCCCCAACCG | 21 |
| 110 | GCTCTCTTTAAAATCGCGTCCTC | 132 | GGAGAGAAAGTTTTATTTGTAGTAGTCGA | 22 |

| SEQ ID NO: | Probe sequence | Detection region of Corresponding SEQ ID NO: |
|---|---|---|
| 133 | CGACGATCCGCCTAAACGACTAAATCCG | 1 |
| 134 | CGTAACTCCGACTAAAACTCGACCGACTCG | 2 |
| 135 | TCCCTTAATCCCCGTCAATTATCATCCCG | 3 |
| 136 | CGCTCTACTCTCCGCCCAAACTAAACCA | 4 |
| 137 | ACCTCTACCCACCGTACCGCGTCTACTTC | 5 |
| 138 | CGACAACTACGACGACGACGACGACAA | 6 |
| 139 | CCGAAACCGAAACCGAAACCGAACC | 7 |
| 140 | CGACCCGAATCCCGCAAACCAAACC | 8 |
| 141 | AATCCCTCAACCGCCTCCACGAACC | 9 |
| 142 | CTCAATTCCCCTCCGAAACTCCTTTCCG | 10 |

TABLE 2-2-continued

Combination 2 Of Primer and Probe Sequences for Detecting Co-Methylation of 22 Methylated Regions

| | | |
|---|---|---|
| 143 | CACGCATATCCGCATCCACGCGAA | 11 |
| 144 | TCCTAATAACCTCCGACCGACGAACGACA | 12 |
| 145 | TTAATCACACGCCGCTACAAATCACCGAA | 13 |
| 146 | CGCGACGAAACTCAAATACGATATACAACG | 14 |
| 147 | ACGCGCCCCAACGCACTCC | 15 |
| 148 | CGCACCCTTCTAACGACTCCCGC | 16 |
| 149 | CGCTACTCCAACGACCGCTACCTTAAA | 17 |
| 150 | CTTCGCCCGATACCAACCCAAATACGC | 18 |
| 151 | GCACATCCCCGACTTCCCCGAAC | 19 |
| 152 | TCTCCTCCGACCGCTTCCTAAACTACGCTA | 20 |
| 153 | AAAACCACCCGAAACAACTCAACAACAAAA | 21 |
| 154 | AATACTCCCGCCGTCCCATTACCGA | 22 |

TABLE 2-3

Combination 3 of primer and probe sequences for detecting co-methylation of 22 methylated regions.

| SEQ ID NO: | Forward primer sequence | SEQ ID NO: | Reverse primer sequence | Corresponding region NO: |
|---|---|---|---|---|
| 155 | TTGTGCGTATATATCGTTATTTGCG | 177 | GAACACCGTTCAACGCATTAACTTCG | 1 |
| 156 | GTTTAGGTTGTAGGTGCGGGTGGAC | 178 | TATTCGACGACCCGAACACCG | 2 |
| 157 | TCGAACGGTTTTTATTTTTCGT | 179 | AACGAAAATCAAAAAATTACCCATTCTA | 3 |
| 158 | TTCGTCGAGGAGGAGGAGTAC | 180 | CCAACCTAAACGAAAAACAAAACG | 4 |
| 159 | ATAGCGTTTTTCGTAGGTTGGGGA | 181 | CGAAATAAAACAAATATCGAAACTA | 5 |
| 160 | TATGGTTGTAGCGGTTGGC | 182 | CGATAATACACCACGAAAACTACCCG | 6 |
| 161 | TTTATCGTTTGTGTTTCGGTAATCG | 183 | CGAAAACTAAATACTAACCCGAA | 7 |
| 162 | GGAGTAGGAGGGGTGTTTCG | 184 | CCGCGTTCCGACCTAACC | 8 |
| 163 | CGGGCGGGTTGGAAGTGGG | 185 | TCATCCGCCCCGAAACCG | 9 |
| 164 | CGTTGTTTTTTCGAACGTGTTTGG | 186 | ACAACAACTACAAAAAACGAAC | 10 |
| 165 | CGATAAAACGTTTAATCGTAATTT | 187 | TATCGTAAAATTCGTAAACGAAA | 11 |
| 166 | TTATTGCGGGCGGCGTTGTTG | 188 | AACCGTATCCCGCTCCGAAAAC | 12 |

TABLE 2-3-continued

Combination 3 of primer and probe sequences for detecting co-methylation of 22 methylated regions.

| | | | |
|---|---|---|---|
| 167 | TACGATAGTTGTGGAAGATTAATTA | 189 | CGACCTTCCCGATAAAACACCAAA | 13 |
| 168 | GGTTTGAATGGGTCGTAGCGAGC | 190 | CGACAACGTCCAACTCCCGCACCTCG | 14 |
| 169 | CGCGTTTTTTCGGCGGGTT | 191 | CTCGATTTTACTCCACGCCTACCGA | 15 |
| 170 | TTTATTTTGTTATACGTAGTTCGTATT | 192 | CGTATCTAAAACTCGCGAACAACTA | 16 |
| 171 | GTTTTTATTTCGTTAGTTTCG | 193 | TCGACAATAACCACCACATCTAATTCTC | 17 |
| 172 | TTTAGATTCGTACGATTTTTCG | 194 | GCGACCACCGCCCGTTC | 18 |
| 173 | TACGGTTTACGCGTATATTTTC | 195 | AAATTACGCGAAACCCACGCGA | 19 |
| 174 | TCGGATGGGGTTGTTATCGC | 196 | GTACGAACAACGCCCCCGA | 20 |
| 175 | GAATGGTTCGGATTTTTTAGTC | 197 | ACTAATCCGTATCCTACATATTA | 21 |
| 176 | TTTTAGAATCGCGTTTTTTTAAATG | 198 | AAATCCTATCTACAACAACCGAATA | 22 |

| SEQ ID NO: | Probe sequence | Corresponding region sequence SEQ ID NO: |
|---|---|---|
| 199 | GAACCCAACCGCCCAAACGAATCGCCG | 1 |
| 200 | GAACCGACCGAACTCCAACCGAAACTACG | 2 |
| 201 | CTATAAAAACCGATTCGTACCAAA | 3 |
| 202 | CGCGACCTCGAACC | 4 |
| 203 | AAACAAACGCGATACGATAAACAA | 5 |
| 204 | GCCGCCGCCGCAACTACCGCCG | 6 |
| 205 | GACCTCGACCTCGACCTCGACCTTCGA | 7 |
| 206 | ACGAAATTCGAACCGAAACAACTAC | 8 |
| 207 | CGTAAACGCGAAACCGACCCGTAAAAACGA | 9 |
| 208 | CGACGAAAAAAACCCCGAAA | 10 |
| 209 | CGTTTAATACGTATATTCGTATTTACGCG | 11 |
| 210 | CGCCGAAACCCATCTACCGCTCGCCGACCG | 12 |
| 211 | CGTCGTTGTAAGTTATCGGGTCGTTAGGGGTC | 13 |
| 212 | CGCACCTAAACCCCGCCGCGACCGCATCG | 14 |
| 213 | CAACGAAATACGCTAAAACGCGCCA | 15 |
| 214 | TCTAAATTAACCTCGCGAAAACCGCCAA | 16 |
| 215 | GTTTTAGCGGTCGTTGTTTTAGAAAAGTTAAC | 17 |
| 216 | CCGCGCGCATCTAAACTAACACCGA | 18 |
| 217 | AAACGCCGAAAACAACGAAACTCTTAA | 19 |
| 218 | CCTAACGCAACCCAAAAAACGATCGAA | 20 |
| 219 | ACTAAACTATCCCGAATAACTTCACCG | 21 |
| 220 | TCCCCATTCCGATAATAAAACGACGAA | 22 |

In general, primers and probes are selected according to the combination of specific methylated regions.

Primers and Probe for Internal Reference

| Forward primer sequence | Reverse primer sequence | probe |
|---|---|---|
| GTGATGGAGGAGG TTTAGTAAGTT (SEQ ID NO: 221) | CCAATAAAACCTACT CCTCCCTTAA (SEQ ID NO: 222) | ACCACCACCCAACAC ACAATAACAAACACA (SEQ ID NO: 223) |

In some embodiments, the kit includes one of the three combinations of the primer and probe for PCR amplification (probe fluorescent label can be FAM fluorescent label, VIC fluorescent label, NED fluorescent label and the like), the three combinations have similar performance in detection of the 22 regions.

As an example, detection of co-methylation level of the methylated region of SEQ ID NO:8 is illustrated as follows.

Example 4

Figure 4:
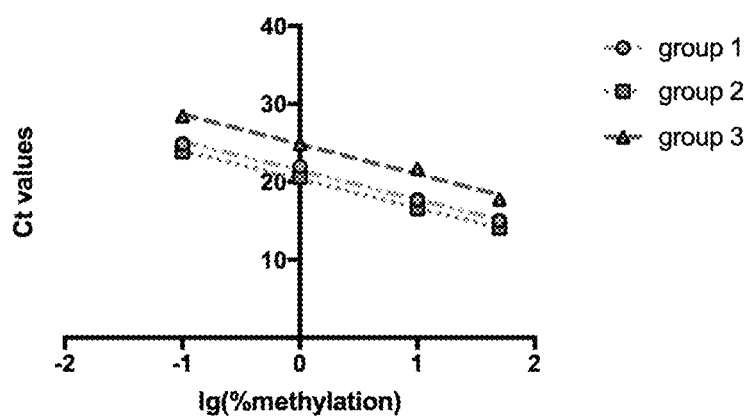
FIG. 4: Comparison in co-methylation levels of the methylated region of SEQ ID NO. 8 by using three sets of primers or probes.

The co-methylation level of the regions of a series of standard products (Qiagen company) was detected according to the detection method of Example 5 by using a pair of primers in the three combination respectively, as shown in FIG. 4. The linear relationships of the primers and probes of combinations 1, 2 and 3 for the detection of the co-methylation in these regions were 0.993, 0.998 and 0.987, respectively. There was no significant difference in the linear relationships. The linear fitted equations had a slope of −3.73, −3.66 and −3.83, respectively, from which it can be determined that their amplification efficiency was similar without any significant difference.

Example 5

Detection of the co-methylation of 2 or 3 DNA methylated regions by multiple fluorescence quantitative PCR. Commercially available completely methylated (positive control) and non-methylated (negative control) standard products (purchased from QIAGEN) were used to detect the co-methylation of every 2 or 3 DNA methylated regions for the 22 methylated regions (SEQ ID NOS:1-22).

TABLE 3 scheme for preparation of PCR mixture.

| Reagent | final concentration | volume (μL) |
|---|---|---|
| DEPC water | | 18.5 |
| 5× PCR Buffer | 1× | 10.0 |
| 25 mM MgCl₂ | 0.25 mM | 0.5 |
| 25 mM dNTP mixture | 250 μM | 0.5 |
| 5 μM Primer mixture | 0.5 μM | 5.00 |
| 5 U/μl Taq enzyme | 2.5 Unit | 0.5 |
| volume [μl] | | 35.00 |

Adding DNA samples: into the PCR reaction well, added was 35 μL PCR mixture, followed by the converted DNA which had a loading amount of 25 ng before DNA conversion; the PCR reaction system had a total volume of 50 μL. Vortex and centrifugation.

Procedure for the PCR reaction: 98° C. for 30 seconds; 20 cycles of 98° C. for 15 seconds, 60° C. for 15 seconds, 72° C. for 15 seconds; and 72° C. for 5 minutes. Product was store at 4° C. for use.

Multiplex fluorescence quantitative PCR: primers and probes for 22 methylated regions (see sequences listed in tables 2-1, 2-2, and 2-3), and primers and probes for internal reference for each methylation region were prepared as sets of mixture at a concentration of 10 μM for primer and of 5 μM for probe respectively. In 22 sets of mixture for 22 methylated regions, sets of mixture for every 2 or 3 methylated regions can be mixed at an equal ratio. Some combinations for three methylated regions are listed in table 4:

TABLE 4

Mixture combination scheme of primer and probe for 22 methylated regions (SEQ ID NOS: 1-22) (any 2 or 3 methylated regions in the combination can be optionally selected)

| combination scheme | FAM labelled fluorescent channel | VIC labelled fluorescent channel | NED labelled fluorescent channel |
|---|---|---|---|
| combination A | SEQ ID NO. 2 | internal reference | SEQ ID NO. 1 |
| combination B | SEQ ID NO. 17 | SEQ ID NO. 20 | SEQ ID NO. 1 |
| combination C | SEQ ID NO. 2 | SEQ ID NO. 9 | SEQ ID NO. 8 |
| combination D | SEQ ID NO. 15 | internal reference | SEQ ID NO. 6 |
| combination E | SEQ ID NO. 3 | SEQ ID NO. 18 | SEQ ID NO. 14 |
| combination F | SEQ ID NO. 16 | | SEQ ID NO. 12 |
| combination G | SEQ ID NO. 22 | SEQ ID NO. 5 | SEQ ID NO. 4 |
| combination H | SEQ ID NO. 13 | SEQ ID NO. 10 | SEQ ID NO. 21 |
| combination I | SEQ ID NO. 19 | SEQ ID NO. 11 | SEQ ID NO. 7 |
| combination J | | internal reference | SEQ ID NO. 7 |
| combination K | internal reference | internal reference | SEQ ID NO. 6 |
| combination L | SEQ ID NO. 3 | internal reference | SEQ ID NO. 4 |

Preparation of the multiplex qPCR reaction solution: according to the combination scheme in table 5, primer and probe mixture for the selected 2 or 3 methylated regions was mixed at an equal ratio to prepare PCR mixture without addition of DNA therein.

TABLE 5 scheme for preparation of PCR mixture.

| Reagent | volume (μL) |
|---|---|
| DEPC water | 1.5-2 |
| 2 X PCR Master Mix | 5.00 |
| primers and probes for 2 or 3 marker | 0.5 (each set) |
| volume[μl] | 8.00 |

Adding DNA samples: into the PCR reaction well, added was 8 μL PCR mixture, followed by 2 μL product of the multiplex PCR which has been subjected to to-fold dilution; the PCR reaction system had a total volume of 10 μL. Vortex and centrifugation.

Procedure for fluorescence quantitative PCR reaction: 95° C. for 5 minutes; 95° C. for 20 seconds, 62° C. for 60 seconds, and Fluorescence signals were collected at 62° C., 40 cycles.

Example 6

Co-methylation detection of 5 DNA methylation regions from the 22 DNA target regions by multiplex fluorescence quantitative PCR. This procedure is similar to Example 5.

The commercially available fully methylated (positive control) and fully non-methylated (negative control) standards (purchased from QIAGEN) were used to detect the co-methylation of any 2 or 3 of the 22 DNA methylation regions (SEQ ID NOS:1-22) which included the 5 regions mentioned above.

DNA extraction: DNA extraction kit was purchased from QIAGEN company and DNA extraction was carried out according to the instruction for the extraction kit.

DNA conversion with bisulfite: DNA bisulfite conversion kit was purchased from Zymo and DNA bisulfite conversion was carried out according to the instructions of the kit.

Multiplex PCR amplification: Pairs of primer (primer sequences shown in table 2-1, 2-2, and 2-3) for 22 methylated regions (SEQ ID NOS:1-22) were used to conduct multiplex PCR in a reaction well to amplify the target sequences containing the target regions. The product had a size of about 70-130 bp.

The PCR primer mixture with a single primer having a concentration of 5 µM (per primer) was prepared, which contained forward and reverse primers for each methylated region for the multiple reactions, all in one reaction well. PCR mixture was prepared according to table 3, without addition of DNA therein.

Adding DNA samples: 35 µL PCR mixture was added into each well, followed by the addition of the converted DNA of 25 ng input before DNA conversion; the PCR reaction system had a total volume of 50 µL. Vortex for mixing and perform centrifugation.

PCR reaction: 98° C. for 30 seconds; 20 cycles of 98° C. for 15 seconds, 60° C. for 15 seconds, 72° C. for 15 seconds; and 72° C. for 5 minutes. The product was store at 4° C. before use.

Multiplex fluorescence quantitative PCR: Primers and probes of 22 methylated regions (sequences listed in Table 2, the sequence in table 2-2 was used herein, i.e., combination 2, and applied to all the following embodiments), and primers and probes for internal reference were prepared as sets of mixture at a final concentration of 10 µM per primer and of 5 µM per probe, respectively. In 22 sets of mixture of 22 methylated regions, sets of mixture for any 2 or 3 methylated regions can be mixed at an equal ratio. Some combinations for simultaneous detection of three methylated regions were listed in Table 6.

TABLE 6

Mixture combination scheme of primer and probe of 22 methylated regions (SEQ ID NO. 1-22) (any 2 or 3 methylated regions in the combination can be used)

| Combination Scheme | FAM Labelled Fluorescent Channel | VIC Labelled Fluorescent Channel | NED Labelled Fluorescent Channel |
|---|---|---|---|
| combination A | SEQ ID NO. 2 | internal reference | SEQ ID NO. 1 |
| combination B | SEQ ID NO. 17 | SEQ ID NO. 20 | SEQ ID NO. 1 |
| combination C | SEQ ID NO. 2 | SEQ ID NO. 9 | SEQ ID NO. 8 |
| combination D | SEQ ID NO. 15 | internal reference | SEQ ID NO. 6 |
| combination E | SEQ ID NO. 3 | SEQ ID NO. 18 | SEQ ID NO. 14 |
| combination F | SEQ ID NO. 16 | | SEQ ID NO. 12 |
| combination G | SEQ ID NO. 22 | SEQ ID NO. 5 | SEQ ID NO. 4 |
| combination H | SEQ ID NO. 13 | SEQ ID NO. 10 | SEQ ID NO. 21 |
| combination I | SEQ ID NO. 19 | SEQ ID NO. 11 | SEQ ID NO. 7 |
| combination J | | internal reference | SEQ ID NO. 7 |
| combination K | SEQ ID NO. 2 | internal reference | SEQ ID NO. 6 |
| combination L | SEQ ID NO. 3 | internal reference | SEQ ID NO. 4 |
| combination M | SEQ ID NO. 3 | SEQ ID NO. 7 | SEQ ID NO. 5 |

Preparation of the multiplex qPCR reaction solution: according to the combination scheme in Table 5, primer and probe mixture of the said 2 or 3 methylated regions was mixed at an equal ratio to prepare the PCR mixture, without addition of DNA therein.

Adding DNA samples: 8 µL PCR mixture was added into the PCR reaction well, followed by addition of 2 µL multiplex PCR product with 2 time dilution; the PCR reaction system had a total volume of 10 µL. Vortex for mixing and perform centrifugation.

Fluorescence quantitative PCR reaction: 95° C. for 5 minutes; 40 cycles of 95° C. for 20 seconds, 62° C. for 60 seconds with fluorescence signals collected at 62° C.

Example 7

Data analysis. The same data analysis is conducted for Table 4 (combination A-L) and Table 6 (combination A-M). For the sake of brevity and clarity, data analysis of only Table 4 (combination A-L) is discussed below.

The co-methylation levels of the 22 methylated regions were tested by using commercially available fully methylated (positive control) and fully non-methylated (negative control) standards based on the combination scheme shown in Table 4 (combinations A-L) in multiplex fluorescence quantitative PCR. The $C_T$ values were compared with the corresponding $C_T$ values obtained from single plex fluorescence quantitative PCR, the negative controls in all multiplex and single plex measurements were undetectable, and the $C_T$ values for the positive controls are shown in FIG. 9.

As shown in FIG. 9, according to the combination scheme, the primes and probes for any two or three of the methylated regions in the combination were mixed to perform a multiplex fluorescence quantitative PCR, the resulted $C_T$ values are similar to those quantified for a single region, with no significant differences. It was estimated that no mutual interference in the amplification efficiency occurs among the 22 methylated regions in the combination scheme of multiplex fluorescence quantity, the quantitative performance was the same as that in single region quantity, and the simultaneous quantitative detection for 2 or 3 methylated regions can be achieved.

Example 8: Detection of Co-Methylation of 22 Methylated Regions in Bladder Cancer Cell Lines, Bladder Cancer Tissues and Normal Adjacent Tissues The co-methylation of 22 methylated regions was detected for DNA from bladder cancer cell lines 5637.T24 (purchased from Shanghai Institute of cell) and UM-UC-3 (purchased from the sigma), and 16 bladder cancer tissues, corresponding normal adjacent tissues respectively, using the detection method described in Example 5, to verify the application of these methylated regions in the diagnosis of bladder cancer. The $C_T$ values for each methylated region from the detection were corrected by the $C_T$ value for internal reference, and the relative cycle number of the target regions was obtained as d-$C_T$=$C_T$ (target region)–$C_T$ (internal reference). If the target regions are undetectable, the relative cycle number of the target regions is given as d-$C_T$=35. The pathological composition information of 18 patients with bladder cancer is shown in table 7.

TABLE 7

The pathological composition information of 18 patients with bladder cancer.

| | cases | Proportion (%) | Average age (scope) |
|---|---|---|---|
| Grade | | | |
| Low grade | 3 | 18.8% | 60 (48-78) |
| High grade | 13 | 81.2% | 59 (40-77) |

TABLE 7-continued

The pathological composition information of 18 patients with bladder cancer.

| | cases | Proportion (%) | Average age (scope) |
|---|---|---|---|
| stages | | | |
| Ta | 3 | 18.8% | 67 (63-78) |
| T1 | 8 | 50% | 62 (43-73) |
| T2-T4 | 5 | 31.2% | 52 (40-77) |
| Invasiveness | | | |
| muscle-invasive (T2-T4) | 5 | 31.2% | 52 (40-77) |
| non-muscle-invasive (Ta-T1) | 11 | 68.8% | 63 (43-78) |

The median relative cycle number d-$C_T$ values of the co-methylation level of the 22 methylated regions of the bladder cancer cell lines, bladder cancer tissues, adjacent normal tissues and positive controls were shown in table 8. The methylation heat map of all tissue samples according to the d-$C_T$ values for 22 methylated regions is shown in FIG. 1.

TABLE 8

Median relative cycle number d-$C_T$ values for the co-methylation level of the 22 methylated regions of bladder cancer cell lines, bladder cancer tissues and normal adjacent tissues.

| | Bladder cancer cell lines | | | Bladder cancer tissues | normal adjacent tissues | Positive control |
|---|---|---|---|---|---|---|
| SEQ ID NO. | 5637 | T24 | UM-UC-3 | | | |
| 1 | −2.99 | −1.48 | −2.70 | 2.04 | 5.22 | 2.19 |
| 2 | 35 | −3.79 | 35 | 7.45 | 13.06 | 4.17 |
| 3 | −4.22 | −3.55 | −3.59 | 0.90 | 6.28 | −1.03 |
| 4 | −0.73 | −0.93 | −0.75 | 1.45 | 4.13 | −3.89 |
| 5 | −2.97 | −2.11 | −1.78 | 0.29 | 2.72 | −3.68 |
| 6 | −0.43 | −2.04 | −1.17 | 1.98 | 4.83 | −2.34 |
| 7 | −3.17 | −3.70 | −3.39 | −1.46 | 0.14 | −4.33 |
| 8 | −2.42 | 0.47 | −2.79 | 0.13 | 3.75 | −3.40 |
| 9 | −1.76 | −2.56 | −0.98 | 0.34 | 3.93 | 1.24 |
| 10 | −4.18 | −4.48 | −3.47 | 4.10 | 3.84 | −2.34 |
| 11 | −3.79 | −4.70 | −3.70 | 0.32 | 2.44 | 3.14 |
| 12 | −0.33 | 0.34 | 0.90 | −0.21 | 4.37 | −0.76 |
| 13 | 35 | 35 | 35 | 0.90 | 3.43 | −1.72 |
| 14 | 0.95 | 0.09 | 0.98 | 2.16 | 5.01 | −0.66 |
| 15 | 5.08 | 9.75 | 8.66 | 10.70 | 16.96 | 5.98 |
| 16 | −4.86 | −5.13 | −3.65 | −0.50 | 0.45 | −5.01 |
| 17 | −3.46 | −3.21 | −2.55 | 2.66 | 6.52 | −0.60 |
| 18 | −2.39 | −3.62 | −2.63 | 2.10 | 3.51 | 2.43 |
| 19 | −0.31 | −1.64 | −1.49 | 0.76 | 3.85 | 2.87 |
| 20 | 35 | −2.09 | −0.33 | 1.28 | 4.18 | −1.63 |
| 21 | −0.38 | −0.61 | 0.54 | 2.34 | 5.23 | −1.14 |
| 22 | −3.81 | −4.96 | −3.73 | −0.48 | 1.82 | −0.50 |

As shown in FIG. 1 and table 8, The median cycle number d-$C_T$ values for the co-methylation level of the 22 methylated regions of the bladder cancer cell lines and bladder cancer tissues approached that of positive control, and was lower than that of normal adjacent tissues, showing a statistically significant difference (p<0.005). As a smaller d-$C_T$ value describes a higher co-methylation level, it can be concluded that the co-methylation level of the selected 22 methylated regions, is significantly higher in bladder cancer cell lines and bladder tissues, positively correlated with the development of bladder cancer, and can be used as a biomarker for identifying the occurrence of bladder cancer. In addition, according to analysis on the d-$C_T$ value for 22 methylated regions at different levels and stages according to bladder cancer tissue samples at different levels and stages, it was found that different grade or different stages can be significantly differentiated in some methylated regions (p<0.05), which demonstrates that these methylated regions and their combinations could be further used as biomarkers for identifying the bladder cancer different at different grades or different stages. The methylated regions are listed in table 9, and the values as shown are the median d-$C_T$ values for these methylated regions of respective groups (and interquartile range of these d-$C_T$ values).

TABLE 9

Median d-$C_T$ values (interquartile range, IQR) for different methylated regions of bladder cancer at different grades and stages

| | SEQ ID NO. 6 | SEQ ID NO. 10 | SEQ ID NO. 21 |
|---|---|---|---|
| Grade | | | |
| Low grade | 1.1 (0.43-8.2) | 4.2 (0.23-5.9) | 35 (6.1-35) |
| High grade | 2.2 (0.93-21) | 4.1 (0.69-5.7) | 2.1 (1.3-4) |
| p-value | 0.0111 | 0.3832 | <0.0001 |
| stages | | | |
| muscle-invasive (T2-T4) | 1.7 (0.88-19) | 2.6 (−0.36-5.1) | 2.2 (1.9-4.7) |
| non-muscle-invasive (Ta-T1) | 2.2 (0.57-8.2) | 4.2 (1.4-6) | 2.5 (1.1-6.1) |
| p-value | 0.9289 | 0.0818 | 0.0195 |

Example 9: Detection of the Co-Methylation of 22 Methylated Regions in Urine DNA Samples The co-methylation level of 22 methylated regions were detected for the urine DNA samples from the bladder cancer group, the benign urological disease group, and the healthy group to identify the use of these methylated regions of urine samples in identifying the incidence and typing of bladder cancer. Among them, there are 70 urine samples from patients with bladder cancer, 49 urine samples from patients with benign urinary diseases (including urinary tract stones, urinary tract infection, prostatic hyperplasia, glandular cystitis, etc.) and 5 urine samples from healthy people (urine routine examination/ultrasonic examination of the urinary system showed normal results and no other tumors were suspected). The pathological and clinical information composition of all samples are shown in table 10.

TABLE 10

Pathological and clinical composition information of urine DNA samples

| | Bladder cancer group | Benign urinary disease group | healthy group |
|---|---|---|---|
| cases | 70 | 49 | 5 |
| Average age (range) | 63 (26-83) | 58 (10-90) | |
| gender: cases (proportion) | | | |
| male | 56 (80%) | 33 (67.3%) | 4 (80%) |
| female | 14 (20%) | 16 (32.7%) | 1 (20%) |

TABLE 10-continued

Pathological and clinical composition information of urine DNA samples

| | Bladder cancer group | Benign urinary disease group | healthy group |
|---|---|---|---|
| grade: cases (proportion) | | | |
| preinvasive carcinoma | 2 (2.9%) | | |
| Low grade | 12 (17.1%) | | |
| High grade | 56 (80%) | | |

TABLE 10-continued

Pathological and clinical composition information of urine DNA samples

| | Bladder cancer group | Benign urinary disease group | healthy group |
|---|---|---|---|
| stage: cases (proportion) | | | |
| Ta | 14 (20%) | | |
| T1 | 19 (27.1%) | | |
| T2-T4 | 31 (44.3%) | | |
| Invasiveness: cases (proportion) | | | |
| Muscle-invasive (T2-T4) | 28 (40%) | | |
| Non-muscle-invasive (Ta-T1) | 40 (57.1%) | | |

The co-methylation level of 22 methylated regions was detected for DNA from the 124 urine samples according to the detection method as described in example 5. The $C_T$ values for each methylated region from the detection were corrected by the $C_T$ value for internal reference, and the relative cycle number of the target regions was obtained as d-$C_T$=$C_T$(target region)−$C_T$(internal reference). If the target regions are undetectable, the relative cycle number of the target regions is given as d-$C_T$=35.

Figure 2:
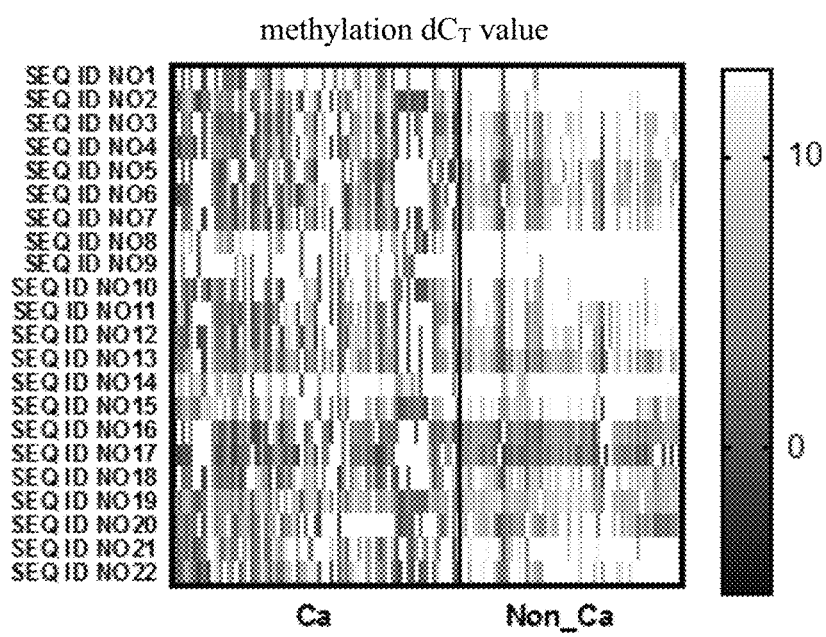
FIG. 2: Heat map of differences in co-methylation of multiple DNA methylated regions in the urine between a patient with bladder cancer and a normal patient.

The median relative cycle number d-$C_T$ values and their interquartile range for the co-methylation of the 22 methylated regions of the DNA from 124 urine samples are shown in table 11. The p-value according to comparison of difference between single methylated regions in different groups is also shown in table 10, in which the standard for statistically significant difference between two groups is p<0.05. The methylation heat map of 22 methylated regions of 124 samples according to the d-$C_T$ values is shown in FIG. 2.

TABLE 11

Analysis of the relative cycle number d-$C_T$ values and interquartile range of d-$C_T$ values for the co-methylation level in the 22 methylated regions of urine DNA samples from bladder cancer group, benign urological disease group and healthy group, and difference in different groups.

| | median d-$C_T$(interquartile range of d-$C_T$ value) | | | | | |
|---|---|---|---|---|---|---|
| SEQ ID NO: | bladder cancer | benign urological diseases | healthy group | p-value*[1] | p-value*[2] | p-value*[3] |
| 1 | 2.1(−0.22-5.7) | 12.5(8.2-35) | 35(22.1-35) | <0.0001 | <0.0001 | <0.0001 |
| 2 | 13.1(6.7-35) | 35(35) | 35(35) | <0.0001 | 0.0025 | <0.0001 |
| 3 | 3.8(−0.66-35) | 35(35) | 35(35) | <0.0001 | <0.0001 | <0.0001 |
| 4 | 4.5(2.9-8.5) | 35(35) | 35(35) | <0.0001 | <0.0001 | <0.0001 |
| 5 | 3.1(1-7) | 35(9-35) | 35(22.8-35) | <0.0001 | <0.0001 | <0.0001 |
| 6 | 3.5(0.63-7.8) | 12.4(8.6-35) | 35(23-35) | <0.0001 | <0.0001 | <0.0001 |
| 7 | 4.4(0.84-4.4) | 7.9(5.7-18.4) | 12(8.4-35) | <0.0001 | 0.0010 | <0.0001 |
| 8 | 4.3(0.5-9.1) | 10.4(7.6-19.3) | 35(35) | <0.0001 | 0.0001 | <0.0001 |
| 9 | 3.1(0.16-7) | 10(6.9-35) | 35(10.3-35) | <0.0001 | 0.0001 | <0.0001 |
| 10 | 3(−0.45-7.1) | 9.2(7.7-11.9) | 8.4(7.7-10.8) | 0.0001 | 0.3258 | 0.0001 |
| 11 | 2.1(−0.66-6.3) | 7.8(6.1-9.8) | 12.8(10.2-24.4) | 0.0002 | 0.0059 | <0.0001 |
| 12 | 35(7.5-35) | 35(35) | 35(35) | 0.0007 | 0.1097 | 0.0004 |
| 13 | 6(2.7-35) | 7.5(5.4-35) | 4.8(3.1-6.3) | 0.3540 | 0.0275 | 0.1655 |
| 14 | 7.7(4.2-35) | 35(35) | 8.6(7.9-22.2) | 0.0001 | 0.8913 | 0.0004 |
| 15 | 13.8(7.9-20.1) | 20.8(14.4-35) | 19.5(15.9-21.1) | 0.0013 | 0.6322 | 0.0018 |
| 16 | 1.5(−1.4-4.2) | 5.1(3.8-6) | 6.6(6-7.2) | 0.0591 | 0.2963 | 0.0438 |
| 17 | 5.4(2.6-12.6) | 35(12.2-35) | 35(23.5-35) | <0.0001 | 0.0002 | <0.0001 |
| 18 | 4.4(1.4-6.2) | 7.6(5.2-9) | 11.2(8-23.6) | 0.0588 | 0.0465 | 0.0251 |
| 19 | 5(2.1-10.4) | 35(9.5-35) | 35(35) | <0.0001 | <0.0001 | <0.0001 |
| 20 | 6.7(2.1-35) | 35(13.7-35) | 35(35) | <0.0001 | <0.0001 | <0.0001 |
| 21 | 6.2(3.7-7.7) | 8.6(7.6-9.8) | 9(8.1-9.4) | 0.1601 | 0.9104 | 0.1788 |
| 22 | 0.65(−1.5-3.5) | 3.6(1.8-5.2) | −0.54(−0.87-0.72) | 0.1339 | 0.8549 | 0.1727 |

*[1]Bladder cancer - benign urological diseases
*[2]Bladder cancer - healthy group
*[3]Bladder cancer - noncancerous group As shown in FIG. 2 and table 11, the median relative cycle number d-$C_T$ values for the co-methylation level of the 22 methylated regions of urine DNA samples from bladder cancer group is significantly lower than that of the benign urological disease group (p<0.05), and thus it can be concluded that the co-methylation level of the selected 22 methylated regions is significantly higher in urine DNA of bladder cancer group, positively correlated with the development of bladder cancer, and can be used as a biomarker for identifying the occurrence of bladder cancer based on a urine sample. Meanwhile, the bladder cancer group and healthy group are significantly differentiated in a plurality of methylated regions. Thus, these methylated regions also can be used as a biomarker for identifying the occurrence of bladder cancer based on a urine sample. In combination with the results from Example 8, the application of the 22 methylated regions in identifying the occurrence of bladder cancer can be used for both tissue samples and urine samples, with similar results.

In addition, according to analysis on the d-$C_T$ value for 22 methylated regions at different levels and stages according to patient pathological information of bladder cancer urine samples, it was found that different grade or different stages can be significantly differentiated in some methylated regions (p<0.05), which demonstrates that these methylated regions and their combinations could be further used as biomarkers for identifying the bladder cancer at different grades or different stages based on urine DNA. The methylated regions are listed in table 12, and the values as shown are the median d-$C_T$ values for these methylated regions of respective groups (and interquartile range of these d-$C_T$ values).

TABLE 12

Median d-$C_T$ values (interquartile range, IQR) for the different methylated regions of bladder cancer at different grades and stages in urine sample group.

|  | SEQ ID NO. 2 | SEQ ID NO. 3 | SEQ ID NO. 6 | SEQ ID NO. 13 | SEQ ID NO. 14 | SEQ ID NO. 15 | SEQ ID NO. 17 |
|---|---|---|---|---|---|---|---|
| Grade | | | | | | | |
| Low grade | 35 (9.6-35) | 35 (3.3-35) | 6.2 (2.4-12.1) | 5.7 (2.7-35) | 13.8 (7.7-35) | 20.5 (7.6-35) | 35 (11.4-35) |
| High grade | 11.4 (6.1-35) | 3.5 (−1.2-10.7) | 3.5 (0.2-7.5) | 6.1 (2.4-35) | 6.6 (4-28.6) | 12.9 (8-17.5) | 4.1 (2.4-8.6) |
| p-value | 0.033 | 0.0016 | 0.3136 | 0.0666 | 0.0215 | 0.0207 | <0.0001 |
| Stages | | | | | | | |
| Muscle-invasive (T2-T4) | 9.3 (6-35) | 3.1 (−1.7-9.1) | 3 (0.35-5.8) | 35 (2.6-35) | 6.6 (3.2-35) | 13.1 (9.5-17.2) | 4.7 (2.3-8.8) |
| Non-muscle-invasive (Ta-T1) | 35 (35) | 5.2 (−0.66-35) | 5 (1.1-10.2) | 5 (2.5-35) | 8.4 (4.2-35) | 14.2 (0.78-29.5) | 5.9 (2.8-35) |
| p-value | 0.0011 | 0.0126 | 0.0493 | 0.0032 | 0.2938 | 0.458 | 0.0912 |

Meanwhile, according to the combination scheme of example 5, the detection method described in this example can be used for the parallel detection of 2-22 methylated regions, and the detection method is flexible, simple and feasible for the combination and collocation of methylated regions.

Example 10: Parallel Co-Methylation Detection of 1-3 Methylated Regions in 22 Methylated Regions When the parallel co-methylation detection of the target methylated regions is carried out on 1-3 methylated regions of the 22 methylated regions, by using the combination scheme in example 5, the detection method can be adopted. The specific detection process is as follows:

1. DNA extraction: DNA extraction kit was purchased from QIAGEN company and DNA extraction was carried out according to the instruction of the extraction kit.
2. DNA conversion with bisulfite: DNA bisulfite conversion kit was purchased from Zymo and DNA bisulfite conversion was carried out according to the instructions of the kit.
3. fluorescence Quantitative PCR assay: Primers and probes for 1-3 methylated regions and internal reference were selected and assay was carried out in one reaction well (primer and probe sequences are shown in tables 2-1, 2-2, and 2-3, and the combination scheme of methylated regions is shown in example 5).

Preparation of qPCR reaction solution: PCR mixture was prepared according to table 13, without adding DNA therein.

TABLE 13

Preparation of qPCR reaction solution

| Reagent | volume (μL) |
|---|---|
| DEPC water | 2.8 |
| 2 X PCR Master Mix | 10.0 |
| primer and probe mixture for one or two or three markers | 0.60 (each type) |

TABLE 13-continued

Preparation of qPCR reaction solution

| Reagent | volume (μL) |
|---|---|
| as described in example 3 | |
| 50X ROX | 0.40 |
| volume [μl] | 15.00 |

1. Adding DNA samples: into the PCR reaction well, added was 15 μL PCR mixture, followed by 2 μL converted DNA which has a loading amount of 25 ng before conversion, wherein the concerted product was put into a PCR reaction well; the PCR reaction system had a total volume of 20 μL. Vortex and centrifugation.
2. procedure for PCR reaction: 95° C. for 5 minutes; 60 cycles of 95° C. for 15 seconds, 62° C. for 40 seconds (fluorescent signal was collected at 62° C.).

Data Processing and Analysis: The $C_T$ values for each methylated region from the detection of the target regions were corrected by the $C_T$ value for internal reference, and the relative cycle threshold of the target regions was obtained as d-$C_T$=T (target region)−$C_T$ (internal reference). If the target regions are undetectable, the relative cycle number of the target regions is given as d-$C_T$=35.

Taking the detection of positive control with combinations A and L of primes and probes for the methylated regions (example 5) as an example, according to the detection method described in example 5, comparison between relative cycle threshold d-$C_T$ value with that in Example 5 is shown in table 14.

TABLE 14

Comparison of d-$C_T$ values from parallel co-methylation detection of 1-3 methylated regions in positive control with that from detection method of 22 methylated regions

| SEQ ID NO. | d-$C_T$ values from parallel detection of 1-3 methylated regions | d-$C_T$ values from detection method of 22 methylated regions |
|---|---|---|
| 1 | 2.48 | 2.19 |
| 2 | 3.40 | 4.17 |
| 3 | −0.58 | −1.03 |
| 4 | −3.09 | −3.89 |

The results in table 14 show that the d-$C_T$ values detected by the method in this example is highly consistent with the d-$C_T$ values detected by the detection method for 22 methylated regions (example 5). The analysis on correlation between the d-$C_T$ values in these regions resulted from the two detection methods showed that the coefficient of correlation is R=0.995 (Pearson R), and thus it can be determined that there was no difference in the detection of the co-methylation level of the same methylated region between the two detection methods.

When the target methylated regions in the parallel co-methylation detection is 1-3 methylated regions of the 22 methylated regions, the detection method described in this example may allow reduced steps for pre-amplifying target fragments by multiplex PCR, making the parallel detection of less than 4 methylated regions more convenient and quick.

Example 11

The mathematical modelling analysis of methylated region combination was carried out for the relative cycle threshold d-$C_T$ value for co-methylation of 22 methylated regions (SEQ ID NOS:1-22) in 124 urine DNA samples obtained in Example 9, to explore the application of 22 methylated regions as a combination of biomarkers in the detection of the occurrence of staging of bladder cancer and to identify the superiority of performance by comparing with a single methylated region as a marker.

First of all, the pathological and clinical information of 124 urine samples was compared. According to the relative cycle threshold d-$C_T$ value for co-methylation of 22 methylated regions in bladder cancer group and non-bladder cancer group (including urinary benign disease group and healthy group) in contrast with pathology, the ROC curve of diagnostic model for identifying the occurrence of bladder cancer based on a single methylated region was established. The AUC value was calculated and identifying threshold value was drawn for this region according to the ROC curve. The sensitivity, specificity and Youden index for this methylated region were calculated according to the threshold value in contrast with pathology. At the same time, according to the relative cycle threshold d-$C_T$ value for co-methylation in 22 methylated regions, 2-22 methylation markers were selected for logistic regression fitting. The fitted equation can be used to calculate the risk score of bladder cancer of each sample to identify the occurrence of bladder cancer. According to the different combinations of 2-22 methylated regions, multiple logistic regression models and equations can be generated for identifying the occurrence of bladder cancer. The sensitivity, specificity, AUC and Youden index for the methylated region combinations were obtained based on the risk scores of bladder cancer calculated from these equations in contrast with pathology. Table 15 shows the comparison of performance parameters for identifying the occurrence of bladder cancer between the combined models and the single methylated region. In addition, FIG. 3 shows the distribution of risk scores in bladder cancer and non-bladder cancer groups using a combined model of 8 methylated regions of the 22 methylated regions (SEQ ID NOS: 1-8).

As shown in FIG. 3, the risk scores of bladder cancer obtained in a combined identifying model of 8 methylated regions can discriminate obviously the bladder cancer group from the non-bladder cancer group, further demonstrating that the combination of these methylated regions can be used as a marker combination for identifying the occurrence of bladder cancer.

From comparison of diagnostic efficacy in table 15, it can be seen that using a single methylated region as the diagnostic model exhibits a lower diagnostic performance than the combined model of multiple methylated regions. The combination of 2-22 methylated regions has a higher sensitivity in identifying the occurrence of bladder cancer, and has a significantly higher Youden index, i.e. an overall performance parameter reflecting the sensitivity and specificity, than identification by a single methylated region, with superior identifying advantage.

TABLE 15

Comparison of a model of single methylated region with a model of multiple methylated regions for the diagnosis of bladder cancer

| Combination of the regions (SEQ ID NO.) | AUC | sensitivity | specificity | Youden index |
|---|---|---|---|---|
| 1 | 0.84 | 70% | 96% | 0.66 |
| 1 + 2 | 0.89 | 80% | 91% | 0.71 |
| 1 + 2 + 3 | 0.89 | 89% | 85% | 0.75 |
| 1-8 | 0.89 | 84% | 85% | 0.69 |
| 1-22 | 0.88 | 81% | 89% | 0.70 |

Furthermore, the sensitivity of the combined model of 2-22 methylated regions for bladder cancer at different grades and stages is compared with that of a single methylated region, as shown in table 16.

TABLE 16

Sensitivity comparison for bladder cancer at different stages and grades between the model of single methylated region and the model of multiple methylated regions

| Combination of the regions (SEQ ID NO) | High-grade bladder cancer | Low-grade bladder cancer | Muscle Invasive bladder cancer | Non-muscle invasive bladder cancer |
|---|---|---|---|---|
| 1 | 86% | 54% | 87% | 80% |
| 1 + 2 | 88% | 70% | 91% | 84% |
| 1 + 2 + 3 | 87% | 75% | 88% | 82% |
| 1-8 | 89% | 70% | 88% | 85% |
| 1-22 | 89% | 75% | 89% | 83% |

The data in table 16 further shows that the sensitivity of the combined model of 2-22 methylated regions is has a higher sensitivity for identifying high-grade, low-grade, muscle invasive and non-muscle invasive bladder cancer than the model of single methylation, indicating that the combined model of 2-22 methylated regions can be used to identify these groups of bladder cancer.

In addition, 2-22 methylated regions were selected to carry out mathematical modelling for high-grade and low-grade bladder cancer groups or muscle invasive and non-muscle invasive bladder cancer groups. Random forest algorithm was used to select the methylated region combination that are capable of making identification, then the identifying threshold value for each methylated region was set to obtain identifying models. According to these identifying models, the bladder cancer group could be classified (high-grade or low-grade) or staged (muscle invasive or non-muscle invasive). The sensitivity, specificity and Youden index can be obtained in contrast with the pathological results. Sensitivity comparison for different grades or stages with the model of single methylated region is shown in table 17.

TABLE 17

Sensitivity comparison for bladder cancer at different grades or stages between the model of multiple methylated region and the model of single methylated region

| Combination of regions (SEQ ID NO.) | Sensitivity | specificity | Youden index |
|---|---|---|---|
| Distinguishing muscle invasive bladder cancer from non-muscle invasive bladder cancer | | | |
| 22 | 88.5% | 39% | 0.275 |
| 13 | 96.2% | 19.5% | 0.157 |
| 22 + 13 + 10 | 88.5% | 68.3% | 0.568 |
| 15 + 13 + 6 + 16 + 18 | 88.5% | 78% | 0.665 |
| 15 + 13 + 6 + 16 + 18 + 10 | 88.5% | 80.5% | 0.690 |
| Distinguishing high-grade bladder cancer from low-grade bladder cancer | | | |
| 17 | 85.7% | 72.7% | 0.584 |
| 22 | 85.7% | 45.5% | 0.312 |
| 17 + 5 + 13 | 87.5% | 90.9% | 0.784 |
| 17 + 22 + 13 | 87.5% | 90.9% | 0.784 |

According to comparison in the grading and staging diagnostic efficiency in table 16, using a single methylated region as a grading and staging diagnostic model exhibits a lower diagnostic performance than the combined model of multiple methylated regions, and the combination of 2-22 methylated regions has a higher sensitivity and specificity in identifying the different grade and stage of bladder cancer, and has a significantly higher Youden index, i.e. an overall performance parameter reflecting the sensitivity and specificity, than identification by a single methylated region, with superior identifying advantage. In addition, it also shows that the combination of multiple methylated regions in these 22 methylated regions can be used for further grading and staging of bladder cancer, which has a more accurate guiding significance for diagnosis scheme and drug guidance for bladder cancer.

Example 12: Simultaneous Co-Methylation Detection of any 1-3 Methylated Regions of the 22 Target Regions When simultaneous co-methylation detection of the target methylated regions is carried out on 1-3 methylated regions of the 22 methylated regions, by using the combination scheme in Table 4 in Example 5, the following detection method can be used. The details of detection are as follows:
1. DNA extraction: DNA extraction kit was purchased from QIAGEN and DNA extraction was carried out following the manufacturer's instructions.
2. DNA bisulfite treatment: DNA bisulfite treatment kit was purchased from Zymo and DNA bisulfite treatment was carried out following the manufacturer's instructions.
3. Fluorescence quantitative PCR assay: The assay was carried out with selected primers and probes of 1-3 methylated regions in one reaction well (primer and probe sequences are shown in table 2, and the combination scheme of methylated regions is shown in Example 5).
4. Preparation of qPCR reaction solution: PCR mixture was prepared according to Table 18, without adding DNA therein.

TABLE 18

Preparation of qPCR Reaction Solution

| Reagent | Volume (μL) |
|---|---|
| DEPC water | 2.8 |
| 2 X PCR Master Mix | 10.0 |
| primer and probe mixture of one or two or three markers as described in Example 2 | 0.60 (each type) |
| 50 X ROX | 0.40 |
| volume [μL] | 15.00 |

5. Adding DNA samples: 15 μL PCR mixture was added into the PCR reaction well, followed by addition of 2 μL bisulfite treated DNA with 25 ng input before conversion; the PCR reaction system had a total volume of 20 μL. Vortex for mixing and perform centrifugation.
6. PCR reaction: 95° C. for 5 minutes; 60 cycles of 95° C. for 15 seconds, 62° C. for 40 seconds with fluorescent signal collected at 62° C.

Data Processing and Analysis: The $C_T$ value of each target methylated regions was normalized by the $C_T$ value for internal reference, and the relative cycle thresholds of the target regions was obtained as d-$C_T$=T (target region)–$C_T$ (internal reference). If the $C_T$ values for target regions are undetectable, the relative cycle thresholds of the target regions is given as d-$C_T$=35.

Taking the detection of positive control with combinations A and L of primes and probes of the methylated regions as an example, according to the detection method described Example 12, comparison between relative cycle thresholds d-$C_T$ value with that in Example 6 is shown in Table 19.

TABLE 19

Comparison of d-$C_T$ values from simultaneous co-methylation detection of any 1-3 methylated regions in positive control with that from detection method of 22 targeted regions.

| SEQ ID NO: | d-$C_T$ values from simultaneous detection of 1-3 methylated regions | d-$C_T$ values from detection method of 22 methylated regions |
|---|---|---|
| 1 | 2.48 | 2.19 |
| 2 | 3.40 | 4.17 |
| 3 | −0.58 | −1.03 |
| 4 | −3.09 | −3.89 |

The results in Table 19 showed that the d-$C_T$ values detected by the method in this example is highly consistent with the d-$C_T$ values detected by the detection method for 22 targeted regions (Example 6). The analysis on correlation between the d-$C_T$ values in these regions resulted from the two detection methods showed that the coefficient of correlation is R=0.995 (Pearson R), and thus it can be determined that there was no difference in the detection of the co-methylation level of the same methylated region between the two detection methods.

When the target methylated regions in the simultaneous co-methylation detection are any 1-3 methylated regions of the 22 targeted regions, the detection method described in this example may allow reduced steps for pre-amplifying target fragments by multiplex PCR, making the simultaneous detection of less than 7 methylated regions more convenient and rapid.

Example 13

Two cohorts were designed to identify and validate the performance characteristics of the biomarker and the combination used for bladder cancer risk stratification prediction, in which the prediction performance was compared to clinical truth as defined by pathology confirmation. Urine samples of the two cohorts were collected before cystoscopy or surgery from Sun Yat-Sen Memorial Hospital. Patients with symptoms of hematuria or/and with abnormal results of primary bladder imaging, but no history of urinary or other malignancies were recruited for the studies.

The patients in BC group were confirmed to be positive by cystoscopy or pathology of TURBT specimen. Based on the pathological diagnosis of the degree of invasion, high and low level, T stage, tumor size and multiple degree, recurrence, et, NMIBC was classified according to NCCN guideline and AUA definition, with BC patients classified into (LMR-NMIBC) group and HR-NMIBC+MIBC group (including high-risk NMIBC and MIBC). While the non-BC group included patients with urinary calculi, urinary tract infection and benign diseases. Urine samples with a genomic DNA amount of less than 25 ng were excluded due to insufficient materials for analysis. Patient clinical characteristics of the studies are summarized in Table 20. The study was conducted under the approval of the Local and Regional Institutional Review Committee of Sun Yat-Sen Memorial Hospital, Sun Yat-sen University. The written informed consent was obtained from all participants.

TABLE 20

Patient Characteristics In The Two Cohorts

| Characteristics | Cohort 1 (for model development) | | Cohort 2 (for independent validation) | |
| --- | --- | --- | --- | --- |
| | Groups | | | |
| | BC | Non-BC | BC | Non-BC |
| Number of participants | 118 | 98 | 64 | 46 |
| Measurement available | 116 | 89 | 60 | 45 |
| Age [Mean (range), years] | 63 (17-83) | 55 (10-97) | 64 (39-83) | 54 (22-83) |
| Gender | | | | |
| Female (n, %) | 20 (17.2%) | 35 (39.3%) | 13 (21.7%) | 13 (28.9%) |
| Male (n, %) | 95 (81.9%) | 54 (60.7%) | 47 (78.3%) | 32 (71.1%) |
| Not available (n, %) | 1 (0.9%) | — | — | — |
| T Staging | | | | |
| Tis (n, %) | — | — | 1 (1.7%) | — |
| Ta (n, %) | 30 (25.9%) | — | 16 (26.7%) | — |
| T1 (n, %) | 38 (32.8%) | — | 18 (30.0%) | — |
| T2 (n, %) | 20 (17.2%) | — | 10 (16.7%) | — |
| T3 (n, %) | 22 (19.0%) | — | 13 (21.7%) | — |
| T4 (n, %) | 5 (4.3%) | — | 2 (3.3%) | — |
| Not available (n, %) | 1 (0.9%) | | | |
| Tumor Grades | | | | |
| Low grade (n, %) | 21 (18.1%) | — | 8 (13.3%) | — |
| High grade (n, %) | 95 (81.9%) | — | 52 (86.7%) | — |
| Invasiveness | | | | |
| NMIBC (n, %) | 68 (58.6%) | — | 34 (56.7%) | — |
| MIBC (n, %) | 47 (40.5%) | — | 26 (43.3%) | — |
| Not available (n, %) | 1 (0.9%) | — | — | — |
| NMIBC risk | | | | |
| Low-intermediate risk (n, %) | 26 (38.2%) | — | 12 (35.3%) | — |
| High risk (n, %) | 42 (61.8%) | — | 21 (61.8%) | — |
| Not available (n, %) | — | — | 1 (2.9%) | — |

Figure 5:
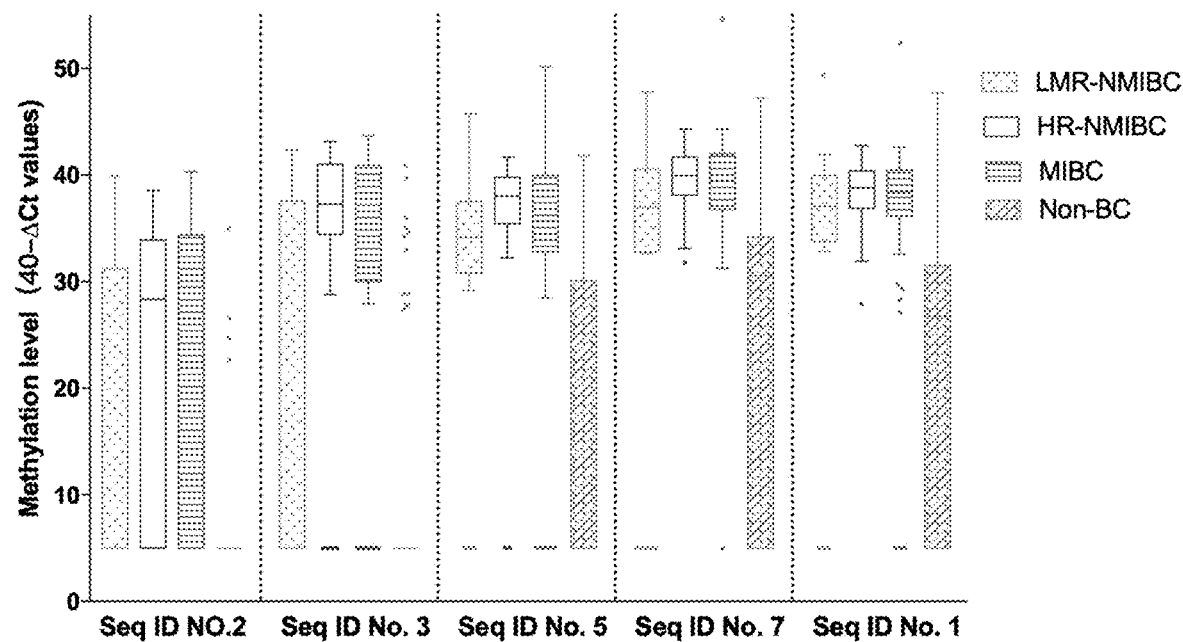
FIG. 5 is a graph showing the distribution of methylation levels of the five methylation biomarkers in different BC risk groups. The methylation level is indicated by 40-ΔCt (relative amplification cycle threshold). A higher 40-ΔCt indicates a higher methylation level. LMR-NMIBC, low-intermediate risk NMIBC; HR-NMIBC, high-risk NMIBC; MIBC, muscle invasive bladder cancer; non-BC, non-bladder cancer.
Figure 6:
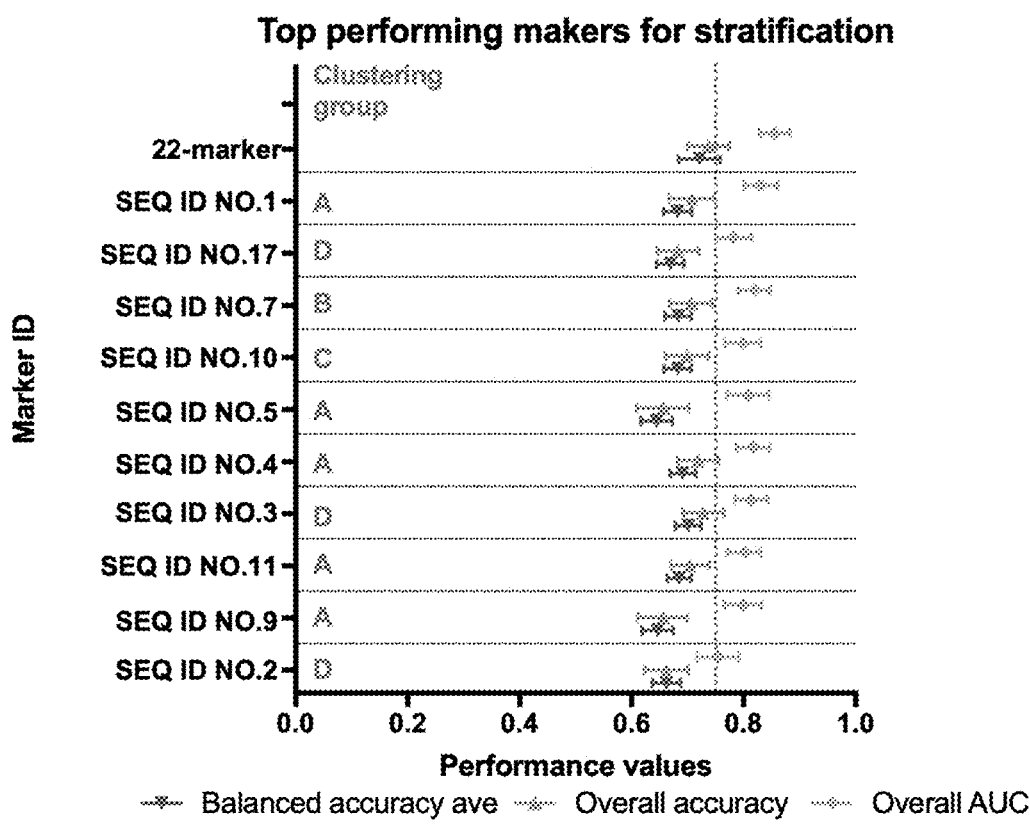
FIG. 6 shows predictive performance features of individual methylation biomarker for bladder cancer risk stratification. Top marker performance from single marker analysis include average of balanced accuracy of the three groups, overall accuracy and overall AUC; values of which were expressed as mean with 95% CI in 100 splits of train-test sampling; groups of clustering were sorted from unsupervised hierarchical clustering.

The detection method in Example 12 was used to detect 22 specific methylated biomarkers on the samples in cohort 1 and 2. First, the data of the sample in cohort 1 was used to perform single marker analysis for feature selection of the 22 targeted regions for risk stratifying of bladder cancer of the three groups (Non-BC, LMR-NMIBC, HR-NMIBC+MIBC). As shown in FIG. 5, the biomarker showed distinct methylation levels between Non-BC and all the BC groups. Furthermore, the level of methylations showed distinct differences between LMR-NMIBC and HR-NMIBC, with the level in HR-NMIBC similar to MIBC. These observations are in concordance with current understanding of HR-NMIBC showing high recurrent and progression rate and poorer survivals. The biomarkers also showed high overall AUCs, high average balance accuracy, and overall accuracy for three-class risk classification in FIG. 6. An estimation of performance of all 22-marker revealed overall higher AUC and accuracy than individual markers, indicating models with multiple markers may enhance classification power (FIG. 6). These indicates that not any arbitrary markers or their combination can stratify the grade or stage of BC.

In addition, the inventors performed iterative combinations of top markers and redundant marker minimization, and finally creatively found the optimum combination of five biomarkers (SEQ ID NOS:1, 2, 3, 5, and 7) could be used to predict the risk stratification of BC. The clinical performance of combination of the five biomarkers mentioned above compared to the combinations of other markers with patient samples of cohort 1 (Table 20) is shown in Table 21.

TABLE 21

| Combinations (SEQ ID NO) | Overall AUC | Overall Accuracy | Average balanced Accuracy |
|---|---|---|---|
| 3 | 0.814 | 72.8% | 70.0% |
| 3 + 5 + 7 | 0.871 | 75.4% | 76.6% |
| 3 + 5 + 7 + 1 + 2 | 0.881 | 78.0% | 79.4% |
| 10 + 11 + 17 | 0.837 | 70.6% | 69.3% |
| 4 + 6 + 9 | 0.838 | 72.5% | 69.9% |
| 1-22 | 0.856 | 73.7% | 72.1% |

As shown in Table 21, the risk stratification performance characteristics of the 22 marker combination are better than that of a single marker, but not the optimal one. Models using biomarker combination of SEQ ID No. 3, 5, 7 and SEQ ID No. 3, 5, 7, 1 and 2 showed the optimal performance for bladder cancer risk stratification, while the model comprised of other marker combinations failed to reach the said performance characteristics.

Figure 7:
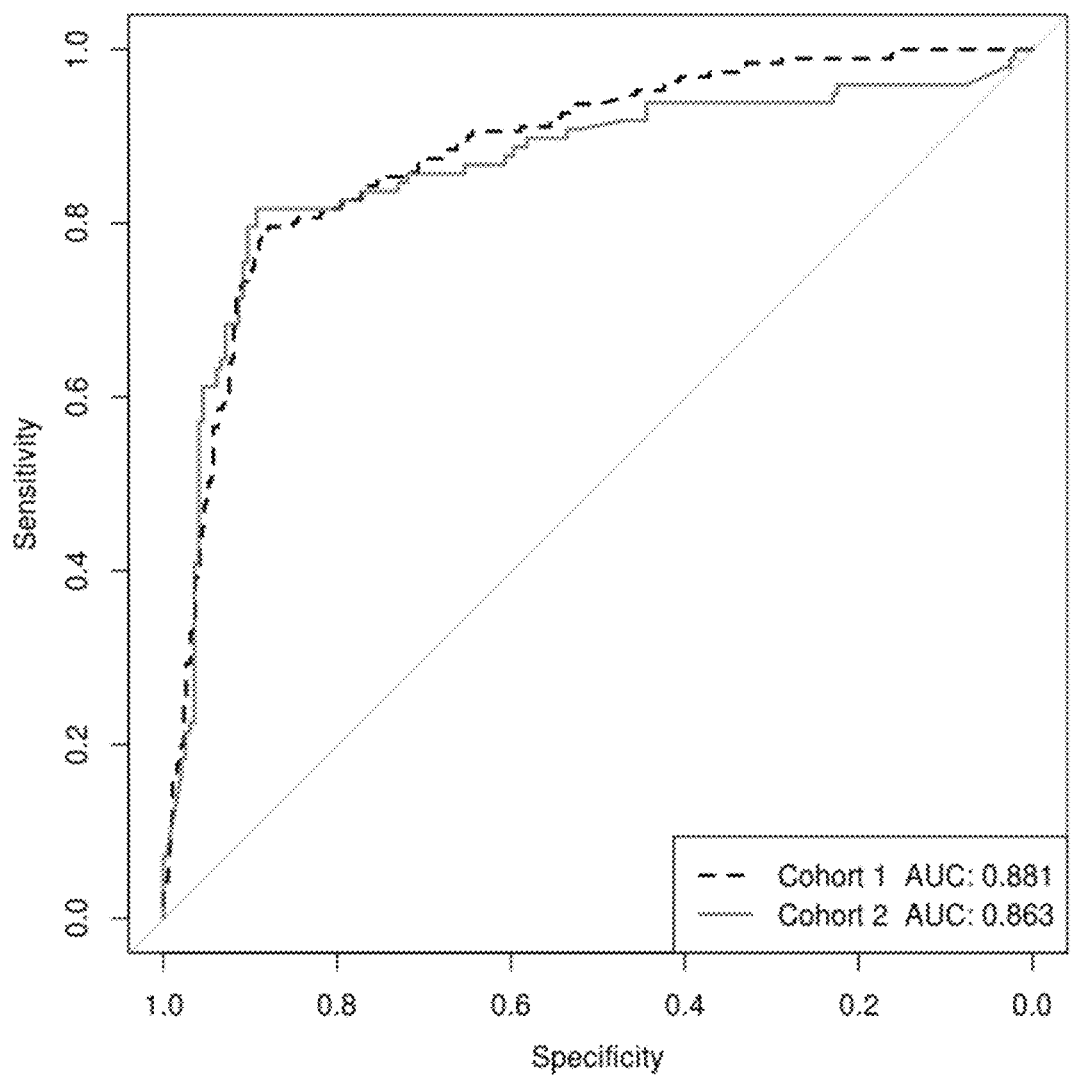
FIG. 7 is a ROC curves of stratification model in Cohort 1 and 2; the dotted line indicated the ROC curve of Cohort 1 and the solid line indicated the ROC curve of Cohort 2.

In addition, the combination of the five biomarkers is further verified with samples in cohort 2, and the performance features are listed in FIG. 7 and FIG. 8. As shown in FIG. 8, the model of the five biomarkers combination identified non-BC group with 84.7% sensitivity, 87.2% specificity and 79.1% NPV, and identified HR-NMIBC+MIBC patients with 81.2% sensitivity, 90.0% specificity and 88.6% PPV in Cohort 2. In addition, the NPVs of 93.1% and 83.3% in both LMR-NMIBC group and HR-NMIBC+MIBC group indicated relatively low false negative rate. These features resulted in both high PPVs of non-BC groups for ruling out patients without BC, and of HR-NMIBC and MIBC groups for ruling in BC patients that required expedited diagnostic and treatment planning. In addition, the revealed high NPVs in both LMR-NMIBC group, and HR-NMIBC or MIBC group ensured low false negative rate for miss-diagnosis.

The foregoing discussion of the invention has been presented for purposes of illustration and description. The foregoing is not intended to limit the invention to the form or forms disclosed herein. Although the description of the invention has included description of one or more embodiments and certain variations and modifications, other variations and modifications are within the scope of the invention, e.g., as may be within the skill and knowledge of those in the art, after understanding the present disclosure. It is intended to obtain rights which include alternative embodiments to the extent permitted, including alternate, interchangeable and/or equivalent structures, functions, ranges or steps to those claimed, whether or not such alternate, interchangeable and/or equivalent structures, functions, ranges or steps are disclosed herein, and without intending to publicly dedicate any patentable subject matter. All references cited herein are incorporated by reference in their entirety.

What is claimed is:

1. A method for assessing bladder cancer risk in a human subject, comprising:
performing bisulfite treatment of a DNA of a urine sample obtained from said subject,
conducting methylation-specific quantitative PCR to amplify the DNA to obtain $C_T$ values for at least two CpG regions of the sequences of SEQ ID NOS: 1 and 2, or the complementary sequences of SEQ ID NOS: 1 and 2;
determining if bladder cancer is present in the subject based on comparing the obtained $C_T$ values of the at least two CpG regions of the sample with respective predetermined ranges of $C_T$ values of the at least two CpG regions to, wherein the predetermined ranges of $C_T$ values were derived from a statistical analysis of a training set of samples including samples in which bladder cancer is present and samples in which bladder cancer is not present; and
treating the bladder cancer in the subject if it is determined that bladder cancer is present in the subject.

2. The method according to claim 1, further including:
detecting in the DNA of the urine sample obtained from said human subject at least a third CpG region;
wherein the conducting methylation-specific quantitative PCR to amplify the DNA comprises obtaining $C_T$ value for at least a third CpG region of the sequence of SEQ ID NO:3, or the complementary sequence thereof;
wherein the determining comprises comparing the obtained $C_T$ value of the third CpG region of the sample with a predetermined range of $C_T$ value of the third CpG region.

3. The method according to claim 2, further including:
wherein the conducting the methylation-specific quantitative PCR to amplify the DNA comprises obtaining $C_T$ values for the at least one further CpG region of the sequence SEQ ID NOS:4-8, or the complementary thereof;
wherein the determining comprises comparing the obtained $C_T$ values of at least one further CpG region of the sample with a predetermined range of $C_T$ value of the at least one further CpG region.

4. The method according to claim 1, wherein said method for diagnosing bladder cancer comprises the detection of low grade of bladder cancer, or detection of high grade bladder cancer.

5. The method according to claim 1, wherein said method for diagnosing bladder cancer comprises classifying low grade of bladder cancer from high grade bladder cancer.

6. The method according to claim 1, wherein said method for diagnosing bladder cancer is a method for the detection of non-invasive muscle bladder cancer, or a method for detection of muscle invasive bladder cancer.

7. The method according to claim 1, wherein determining if bladder cancer is present in the subject further comprises determining the bladder cancer is non-invasive muscle bladder cancer or muscle invasive bladder cancer.

8. A method for risk stratification of bladder cancer in a human subject, comprising:
performing bisulfite treatment of a DNA of a urine sample obtained from said subject;
conducting methylation-specific quantitative PCR to amplify the DNA to obtain $C_T$ values for at least two CpG regions of CpG regions of the sequences of SEQ ID NOS: 3, 5, and 7, or complementary sequences of SEQ ID NOS: 3, 5, and 7;
stratifying the risk level of bladder cancer in the subject as low-intermediate risk NMIBC, high-risk NMIBC, or MIBC based on comparing the obtained $C_T$ values of the at least two CpG regions of the sample with respective predetermined ranges of $C_T$ values of the at least two CpG regions to, wherein the predetermined ranges of $C_T$ values were derived from a statistical analysis of a training set of samples including samples in which bladder cancer is present and samples in which bladder cancer is not present; and
treating the bladder cancer in the subject based on the stratified risk level of bladder cancer in the subject.

9. The method according to claim 8, wherein stratifying the risk comprises identifying the bladder cancer as low-intermediate risk of bladder cancer, or high-risk bladder cancer.

10. A method for detecting and treating bladder cancer, comprising:
performing bisulfite treatment on a DNA obtained from a urine sample of a human subject;
detecting co-methylation of a combination of at least two DNA methylation markers on a bisulfite-treated DNA and a control, to obtain a methylation profile, wherein the DNA methylation markers comprise at least two CpG regions of SEQ ID NOS:1-2, respectively, or the complementary sequences of SEQ ID NOS:1-2, respectively; and
comparing the methylation profile of the combination of DNA methylation markers with cut-offs of a profile obtained from a statistical analysis of a training set of samples including samples in which bladder cancer is present and samples in which bladder cancer is not present, to determine the presence of bladder cancer in the urine sample; and
treating the bladder cancer of the subject if it is determined that bladder cancer is present in the subject.

11. A method for bladder cancer risk stratification, comprising:
performing bisulfite treatment on a DNA obtained from a urine sample of a human subject;
detecting co-methylation of a combination of at least two DNA methylation markers on the bisulfite-treated DNA and a control, to obtain a methylation profile, wherein the DNA methylation markers comprise at least two CpG regions of SEQ ID NOS:1-2 or the complementary sequences thereof; and
comparing the methylation profile of the combination of DNA methylation markers with a cut-offs of a profile obtained from a statistical analysis of a training set of samples including samples in which bladder cancer is present and samples in which bladder cancer is not present, to stratify the risk of bladder cancer in the urine sample; and
treating the bladder cancer of the subject with a method corresponding to the stratified risk of bladder cancer in the subject.

12. The method for bladder cancer risk stratification according to claim 11 wherein the method for co-methylation detection includes: methylation specific PCR, DNA methylation-based chip, targeted DNA methylation sequencing, digital PCR, and fluorescence quantitative PCR.

* * * * *